United States Patent
Bernier et al.

(10) Patent No.: US 11,401,254 B2
(45) Date of Patent: Aug. 2, 2022

(54) SUBSTITUTED THIOPHENECARBOXAMIDES AND ANALOGUES AS ANTIBACTERIALS AGENTS

(71) Applicant: Bayer Aktiengesellschaft, Leverkusen (DE)

(72) Inventors: David Bernier, Lyons (FR); Stéphane Brunet, Saint André de Corcy (FR); Jérémy Dufour, Lyons (FR); Thomas Knobloch, Charnay (FR); Lionel Nicolas, Lyons (FR); Tomoki Tsuchiya, Saint-Cyr-Au-Mont-d'Or (FR)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 17/256,942

(22) PCT Filed: Jul. 3, 2019

(86) PCT No.: PCT/EP2019/067824
§ 371 (c)(1),
(2) Date: Dec. 29, 2020

(87) PCT Pub. No.: WO2020/007902
PCT Pub. Date: Jan. 9, 2020

(65) Prior Publication Data
US 2022/0033374 A1    Feb. 3, 2022

(30) Foreign Application Priority Data

Jul. 5, 2018   (EP) .................... 18181930

(51) Int. Cl.
| | |
|---|---|
| C07D 333/26 | (2006.01) |
| C07D 333/38 | (2006.01) |
| A01P 1/00 | (2006.01) |
| A01N 43/10 | (2006.01) |
| A01N 55/00 | (2006.01) |
| C07D 409/12 | (2006.01) |
| C07F 7/08 | (2006.01) |

(52) U.S. Cl.
CPC .......... *C07D 333/38* (2013.01); *A01N 43/10* (2013.01); *A01N 55/00* (2013.01); *A01P 1/00* (2021.08); *C07D 409/12* (2013.01); *C07F 7/083* (2013.01); *C07F 7/0812* (2013.01)

(58) Field of Classification Search
CPC .................................................... C07D 333/26
See application file for complete search history.

(56) References Cited

U.S. PATENT DOCUMENTS 5,534,541 A    7/1996   Drauz

FOREIGN PATENT DOCUMENTS

| | | | | |
|---|---|---|---|---|
| EP | 0450355 A1 | 10/1991 | | |
| WO | 2004024692 A1 | 3/2004 | | |
| WO | WO-2004024692 A1 * | 3/2004 | ............ | A01N 53/00 |
| WO | 2004062361 A2 | 7/2004 | | |
| WO | 2004062361 A3 | 8/2005 | | |
| WO | 2012114285 A1 | 8/2012 | | |

* cited by examiner

*Primary Examiner* — John S Kenyon
(74) *Attorney, Agent, or Firm* — Morrison & Foerster LLP

(57) ABSTRACT

The present disclosure relates to substituted thiophene carboxamides and analogues thereof of formula (I) that may be used for protecting plants from bacterial diseases, in particular from bacterial diseases caused by bacteria belonging to the genus *Xanthomonas*.

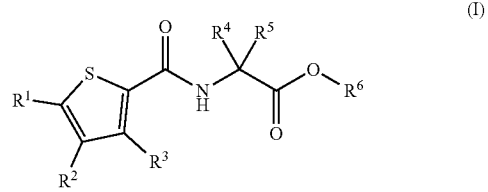

11 Claims, No Drawings

SUBSTITUTED THIOPHENECARBOXAMIDES AND ANALOGUES AS ANTIBACTERIALS AGENTS

CROSS REFERENCE TO RELATED APPLICATIONS

This application is a national stage application under 35 U.S.C. § 371 of International Application No. PCT/EP2019/067824, filed internationally on Jul. 3, 2019, which claims priority to and benefit of European Application No. 18181930.1, filed Jul. 5, 2018.

TECHNICAL FIELD

The present invention relates to substituted thiophene carboxamides and analogues thereof that may be used for protecting plants from bacterial diseases, in particular caused by bacteria belonging to the genus *Xanthomonas*.

BACKGROUND

Plant pathogenic bacteria can cause severe economically damaging diseases throughout the world. Bacteria belonging to the genus *Xanthomonas* are among the plant pathogenic bacteria considered to be the most devastating. They are the causal agents of various diseases on different host plants of agronomic significance. Examples of such diseases include bacterial spot (caused by *Xanthomonas campestris* pv. *vesicatoria*) affecting pepper and tomato, black rot of crucifers (caused by *Xanthomonas campestris* pv. *campestris*) affecting all cultivated *brassica* (e.g. Brussels sprouts, cabbage, cauliflower and broccoli), citrus canker (caused by *Xanthomonas axonopodis* pv. *citri*) affecting citrus species (lime, orange, grapefruit, pummelo), bacterial leaf blight (caused by *Xanthomonas oryzae* pv. *oryzae*) affecting rice, leaf spot (caused by *Xanthomonas arboricola* pv. *pruni*) affecting *Prunus* species (e.g. apricot, plum, peach), common bacterial blight (caused by *Xanthomonas phaseoli*) affecting bean, cassava bacterial blight (caused by *Xanthomonas axonopodis* pv. *manihotis*) affecting cassava and angular leaf spot/bacterial blight (cause by *Xanthomonas campestris* pv. *malvacearum*) affecting cotton.

Bacterial plant diseases may be controlled in different ways, including mainly the use of disease-resistant varieties of plants and the use of bactericides (natural or synthetic). The antibiotic resistance crisis in medicine and the emergence of some antibiotic resistant plant pathogens have triggered the development of alternatives to antibiotics in order to preserve their efficacy and to broaden the scope of disease management solutions. Therefore, products that do not act directly on the pathogenic bacteria, i.e. that have no direct antibiotic effect, but that stimulate the plants' own defense system have been developed. These products are known as plant defense activators. Examples of plant defense activators include Acibenzolar-S-methyl (marketed as Bion® and Actigard®), 2, 6-dichloroisonicotinic acid, β-aminobutyric acid, probenazole (Oryzemate®), salicylic acid, riboflavin, prohexadione-calcium, potassium phosphonate, harpin protein (Messenger®) and methyl jasmonate.

Though many different organic and inorganic compounds have been shown to activate induced resistance in plants, only few products are currently commercially marketed.

Therefore, the need remains to provide new chemicals and methods allowing controlling efficiently bacterial diseases, in particular diseases caused by bacteria belonging to the genus *Xanthomonas*, at low dose while not interacting directly with the bacteria so as to prevent resistance development. As the chemicals do not interact directly with the bacteria, it is unlikely that they will develop resistance to these chemicals.

The inventors have evidenced that new chemicals belonging to the class of substituted thiophenecarboxamides derivatives are offering a solution to the above problem.

Some substituted thiophenecarboxamide derivatives are known to be useful for combatting plant diseases. For instance, U.S. Pat. No. 5,534,541 or EP0450355 discloses halogeno thiophene carboxylic acid derivatives that are useful for protecting plants from attacks by plant-damaging microorganisms, such as fungi and bacteria, via a direct action or a systemic action. However, these compounds were found by the present inventors to be poorly efficient against *Xanthomonas campestris* pv. *campestris* at low dose.

Further examples of halogeno thiophene carboxylic acid derivatives are disclosed in WO2004/024692. These derivatives are said to be effective in controlling fungal diseases. They would exert their action via a direct effect on the undesired microorganisms but also thanks to a resistance inducing effect on plants. WO2004/024692 also suggests that these compounds could be useful in controlling bacterial diseases but does not provide any evidences of such activity. These compounds were also found by the present inventors to be poorly efficient against *Xanthomonas campestris* pv. *campestris* at low dose.

SUMMARY

The present invention relates to compounds of formula (I) as disclosed herein and in the claims.

The present invention also relates to a method for controlling bacterial diseases as disclosed herein and in the claims.

The present invention relates to processes for preparing compounds of formula (I) and to intermediates thereof as disclosed herein and in the claims.

Definitions

The term "$C_1$-$C_6$-alkyl" as used herein refers to a saturated, branched or straight hydrocarbon chain having 1, 2, 3, 4, 5 or 6 carbon atoms. Examples of $C_1$-$C_6$-alkyl include but are not limited to methyl, ethyl, propyl (n-propyl), 1-methylethyl (iso-propyl), butyl (n-butyl), 1-methylpropyl (sec-butyl), 2-methylpropyl (iso-butyl), 1,1-dimethylethyl (tert-butyl), pentyl, 1-methylbutyl, 2-methylbutyl, 3-methylbutyl, 2,2-dimethylpropyl, 1-ethylpropyl, 1,1-dimethylpropyl, 1,2-dimethylpropyl, hexyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl and 1-ethyl-2-methylpropyl. Particularly, said hydrocarbon chain has 1, 2, 3 or 4 carbon atoms ("$C_1$-$C_4$-alkyl"), e.g. methyl, ethyl, propyl, iso-propyl, butyl, sec-butyl, iso-butyl or tert-butyl.

The term "alkenyl" as used herein is to be understood as preferably meaning branched and unbranched alkenyl, e.g. a vinyl, propen-1-yl, propen-2-yl, but-1-en-1-yl, but-1-en-2-yl, but-2-en-1-yl, but-2-en-2-yl, but-1-en-3-yl, 2-methyl-prop-2-en-1-yl, or 2-methyl-prop-1-en-1-yl group.

The term "alkynyl" as used herein is to be understood as preferably meaning branched and unbranched alkynyl, e.g. an ethynyl, prop-1-yn-1-yl, but-1-yn-1-yl, but-2-yn-1-yl, or but-3-yn-1-yl group. The term "$C_1$-$C_6$-alkylsulfanyl" as used herein refers to a saturated, linear or branched group of formula ($C_1$-$C_6$-alkyl)-S—, in which the term "$C_1$-$C_6$-alkyl" is as defined herein. Examples of $C_1$-$C_6$-alkylsulfanyl include but are not limited to methylsulfanyl, ethylsulfanyl, propylsulfanyl, isopropylsulfanyl, butylsulfanyl, sec-butylsulfanyl, isobutylsulfanyl, tert-butylsulfanyl, pentylsulfanyl, isopentylsulfanyl, hexylsulfanyl group.

The term "aryl" as used herein refers to an aromatic, hydrocarbon, ring system, comprising from 6 to 12 carbon atoms, preferably from 6 to 10 carbon atoms. The ring system may be monocyclic or fused polycyclic (e.g. bicyclic or tricyclic) aromatic ring system. Examples of aryl include but are not limited to phenyl, azulenyl, naphthyl, biphenyl and fluorenyl.

The term "aralkyl" as used herein refers to a $C_1$-$C_6$-alkyl substituted by an aryl as defined herein. Example of aralkyl includes the benzyl group (—$CH_2$—$C_6H_5$).

The term "cycloalkyl" as used herein refers to a non-aromatic monocyclic carbon-containing ring, having 3 to 8 carbon atoms. Examples of saturated cycloalkyl include but are not limited to cyclopropyl, cyclobutyl, cyclopentyl, cyclohexyl, cycloheptyl, cyclooctyl, cyclononyl and cyclodecyl group.

The term "heterocyclyl" as used herein refers to four-, five- or six-membered, saturated or partially unsaturated heterocycles containing one to four heteroatoms independently selected from the group of oxygen, nitrogen and sulfur. If the ring contains more than one oxygen atom, they are not directly adjacent.

The term "aryl" as used herein refers to an aromatic, hydrocarbon, ring system, comprising from 6 to carbon atoms, or from 6 to 12 carbon atoms, preferably from 6 to 10 carbon atoms. The ring system may be monocyclic or fused polycyclic (e.g. bicyclic or tricyclic) aromatic ring system.

Examples of aryl include but are not limited to phenyl, azulenyl, naphthyl and fluorenyl. It is further understood that when said aryl group is substituted with one or more substituents, said substituent(s) may be at any positions on said aryl ring(s). Particularly, in the case of aryl being a phenyl group, said substituent(s) may occupy one or both ortho positions, one or both meta positions, or the para position, or any combination of these positions. This definition also applies to aryl as part of a composite substituent (e.g. aryloxy).

DETAILED DESCRIPTION

Compounds of formula (I) as shown below have been found to efficiently control diseases caused by bacteria of the genus *Xanthomonas* at low dose (i.e. dose as low as 31 ppm) while exhibiting no direct bactericide action.

Thus, the present invention relates to compounds of the formula (I):

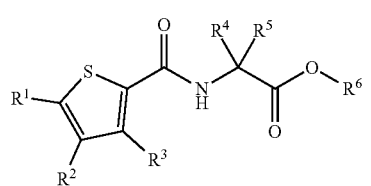

(I)

wherein
$R^1$ and $R^2$ are identical and are a chlorine atom or a bromine atom;
$R^3$ is methyl;
$R^4$ is selected from the group consisting of hydrogen atom, $C_1$-$C_6$-alkyl, aralkyl, aralkyl substituted by hydroxyl, $C_1$-$C_6$-alkyl substituted by a $C_1$-$C_6$-alkylsulfanyl and $R^5$ is a hydrogen atom; or
$R^4$ and $R^5$ form, together with the carbon atom to which they are linked, a cyclopropyl;
$R^6$ is selected from the group consisting of hydrogen atom, $C_1$-$C_6$-alkyl, $C_1$-$C_6$-haloalkyl, $C_1$-$C_6$-cyanoalkyl, $C_2$-$C_6$-alkenyl, $C_2$-$C_6$-alkynyl, $C_3$-$C_8$-cycloalkyl, aryl, aralkyl, 4-, 5- or 6-membered heterocyclyl, —$C_1$-$C_6$-alkyl-Si($C_1$-$C_6$-alkyl)$_3$ and —$C_1$-$C_6$-alkyl-$C_3$-$C_8$-cycloalkyl.

The invention encompasses pure stereoisomers of the compound of formula (I) and any mixture of these isomers.

Not encompassed herein are compounds resulting from combinations which are against natural laws and which the person skilled in the art would therefore exclude based on his/her expert knowledge. For instance, ring structures having three or more adjacent oxygen atoms are excluded.

Depending on the nature of the substituents, the compound of formula (I) may be present in the form of different stereoisomers. These stereoisomers are, for example, enantiomers, diastereomers, atropisomers or geometric isomers. Accordingly, the invention encompasses both pure stereoisomers and any mixture of these isomers. Where a compound can be present in two or more tautomer forms in equilibrium, reference to the compound by means of one tautomeric description is to be considered to include all tautomer forms.

Any of the compounds of the present invention can also exist in one or more geometric isomer forms depending on the number of double bonds in the compound. Geometric isomers by nature of substituents about a double bond or a ring may be present in cis (=Z-) or trans (=E-) form. The invention thus relates equally to all geometric isomers and to all possible mixtures, in all proportions.

The compound of formula (I) can suitably be in its free form, salt form, N-oxide form or solvate form (e.g. hydrate).

Depending on the nature of the substituents, the compound of formula (I) may be present in the form of the free compound and/or a salt thereof, such as an agrochemically active salt.

Agrochemically active salts include acid addition salts of inorganic and organic acids well as salts of customary bases. Examples of inorganic acids are hydrohalic acids, such as hydrogen fluoride, hydrogen chloride, hydrogen bromide and hydrogen iodide, sulfuric acid, phosphoric acid and nitric acid, and acidic salts, such as sodium bisulfate and potassium bisulfate. Useful organic acids include, for example, formic acid, carbonic acid and alkanoic acids such as acetic acid, trifluoroacetic acid, trichloroacetic acid and propionic acid, and also glycolic acid, thiocyanic acid, lactic acid, succinic acid, citric acid, benzoic acid, cinnamic acid, oxalic acid, saturated or mono- or diunsaturated fatty acids having 6 to 20 carbon atoms, alkylsulfuric monoesters, alkylsulfonic acids (sulfonic acids having straight-chain or branched alkyl radicals having 1 to 20 carbon atoms), arylsulfonic acids or aryldisulfonic acids (aromatic radicals, such as phenyl and naphthyl, which bear one or two sulfonic acid groups), alkylphosphonic acids (phosphonic acids having straight-chain or branched alkyl radicals having 1 to 20 carbon atoms), arylphosphonic acids or aryldiphosphonic acids (aromatic radicals, such as phenyl and naphthyl, which bear one or two phosphonic acid radicals), where the alkyl and aryl radicals may bear further substituents, for example p-toluenesulfonic acid, salicylic acid, p-aminosalicylic acid, 2-phenoxybenzoic acid, 2-acetoxybenzoic acid, etc.

Solvates of the compounds of formula (I) or their salts are stoichiometric compositions of the compounds with solvents.

The compounds of formula (I) may exist in multiple crystalline and/or amorphous forms. Crystalline forms include unsolvated crystalline forms, solvates and hydrates.

In some embodiments, in the above formula (I), $R^4$ is selected from the group consisting of hydrogen atom, $C_1$-$C_6$-alkyl, benzyl, benzyl substituted by hydroxyl, $C_1$-$C_6$-alkyl substituted by a $C_1$-$C_6$-alkylsulfanyl and $R^5$ is a hydrogen atom; or $R^4$ and $R^5$ form, together with the carbon atom to which they are linked, a cyclopropyl.

In some embodiments, in the above formula (I), $R^4$ is selected from the group consisting of hydrogen atom, $C_1$-$C_6$-alkyl, benzyl, benzyl substituted by hydroxyl, $C_1$-$C_6$-alkyl substituted by a $C_1$-$C_6$-alkylsulfanyl and $R^5$ is a hydrogen atom.

In some embodiments, in the above formula (I), $R^4$ is a hydrogen atom, a $C_1$-$C_6$-alkyl, an aralkyl or a $C_1$-$C_6$-alkyl substituted by a $C_1$-$C_6$-alkylsulfanyl and $R^5$ is a hydrogen atom; or $R^4$ and $R^5$ form, together with the carbon atom to which they are linked, a cyclopropyl.

In some embodiments, in the above formula (I), $R^4$ is a hydrogen atom, a $C_1$-$C_6$-alkyl, an aralkyl or a $C_1$-$C_6$-alkyl substituted by a $C_1$-$C_6$-alkylsulfanyl and $R^5$ is a hydrogen atom.

Non-limiting examples of suitable $R^4$ groups include any of the $R^4$ groups disclosed in column "$R^4$" of Table I.1.

In some embodiments, in the above formula (I), $R^6$ is selected from the group consisting of hydrogen atom, $C_1$-$C_6$-alkyl, $C_1$-$C_6$-haloalkyl, $C_1$-$C_6$-cyanoalkyl, $C_2$-$C_6$-alkenyl, $C_2$-$C_6$-alkynyl, $C_3$-$C_8$-cycloalkyl, phenyl, benzyl, 4-, 5- or 6-membered heterocyclyl, —$C_1$-$C_6$-alkyl-Si($C_1$-$C_6$-alkyl)$_3$ and —$C_1$-$C_6$-alkyl-cyclopropyl.

When $R^6$ is a 4-, 5- or 6-membered heterocyclyl, it may be a saturated or partially unsaturated heterocyclyl. Examples of saturated 4-, 5- or 6-membered heterocyclyl include but are not limited to 4-membered ring such as azetidinyl, oxetanyl, thietanyl, dioxothietanyl, 5-membered ring such as oxolanyl, 1,3-dioxolanyl, tetrahydrothienyl, pyrrolidinyl, pyrazolidinyl, imidazolidinyl, triazolidinyl, isoxazolidinyl, oxazolidinyl, oxadiazolidinyl, thiazolidinyl, isothiazolidinyl, thiadiazolidinyl, 6-membered ring such as piperidinyl, hexahydropyridazinyl, hexahydropyrimidinyl, piperazinyl, triazinanyl, hexahydrotriazinyl, oxanyl, dioxanyl, tetrahydrothiopyranyl, dithianyl, morpholinyl, 1,2-oxazinanyl, oxathianyl, thiomorpholinyl. Examples of partially unsaturated non-aromatic hererocyles include but are not limited to 5-membered ring such as dihydrofuranyl, 1,3-dioxolyl, dihydrothienyl, pyrrolinyl, dihydroimidazolyl, dihydropyrazolyl, isoxazolinyl, dihydrooxazolyl, dihydrothiazolyl or 6-membered ring such as pyranyl, thiopyranyl, thiazinyl and thiadiazinyl.

In some embodiments, in the above formula (I), $R^6$ is selected from the group consisting of hydrogen atom, $C_1$-$C_6$-alkyl, $C_1$-$C_6$-haloalkyl, $C_1$-$C_6$-cyanoalkyl, $C_2$-$C_6$-alkenyl, $C_2$-$C_6$-alkynyl, $C_3$-$C_8$-cycloalkyl, phenyl, benzyl, oxetanyl, thietanyl, dioxothietanyl, oxolanyl, oxanyl, —$C_1$-$C_6$-alkyl-Si($C_1$-$C_6$-alkyl)$_3$ and —$C_1$-$C_6$-alkyl-cyclopropyl.

In some embodiments, in the above formula (I), $R^6$ is a hydrogen atom or a $C_1$-$C_6$-alkyl.

Non-limiting examples of suitable $R^6$ groups include any of the $R^6$ groups disclosed in column "$R^6$" of Table I.1.

In some embodiments, in the above formula (I), $R^1$ and $R^2$ are a chlorine atom.

In some embodiments, in the above formula (I), $R^1$ and $R^2$ are a bromine atom.

The above specified definitions of $R^1$, $R^2$, $R^4$ and $R^6$ and can be combined in various manners to provide sub-classes of compounds according to the invention.

Non-limiting examples of sub-classes of compounds include the sub-classes described herein below.

In some embodiments (referred herein as embodiment Ia), compounds of the invention are compounds of formula (I):

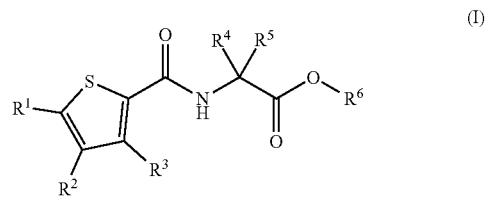

wherein
$R^1$ and $R^2$ are identical and are a chlorine atom or a bromine atom;
$R^3$ is methyl;
$R^4$ is selected from the group consisting of hydrogen atom, $C_1$-$C_6$-alkyl, benzyl, benzyl substituted by hydroxyl, $C_1$-$C_6$-alkyl substituted by a $C_1$-$C_6$-alkylsulfanyl and $R^5$ is a hydrogen atom; or
$R^4$ and $R^5$ form, together with the carbon atom to which they are linked, a cyclopropyl;
$R^6$ is selected from the group consisting of hydrogen atom, $C_1$-$C_6$-alkyl, $C_1$-$C_6$-haloalkyl, $C_1$-$C_6$-cyanoalkyl, $C_2$-$C_6$-alkenyl, $C_2$-$C_6$-alkynyl, $C_3$-$C_8$-cycloalkyl, phenyl, benzyl, oxetanyl, thietanyl, dioxothietanyl, oxolanyl, oxanyl, —$C_1$-$C_6$-alkyl-Si($C_1$-$C_6$-alkyl)$_3$ and —$C_1$-$C_6$-alkyl-cyclopropyl.

In some embodiments (referred herein as embodiment Ib), compounds of the invention are compounds of formula (I):

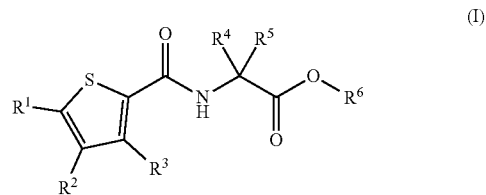

wherein
$R^1$ and $R^2$ are identical and are a chlorine atom or a bromine atom;
$R^3$ is methyl;
$R^4$ is a hydrogen atom, a $C_1$-$C_6$-alkyl, an aralkyl or a $C_1$-$C_6$-alkyl substituted by a $C_1$-$C_6$-alkylsulfanyl and $R^5$ is a hydrogen atom; or
$R^4$ and $R^5$ form, together with the carbon atom to which they are linked, a cyclopropyl;
$R^6$ is a hydrogen atom or a $C_1$-$C_6$-alkyl.

In some embodiments in accordance with embodiments Ia and Ib, when $R^4$ and $R^5$ do not form, together with the carbon atom to which they are linked, a cyclopropyl, $R^4$ is preferably a hydrogen atom, a $C_1$-$C_4$-alkyl, a benzyl group or a $C_1$-$C_4$-alkyl substituted by a $C_1$-$C_4$-alkylsulfanyl, more preferably $R^4$ is hydrogen, isopropyl, isobutyl, methylsulfanylethyl or benzyl.

In some embodiments in accordance with embodiments Ia and Ib, $R^6$ is a hydrogen atom or a $C_1$-$C_4$-alkyl, preferably $R^6$ is hydrogen, methyl or ethyl.

In some embodiments in accordance with embodiments Ia and Ib, $R^1$ and $R^2$ are a chlorine atom. In some embodiments in accordance with embodiments Ia and Ib, $R^1$ and $R^2$ are a bromine atom.

In some embodiments in accordance with embodiments Ia and Ib, when $R^1$ and $R^2$ are a bromine atom, $R^4$ is a hydrogen atom, a $C_1$-$C_6$-alkyl, an aralkyl or a $C_1$-$C_6$-alkyl substituted by a $C_1$-$C_6$-alkylsulfanyl and $R^5$ is a hydrogen atom.

In some embodiments, compounds according to the present invention are compounds of the formula (I):

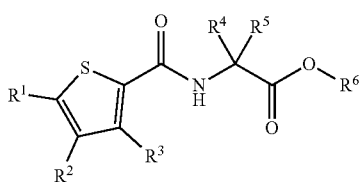

wherein
$R^1$ and $R^2$ are identical and are a chlorine atom or a bromine atom;
$R^3$ is methyl;
$R^4$ is a hydrogen atom, a $C_1$-$C_4$-alkyl, a benzyl group or a $C_1$-$C_4$-alkyl substituted by a $C_1$-$C_4$-alkylsulfanyl, preferably $R^4$ is hydrogen, isopropyl, isobutyl, methylsulfanylethyl or benzyl and $R^5$ is a hydrogen atom; or
$R^4$ and $R^5$ form, together with the carbon atom to which they are linked, a cyclopropyl;
$R^6$ is a hydrogen atom or a $C_1$-$C_4$-alkyl, preferably $R^6$ is hydrogen, methyl or ethyl.

The compounds of formula (I) may be used for controlling bacterial diseases, in particular for controlling diseases caused by bacteria belonging to the genus *Xanthomonas*.

Processes for the Preparation of Compounds of Formula (I)

The present invention relates to processes for the preparation of compounds of formula (I). The compounds of formula (I) can be prepared by various routes in analogy to known processes (see references therein), and by one or more of the following synthetic routes described herein below and in the experimental part.

General Synthetic Routes to the Compounds of Formula (I)

Unless indicated otherwise, in the following, $R^1$, $R^2$, $R^3$, $R^4$, $R^5$ and $R^6$ have the same meaning as given above for compounds of formula (I).

Process A1

Compounds of formula (I) as herein-defined can be prepared by a process A1 which comprises the step of reacting a compound of formula (IV) or one of its salts with a compound of formula (V) or one of its salts as illustrated by the following reaction scheme:

Process A1

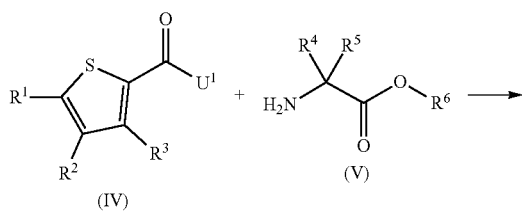

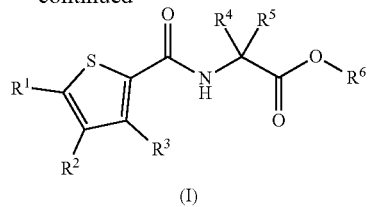

wherein $U^1$ is a halogen atom, a hydroxy group or a $C_1$-$C_6$-alkoxy group.

When $U^1$ represents a hydroxy group, process A1 is advantageously conducted in the presence of a condensing agent. Suitable condensing agents may be selected in the non-limited list consisting of acid halide former, such as phosgene, phosphorous tribromide, phosphorous trichloride, phosphorous pentachloride, phosphorous trichloride oxide, oxalyl chloride or thionyl chloride; anhydride former, such as ethyl chloroformate, methyl chloroformate, isopropyl chloroformate, isobutyl chloroformate or methanesulfonyl chloride; carbodiimides, such as N,N'-dicyclohexylcarbodiimide (DCC), N-(3-Dimethylaminopropyl)-N'-ethylcarbodiimide hydrochloride (EDC) or other customary condensing agents, such as phosphorous pentoxide, polyphosphoric acid, bis(2-oxo-3-oxazolidinyl)phosphinic chloride, 1-[bis(dimethylamino)methylene]-1H-1,2,3-triazolo[4,5-b]pyridinium 3-oxid hexafluorophosphate (HATU), 2-(1H-Benzotriazole-1-yl)-1,1,3,3-tetramethylaminium tetrafluoroborate (TBTU), (1-cyano-2-ethoxy-2-oxoethylidenaminooxy)dimethylamino-morpholino-carbenium hexafluorophosphate, N,N'-carbonyl-diimidazole, 2-ethoxy-N-ethoxycarbonyl-1,2-dihydroquinoline (EEDQ), triphenylphosphine/tetrachloro-methane, 4-(4,6-dimethoxy[1.3.5]-triazin-2-yl)-4-methylmorpholinium chloride hydrate, bis(2-oxo-3-oxazolidinyl)phosphinic chloride (BOP-Cl), bromotripyrrolidinophosphoniumhexafluorophosphate (PyBroP), 2-chloro-1,3-dimethylimidazolinium chloride (DMC) and propanephosphonic anhydride (T3P).

When $U^1$ represents a halogen atom, process A1 is advantageously conducted in the presence of an acid binder. Suitable acid binders for carrying out process A1 are in each case all inorganic and organic bases that are customary for such reactions. Preference is given to alkali metal carbonates, such as cesium carbonate, sodium carbonate, potassium carbonate, potassium bicarbonate, sodium bicarbonate, alkaline earth metal acetates, such as sodium acetate, potassium acetate, calcium acetate and also tertiary amines, such as trimethylamine, triethylamine, diisopropylethylamine, tributylamine, N,N-dimethylaniline, N-methylpiperidine, N,N-dimethylpyridin-4-amine, diazabicyclooctane (DABCO), diazabicyclo-nonene (DBN) or diazabicycloundecene (DBU), or aromatic bases such as pyridine.

When $U^1$ represents a $C_1$-$C_6$-alkoxy group, process A1 can be conducted with an excess of the amine component, optionally in the presence of a Lewis acid such as trimethylaluminium.

If appropriate, process A1 can be performed in the presence of a base and if appropriate, in the presence of a solvent, preferably under anhydrous conditions.

Suitable solvents for carrying out process A1 are not particularly limited. They can be customary inert organic solvents as long as it is not dissolving the compound to react therewith or exhibit any particular interaction therewith. Preference is given to using optionally halogenated, aliphatic, alicyclic or aromatic hydrocarbons, such as petroleum ether, pentane, hexane, heptane, cyclohexane, methylcyclohexane, benzene, toluene, xylene, decalin, ISOPAR™ E or ISOPAR™ G, chlorobenzene, dichlorobenzene, dichloromethane, chloroform, carbon tetrachloride, 1,2-dichloroethane or trichloroethane; ethers, such as diethyl ether, diisopropyl ether, methyl tert-butyl ether, methyl tert-amyl ether, dioxane, tetrahydrofuran, 2-methyltetrahydrofuran, 1,2-dimethoxyethane, 1,2-diethoxyethane or anisole; nitriles, such as acetonitrile, propionitrile, n- or iso-butyronitrile or benzonitrile; amides, such as N,N-dimethylformamide, N,N-dimethylacetamide, N-methylformanilide, N-methylpyrrolidone or hexamethylphosphoric triamide; ureas, such as 1,3-dimethyl-3,4,5,6-tetrahydro-2(1H)-pyrimidinone; esters, such as methyl acetate or ethyl acetate, sulfoxides, such as dimethyl sulfoxide, or sulfones, such as sulfolane; and a mixture thereof.

Process A1 may be performed in an inert atmosphere such as argon or nitrogen atmosphere. When carrying out process A1, 1 mole or an excess of compound of formula (V) and from 1 to 5 moles of base can be employed per mole of compound of formula (IV). It is also possible to employ the reaction components in other ratios. Work-up is carried out by known methods.

Compounds of formula (V) are commercially available or can be prepared by well-known processes.

Compounds of formula (IV) wherein $U^1$ represents a hydroxy group are commercially available, can be prepared from compounds of formula (IV) wherein $U^1$ represents a $C_1$-$C_6$-alkoxy group by well-known processes such as basic hydrolysis or can be prepared by known processes (Beilstein *J. Org. Chem.* 2007, 3, No. 23)

Compounds of formula (IV) wherein $U^1$ represents a halogen are commercially available or can be prepared from compounds of formula (IV) wherein $U^1$ represents a hydroxy group by well-known processes.

Compounds of formula (IV) wherein $U^1$ represents a $C_1$-$C_6$-alkoxy group can be prepared from compounds of formula (IV) wherein $U^1$ represents a hydroxy group by well-known processes.

Process B1

Compounds of formula (I) as herein-defined can be prepared by a process B1 which comprises the step of reacting a compound of formula (VI) or one of its salts with a compound of formula (VII) or one of its salts as illustrated by the following reaction scheme:

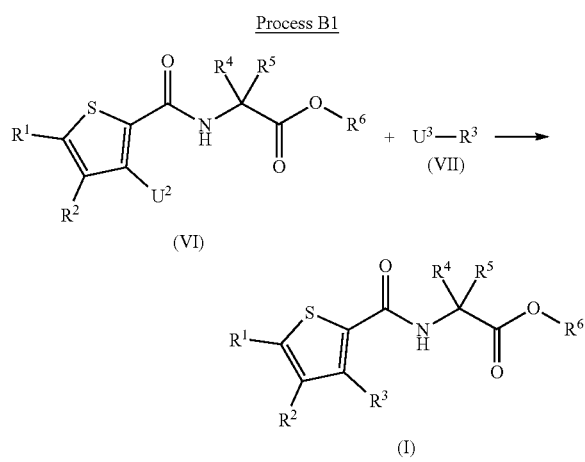

wherein $U^2$ is a bromine atom, an iodine atom, a mesylate group, a tosylate group or a triflate group and $U^3$ is a boron derivative such as a boronic acid, a boronic ester derivative, a potassium trifluoroborate derivative or a halogenometal that can be complexed by 1 to 2 ligands such as a halogenomagnesium or a halogenozinc, provided that when $R^1$ and $R^2$ are bromine atoms, $U^2$ is not a bromine atom.

Process B1 can be performed in the presence of a transition metal catalyst such as palladium and if appropriate, in the presence of a phosphine ligand or a N-heterocyclic carbene ligand, if appropriate, in the presence of a base and if appropriate, in the presence of a solvent according to known processes (WO2012054721, *Angew. Chem. Int. Ed.* 2017, 56, 1581, *Angew. Chem. Int. Ed.* 2017, 56, 7078, and cited references therein).

Process B1 can be carried out in the presence of a catalyst, such as a metal salt or complex. Suitable metal derivatives for this purpose are transition metal catalysts such as palladium. Suitable metal salts or complexes for this purpose are for example, palladium chloride, palladium acetate, tetrakis(triphenylphosphine)palladium(0), bis(dibenzylideneacetone)palladium(0), tris(dibenzylideneacetone)dipalladium(0), bis(triphenylphosphine)palladium(II) dichloride, [1,1'-bis(diphenylphosphino)ferrocene]dichloropalladium(II), bis(cinnamyl)dichlorodipalladium(II), bis(allyl)-dichlorodipalladium(II), [1,1'-Bis(di-tert-butylphosphino)ferrocene]dichloropalladium(II), di-p-iodobis(tri-tert-butylphosphino)dipalladium(I) or di-p-bromobis(tri-tert-butylphosphino)dipalladium(I).

It is also possible to generate a palladium complex in the reaction mixture by separate addition to the reaction of a palladium salt and a ligand or salt, such as triethylphosphine, tri-tert-butylphosphine, tri-tert-butylphosphonium tetrafluoroborate, tricyclohexylphosphine, 2-(dicyclohexylphosphino)biphenyl, 2-(di-tert-butylphosphino)biphenyl, 2-(dicyclohexylphosphino)-2'-(N,N-dimethylamino)biphenyl, 2-(tert-butylphosphino)-2'-(N,N-dimethylamino)biphenyl, 2-di-tert-butylphosphino-2',4',6'-triisopropylbiphenyl 2-dicyclohexylphosphino-2',4',6'-triisopropylbiphenyl, 2-dicyclohexylphosphino-2,6'-dimethoxybiphenyl, 2-dicyclohexylphosphino-2',6'-diisopropoxybiphenyl, triphenylphosphine, tris-(o-tolyl)phosphine, sodium 3-(diphenylphosphino)benzenesulfonate, tris-2-(methoxyphenyl)phosphine, 2,2'-bis(diphenylphosphino)-1,1'-binaphthyl, 1,4-bis(diphenylphosphino)butane, 1,2-bis(diphenylphosphino) ethane, 1,4-bis(dicyclohexylphosphino) butane, 1,2-bis(dicyclohexylphosphino)-ethane, 2-(dicyclohexylphosphino)-2'-(N,N-dimethylamino)-biphenyl, 1,1'-bis(diphenylphosphino)-ferrocene, (R)-(−)-1-[(S)-2-diphenyl-phosphino)ferrocenyl]ethyldicyclohexylphosphine, tris-(2,4-tert-butyl-phenyl)phosphite, di(1-adamantyl)-2-morpholinophenylphosphine or 1,3-bis(2,4,6-trimethylphenyl)imidazolium chloride.

It is also advantageous to choose the appropriate catalyst and/or ligand from commercial catalogues such as "Metal Catalysts for Organic Synthesis" by Strem Chemicals or "Phosphorous Ligands and Compounds" by Strem Chemicals.

Suitable bases for carrying out process B1 can be inorganic and organic bases which are customary for such reactions. Preference is given to using alkaline earth metal or alkali metal hydroxides, such as sodium hydroxide, calcium hydroxide, potassium hydroxide or other ammonium hydroxide derivatives; alkaline earth metal, alkali metal or ammonium fluorides such as potassium fluoride, cesium fluoride or tetrabutylammonium fluoride; alkaline earth metal or alkali metal carbonates, such as sodium carbonate, potassium carbonate, potassium bicarbonate, sodium bicarbonate or cesium carbonate; alkali metal or alkaline earth metal acetates, such as sodium acetate, lithium acetate, potassium acetate or calcium acetate; alkali metal or alkaline earth metal phosphate, such as tripotassium phosphate alkali; alkali metal alcoholates, such as potassium tert-butoxide or sodium tert-butoxide; tertiary amines, such as trimethylamine, triethylamine, tributylamine, N,N-dimethylaniline, N,N-dicyclohexylmethylamine, N,N-diisopropylethylamine, N-methylpiperidine, N,N-dimethylaminopyridine, diazabicyclooctane (DABCO), diazabicyclononene (DBN) or diazabicycloundecene (DBU); and also aromatic bases, such as pyridine, picolines, lutidines or collidines.

Suitable solvents for carrying out process B1 can be customary inert organic solvents. Preference is given to using optionally halogen atomated aliphatic, alicyclic or aromatic hydrocarbons, such as petroleum ether, pentane, hexane, heptane, cyclohexane, methylcyclohexane, benzene, toluene, xylene or decalin; chlorobenzene, dichlorobenzene, dichloromethane, chloroform, carbon tetrachloride, dichloroethane or trichloroethane; ethers, such as diethyl ether, diisopropyl ether, methyl tert-butyl ether, methyl tert-amyl ether, dioxane, tetrahydrofuran, 2-methyltetrahydrofuran, 1,2-dimethoxyethane, 1,2-diethoxyethane or anisole; nitriles, such as acetonitrile, propionitrile, n- or iso-butyronitrile or benzonitrile; amides, such as N,N-dimethylformamide, N,N-dimethylacetamide, N-methylformanilide, N-methylpyrrolidone or hexamethylphosphoric triamide; ureas, such as 1,3-dimethyl-3,4,5,6-tetrahydro-2 (1H)-pyrimidinone; esters, such as methyl acetate or ethyl acetate, sulfoxides, such as dimethyl sulfoxide, or sulfones, such as sulfolane; and a mixture thereof.

It can also be advantageous to carry out process B1 with a co-solvent such as water or an alcohol such as methanol, ethanol, propanol, isopropanol or tert-butanol.

Process B1 may be performed in an inert atmosphere such as argon or nitrogen atmosphere. When carrying out process B1, 1 mole or an excess of compound of formula (VII) and from 1 to 5 moles of base and from 0.01 to 20 mole percent of a palladium complex can be employed per mole of compound of formula (VI). It is also possible to employ the reaction components in other ratios. Work-up is carried out by known methods.

Compounds of formula (VII) are commercially available or can be prepared by well-known processes.

Compounds of formula (VI) can be prepared by reacting a compound of formula (VIII) with a compound of formula (V) in the conditions as described in connection with process A1:

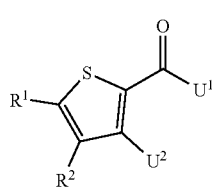

(VIII)

wherein $U^2$ and $U^1$ are as herein-defined.

Compounds of formula (VIII) wherein $U^2$ is chlorine atom, a bromine atom or an iodine atom are commercially available or can be prepared by well-known processes with the similar reaction conditions than the ones disclosed to prepare compounds of formula (IV).

Compounds of formula (VIII) wherein $U^2$ is a mesylate group, a tosylate group or a triflate group can be prepared by well-known processes from the corresponding compound bearing a hydroxy group at the $U_2$ position.

Process C1

Compounds of formula (I) as herein defined can be prepared by a process C1 from a compound of formula (IX) or one of its salts by performing a bromination or chlorination reaction as illustrated in the following reaction scheme:

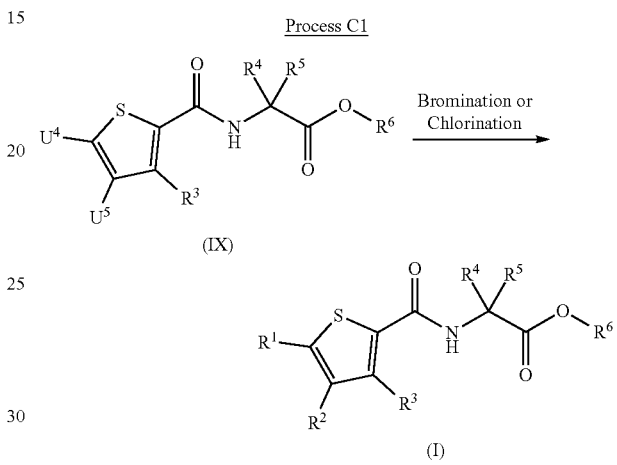

wherein $U^4$ is a hydrogen atom, a chlorine atom or a bromine atom and $U^5$ is a hydrogen atom, a chlorine atom or a bromine atom provided that at least one of $U^4$ or $U^5$ is a hydrogen atom.

Process C1 can be carried out according to known processes (WO2008109786, WO2007098356).

Process C1 is performed in the presence of a bromination agent or a chlorination agent and if appropriate, in the presence of a solvent.

Suitable bromination or chlorination agents for carrying out process C1 are not particularly limited provided they are used for bromination or chlorination. Examples of bromination agents include bromine, N-bromosuccinimide and 1,3-dibromo-5,5-dimethyl-2,4-imidazolidinedione.

Examples of chlorination agents include N-chlorosuccinimide, sulfuryl chloride and 1,3-dichloro-5,5-dimethyl-2,4-imidazolidinedione.

Suitable solvents for carrying out process C1 are not particularly limited. They can be customary inert organic solvents as long as it is not dissolving the compound to react therewith or exhibit any particular interaction therewith. Suitable solvents can be for instance the solvents disclosed in connection with process A1. To carry out process C1, it can also be advantageous to use an organic acid such as acetic acid as a solvent or a co-solvent.

Process D1

Compounds of formula (I) as herein-defined can be prepared by a process D1 comprising the step of performing a diazotation of a compound of formula (X) or one of its salts followed by an aromatic substitution to provide a compound of formula (I) as illustrated in the following reaction scheme:

Process D1

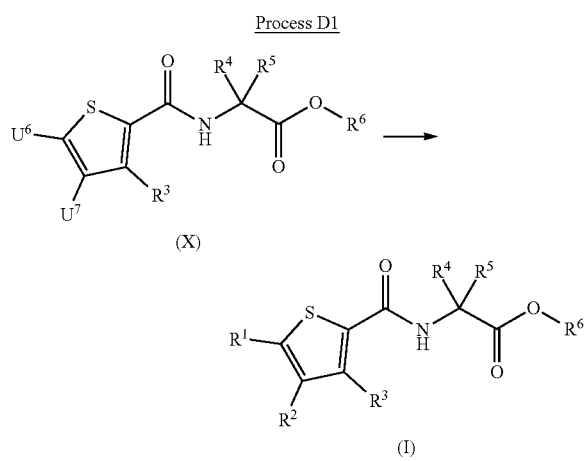

wherein $U^6$ is an amino group, a chlorine atom or a bromine atom and $U^7$ is an amino group, a chlorine atom or a bromine atom provided that at least one of $U^6$ or $U^7$ is an amino group.

Process D1 can be carried out according to known processes (The Chemistry of diazonium and diazo groups; Saul Patai; Wiley-Interscience; 1978; 288-280 and 645-657; Account of Chemical Research (2018), 57, 496 and cited references therein).

Compounds of formula (X) or one of its salts as herein-defined can be prepared by a process comprising the step of deprotecting a compound of formula (XI) or one of its salts as illustrated in the following reaction scheme:

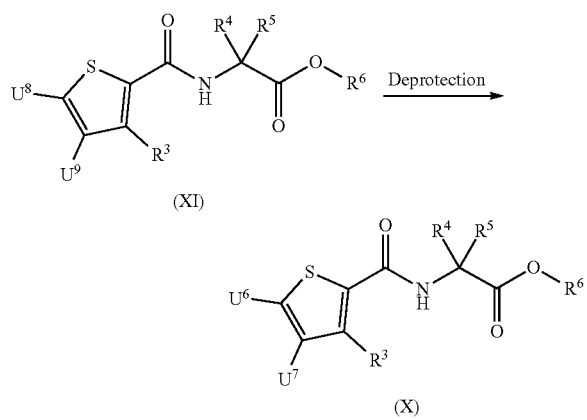

wherein $U^8$ is a protected amino group, a chlorine atom or a bromine atom and $U^9$ is a protected amino group, a chlorine atom or a bromine atom provided that at least one of $U^8$ or $U^9$ is a protected amino group, $U^6$ is an amino group, a chlorine atom or a bromine atom and $U^7$ is an amino group, a chlorine atom or a bromine atom provided that at least one of $U^6$ or $U^7$ is an amino group.

Examples of protecting groups of the amino group include a benzyl group, a 4-methoxybenzyl group, an allyl group, an unsubstituted or substituted $C_1$-$C_6$-alkylsulfonyl, a trifluoromethylsulfonyl, an unsubstituted or substituted phenylsulfonyl, an unsubstituted or substituted $C_1$-$C_6$-alkoxycarbonyl, an unsubstituted or substituted benzyloxycarbonyl, an allyloxycarbonyl, an acetyl group or a trifluoroacetyl group.

The deprotection process can be carried out according to known processes for removing protecting groups (Greene's Protective Groups in Organic Synthesis; Peter G. M. Wuts; Wiley; Fifth Edition; 2014; 895-1194). For example, tert-butoxycarbonyl and benzyloxycarbonyl protecting groups can be removed in an acidic medium (for example with hydrochloric acid or trifluoroacetic acid). Benzylic protecting groups can be removed hydrogenolytically with hydrogen in the presence of a catalyst (for example palladium on activated carbon). Trifluoroacetyl group can be removed in a basic medium (for example with potassium carbonate or lithium hydroxide).

Compounds of formula (X) can be prepared from compounds of formula (XII) or one of its salts and compounds of formula (XI) can be prepared from compounds of formula (XIII) or one of its salts by reaction with a compound of formula (V) in the conditions as described in process A1:

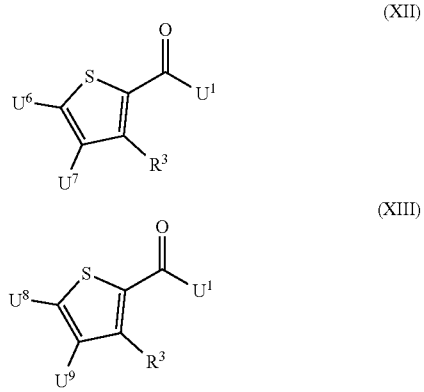

wherein $U^6$, $U^7$, $U^8$ and $U^9$ are as herein-defined, $U^1$ is a halogen atom, a hydroxy group or a $C_1$-$C_6$-alkoxy group.

Compounds of formula (XII) and compounds of formula (XIII) are commercially available or can be prepared by well-known processes with the similar reactions conditions than the ones disclosed to prepare compounds of formula (IV).

Compounds of formula (I) or one of its salts wherein $R^6$ represents a hydrogen atom can be prepared from compounds of formula (I) wherein $R^6$ represents $C_1$-$C_6$-alkyl, $C_1$-$C_6$-haloalkyl, $C_1$-$C_6$-cyanoalkyl, $C_2$-$C_6$-alkenyl, $C_2$-$C_6$-alkynyl, $C_3$-$C_8$-cycloalkyl, aryl, aralkyl, 4-, 5- or 6-membered heterocyclyl, —$C_1$-$C_6$-alkyl-Si($C_1$-$C_6$-alkyl)$_3$ or —$C_1$-$C_6$-alkyl-cyclopropyl by well-known processes such as basic hydrolysis.

Compounds of formula (I) wherein $R^6$ represents $C_1$-$C_6$-alkyl, $C_1$-$C_6$-haloalkyl, $C_1$-$C_6$-cyanoalkyl, $C_2$-$C_6$-alkenyl, $C_2$-$C_6$-alkynyl, $C_3$-$C_8$-cycloalkyl, aryl, aralkyl, 4-, 5- or 6-membered heterocyclyl, —$C_1$-$C_6$-alkyl-Si($C_1$-$C_6$-alkyl)$_3$ or —$C_1$-$C_6$-alkyl-cyclopropyl can be prepared from compounds of formula (I) or one of its salts wherein $R^6$ represents a hydrogen atom by well-known processes.

The intermediates as disclosed herein may be efficient in controlling bacteria and/or fungi.

Intermediates for the Preparation of Compounds of Formula (I)

Unless indicated otherwise, in the following, $R^1$, $R^2$, $R^3$, $R^4$, $R^5$ and $R^6$ have the same meaning as given above for compounds of formula (I).

The present invention relates to intermediates for the preparation of compounds of formula (I).

Compounds of formula (IVa) are provided:

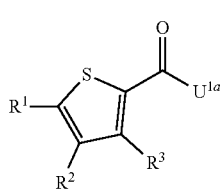

wherein
$R^1$ and $R^2$ are identical and are a chlorine atom or a bromine atom;
$R^3$ is methyl;
$U^{1a}$ is a hydroxy group or a $C_1$-$C_6$-alkoxy group,
provided that the compound of formula (IVa) does not represent:
- ethyl 4,5-dibromo-3-methylthiophene-2-carboxylate [2088257-63-8],
- 4,5-dichloro-3-methylthiophene-2-carboxylic acid [854626-34-9],
- 4,5-dibromo-3-methylthiophene-2-carboxylic acid [854626-32-7],
- methyl 4,5-dichloro-3-methylthiophene-2-carboxylate [854626-27-0] and
- methyl 4,5-dibromo-3-methylthiophene-2-carboxylate [648412-53-7].

Compounds of formula (VIa) are provided:

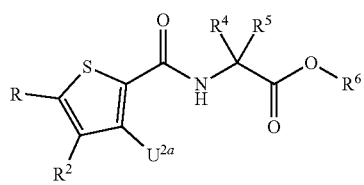

wherein
$R^1$ and $R^2$ are identical and are a chlorine atom or a bromine atom;
$R^4$ is selected from the group consisting of hydrogen atom, $C_1$-$C_6$-alkyl, aralkyl, aralkyl substituted by hydroxyl, $C_1$-$C_6$-alkyl substituted by a $C_1$-$C_6$-alkylsulfanyl and $R^5$ is a hydrogen atom; or
$R^4$ and $R^5$ form, together with the carbon atom to which they are linked, a cyclopropyl;
$R^6$ is selected from the group consisting of hydrogen atom, $C_1$-$C_6$-alkyl, $C_1$-$C_6$-haloalkyl, $C_1$-$C_6$-cyanoalkyl, $C_2$-$C_6$-alkenyl, $C_2$-$C_6$-alkynyl, $C_3$-$C_8$-cycloalkyl, aryl, aralkyl, 4-, 5- or 6-membered heterocyclyl, —$C_1$-$C_6$-alkyl-Si($C_1$-$C_6$-alkyl)$_3$ and —$C_1$-$C_6$-alkyl-$C_3$-$C_8$-cycloalkyl;
$U^2_a$ is a bromine atom, an iodine atom, a mesylate group, a tosylate group or a triflate group, wherein $R^4$ is selected from the group consisting of hydrogen atom, $C_1$-$C_6$-alkyl, aralkyl, aralkyl substituted by hydroxyl, $C_1$-$C_6$-alkyl substituted by a $C_1$-$C_6$-alkylsulfanyl and $R^5$ is a hydrogen atom when $R^6$ is hydrogen atom or $C_1$-$C_6$-alkyl; and
provided that when $R^1$ and $R^2$ are bromine atoms, $U^2_a$ is not a bromine atom.

Compounds of formula (VI)a wherein $U^2_a$ is a bromine atom or iodine atom have been found to be efficient in controlling fungi and/or bacteria.

Compounds of formula (VIIIa) are provided:

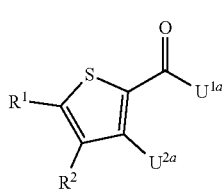

wherein
$R^1$ and $R^2$ are identical and are a chlorine atom or a bromine atom;
$U^{1a}$ is a hydroxy group or a $C_1$-$C_6$-alkoxy group;
$U^{2a}$ is a bromine atom, an iodine atom, a mesylate group, a tosylate group or a triflate group, provided that when $R^1$ and $R^2$ are bromine atoms, $U^{2a}$ is not a bromine atom; and
provided that the compound of formula (VIIIa) does not represent:
- methyl 4,5-dibromo-3-chlorothiophene-2-carboxylate [1501789-47-4],
- 4,5-dibromo-3-iodothiophene-2-carboxylic acid [854626-46-3],
- 4,5-dibromo-3-chlorothiophene-2-carboxylic acid [503308-99-4] and
- ethyl 4,5-dibromo-3-chlorothiophene-2-carboxylate [503308-98-3].

Compounds of formula (VIIIa) are provided:

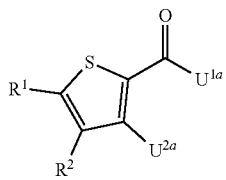

wherein
$R^1$ and $R^2$ are identical and are a chlorine atom or a bromine atom; $U^{1a}$ is a hydroxy group or a $C_1$-$C_6$-alkoxy group;
$U^{2a}$ is a mesylate group, a tosylate group or a triflate group.

Compounds of formula (IXa) and (IXb) are provided:

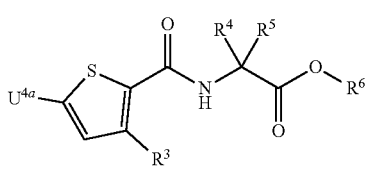

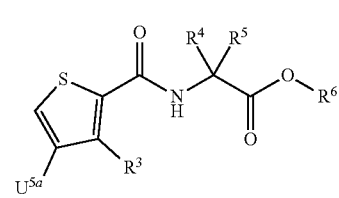

wherein

R$^3$ is methyl;

R$^4$ is selected from the group consisting of hydrogen atom, C$_1$-C$_6$-alkyl, aralkyl, aralkyl substituted by hydroxyl, C$_1$-C$_6$-alkyl substituted by a C$_1$-C$_6$-alkylsulfanyl and R$^5$ is a hydrogen atom; or R$^4$ and R$^5$ form, together with the carbon atom to which they are linked, a cyclopropyl;

R$^6$ is selected from the group consisting of hydrogen atom, C$_1$-C$_6$-alkyl, C$_1$-C$_6$-haloalkyl, C$_1$-C$_6$-cyanoalkyl, C$_2$-C$_6$-alkenyl, C$_2$-C$_6$-alkynyl, C$_3$-C$_8$-cycloalkyl, aryl, aralkyl, 4-, 5- or 6-membered heterocyclyl, —C$_1$-C$_6$-alkyl-Si(C$_1$-C$_6$-alkyl)$_3$ and —C$_1$-C$_6$-alkyl-C$_3$-C$_8$-cycloalkyl;

U$^{4a}$ is a chlorine atom or a bromine atom; and

U$^5$ is a chlorine atom or a bromine atom.

Compounds of formula (Xa) and (Xb) are provided:

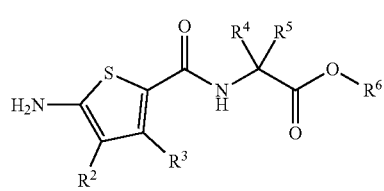
(Xa)

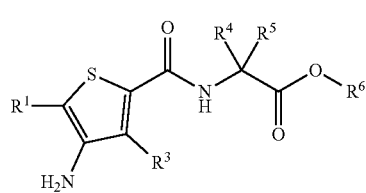
(Xb)

R$^1$ or R$^2$ is a chlorine atom or a bromine atom;

R$^3$ is methyl;

R$^4$ is selected from the group consisting of hydrogen atom, C$_1$-C$_6$-alkyl, aralkyl, aralkyl substituted by hydroxyl, C$_1$-C$_6$-alkyl substituted by a C$_1$-C$_6$-alkylsulfanyl and R$^5$ is a hydrogen atom; or R$^4$ and R$^5$ form, together with the carbon atom to which they are linked, a cyclopropyl;

R$^6$ is selected from the group consisting of hydrogen atom, C$_1$-C$_6$-alkyl, C$_1$-C$_6$-haloalkyl, C$_1$-C$_6$-cyanoalkyl, C$_2$-C$_6$-alkenyl, C$_2$-C$_6$-alkynyl, C$_3$-C$_8$-cycloalkyl, aryl, aralkyl, 4-, 5- or 6-membered heterocyclyl, —C$_1$-C$_6$-alkyl-Si(C$_1$-C$_6$-alkyl)$_3$ and —C$_1$-C$_6$-alkyl-C$_3$-C$_8$-cycloalkyl;

wherein R$^4$ is selected from the group consisting of hydrogen atom, C$_1$-C$_6$-alkyl, aralkyl, aralkyl substituted by hydroxyl, C$_1$-C$_6$-alkyl substituted by a C$_1$-C$_6$-alkylsulfanyl and R$^5$ is a hydrogen atom when R$^6$ is hydrogen atom or C$_1$-C$_6$-alkyl.

Compounds of formula (XIa) and (XIb) are provided:

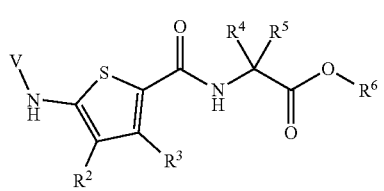
(XIa)

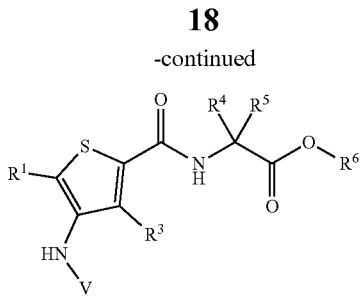
(XIb)

wherein

R$^1$ or R$^2$ is a chlorine atom or a bromine atom;

R$^3$ is methyl;

R$^4$ is selected from the group consisting of hydrogen atom, C$_1$-C$_6$-alkyl, aralkyl, aralkyl substituted by hydroxyl, C$_1$-C$_6$-alkyl substituted by a C$_1$-C$_6$-alkylsulfanyl and R$^5$ is a hydrogen atom; or R$^4$ and R$^5$ form, together with the carbon atom to which they are linked, a cyclopropyl;

R$^6$ is selected from the group consisting of hydrogen atom, C$_1$-C$_6$-alkyl, C$_1$-C$_6$-haloalkyl, C$_1$-C$_6$-cyanoalkyl, C$_2$-C$_6$-alkenyl, C$_2$-C$_6$-alkynyl, C$_3$-C$_8$-cycloalkyl, aryl, aralkyl, 4-, 5- or 6-membered heterocyclyl, —C$_1$-C$_6$-alkyl-Si(C$_1$-C$_6$-alkyl)$_3$ and —C$_1$-C$_6$-alkyl-C$_3$-C$_8$-cycloalkyl;

V is a benzyl group, a 4-methoxybenzyl group, an allyl group, an unsubstituted or substituted C$_1$-C$_6$-alkoxycarbonyl, an unsubstituted or substituted benzyloxycarbonyl, an allyloxycarbonyl, an acetyl group or a trifluoroacetyl group;

wherein R$^4$ is selected from the group consisting of hydrogen atom, C$_1$-C$_6$-alkyl, aralkyl, aralkyl substituted by hydroxyl, C$_1$-C$_6$-alkyl substituted by a C$_1$-C$_6$-alkylsulfanyl and R$^5$ is a hydrogen atom when R$^6$ is hydrogen atom or C$_1$-C$_6$-alkyl.

Compounds of formula (XIIa) and (XIIb) are provided:

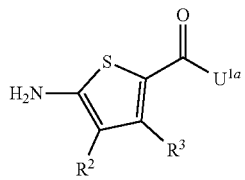
(XIIa)

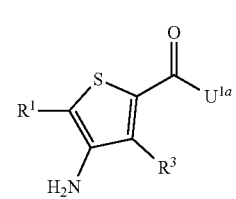
(XIIb)

wherein

R$^1$ or R$^2$ is a chlorine atom or a bromine atom;

R$^3$ is methyl;

U$^{1a}$ is a hydroxy group or a C$_1$-C$_6$-alkoxy group.

provided that the compound of formula (XIIa) does not represent:

ethyl 5-amino-4-bromo-3-methylthiophene-2-carboxylate [851443-15-7].

Compounds of formula (XIIIa) and (XIIIb) are provided:

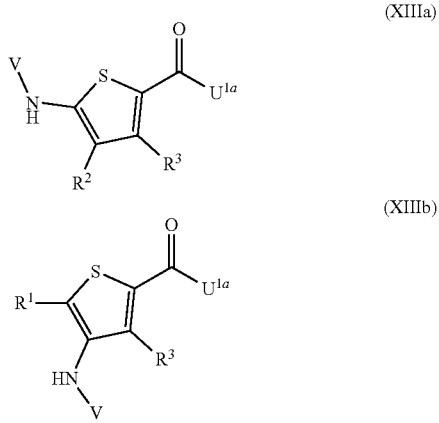

wherein
$R^1$ or $R^2$ is a chlorine atom or a bromine atom;
$R^3$ is methyl;
V is a benzyl group, a 4-methoxybenzyl group, an allyl group, an unsubstituted or substituted $C_1$-$C_6$-alkoxycarbonyl, an unsubstituted or substituted benzyloxycarbonyl, an allyloxycarbonyl, an acetyl group or a trifluoroacetyl group; and
$U^{1a}$ is a hydroxy group or a $C_1$-$C_6$-alkoxy group,
provided that the compound of formula (XIIIa) does not represent:
ethyl 5-acetamido-4-bromo-3-methylthiophene-2-carboxylate [851444-63-8].

The disclosed intermediates may be efficient in controlling bacteria and/or fungi.

Compositions and Formulations

The present invention further relates to a composition, in particular a composition for controlling plant diseases caused by bacteria of the genus *Xanthomonas* comprising one or more compounds of formula (I) as disclosed herein above and any mixtures thereof.

The composition typically comprises at least one compound of formula (I) and at least one agriculturally suitable auxiliary, e.g. carrier(s) and/or surfactant(s).

A carrier is a solid or liquid, natural or synthetic, organic or inorganic substance that is generally inert. The carrier generally improves the application of the compounds, for instance, to plants, plants parts or seeds. Examples of suitable solid carriers include, but are not limited to, ammonium salts, natural rock flours, such as kaolins, clays, talc, chalk, quartz, attapulgite, montmorillonite and diatomaceous earth, and synthetic rock flours, such as finely divided silica, alumina and silicates. Examples of typically useful solid carriers for preparing granules include, but are not limited to crushed and fractionated natural rocks such as calcite, marble, pumice, sepiolite and dolomite, synthetic granules of inorganic and organic flours and granules of organic material such as paper, sawdust, coconut shells, maize cobs and tobacco stalks. Examples of suitable liquid carriers include, but are not limited to, water, organic solvents and combinations thereof. Examples of suitable solvents include polar and nonpolar organic chemical liquids, for example from the classes of aromatic and nonaromatic hydrocarbons (such as cyclohexane, paraffins, alkylbenzenes, xylene, toluene alkylnaphthalenes, chlorinated aromatics or chlorinated aliphatic hydrocarbons such as chlorobenzenes, chloroethylenes or methylene chloride), alcohols and polyols (which may optionally also be substituted, etherified and/or esterified, such as butanol or glycol), ketones (such as acetone, methyl ethyl ketone, methyl isobutyl ketone or cyclohexanone), esters (including fats and oils) and (poly)ethers, unsubstituted and substituted amines, amides (such as dimethylformamide), lactams (such as N-alkylpyrrolidones) and lactones, sulfones and sulfoxides (such as dimethyl sulfoxide). The carrier may also be a liquefied gaseous extender, i.e. liquid which is gaseous at standard temperature and under standard pressure, for example aerosol propellants such as halohydrocarbons, butane, propane, nitrogen and carbon dioxide. The amount of carrier typically ranges from 1 to 99.99%, preferably from 5 to 99.9%, more preferably from 10 to 99.5%, and most preferably from 20 to 99% by weight of the composition.

The surfactant can be an ionic (cationic or anionic) or non-ionic surfactant, such as ionic or non-ionic emulsifier(s), foam former(s), dispersant(s), wetting agent(s) and any mixtures thereof. Examples of suitable surfactants include, but are not limited to, salts of polyacrylic acid, salts of lignosulfonic acid, salts of phenolsulfonic acid or naphthalenesulfonic acid, polycondensates of ethylene and/or propylene oxide with fatty alcohols, fatty acids or fatty amines (polyoxyethylene fatty acid esters, polyoxyethylene fatty alcohol ethers, for example alkylaryl polyglycol ethers), substituted phenols (preferably alkylphenols or arylphenols), salts of sulfosuccinic esters, taurine derivatives (preferably alkyl taurates), phosphoric esters of polyethoxylated alcohols or phenols, fatty esters of polyols and derivatives of compounds containing sulfates, sulfonates, phosphates (for example, alkylsulfonates, alkyl sulfates, arylsulfonates) and protein hydrolysates, lignosulfite waste liquors and methylcellulose. A surfactant is typically used when the compounds of the invention and/or the carrier are insoluble in water and the application is made with water. Then, the amount of surfactants typically ranges from 5 to 40% by weight of the composition.

Further examples of suitable auxiliaries include water repellents, siccatives, binders (adhesive, tackifier, fixing agent, such as carboxymethylcellulose, natural and synthetic polymers in the form of powders, granules or latices, such as gum arabic, polyvinyl alcohol and polyvinyl acetate, natural phospholipids such as cephalins and lecithins and synthetic phospholipids, polyvinylpyrrolidone and tylose), thickeners, stabilizers (e.g. cold stabilizers, preservatives, antioxidants, light stabilizers, or other agents which improve chemical and/or physical stability), dyes or pigments (such as inorganic pigments, e.g. iron oxide, titanium oxide and Prussian Blue; organic dyes, e.g. alizarin, azo and metal phthalocyanine dyes), antifoams (e.g. silicone antifoams and magnesium stearate), preservatives (e.g. dichlorophene and benzyl alcohol hemiformal), secondary thickeners (cellulose derivatives, acrylic acid derivatives, xanthan, modified clays and finely divided silica), stickers, gibberellins and processing auxiliaries, mineral and vegetable oils, perfumes, waxes, nutrients (including trace nutrients, such as salts of iron, manganese, boron, copper, cobalt, molybdenum and zinc), protective colloids, thixotropic substances, penetrants, sequestering agents and complex formers.

The choice of the auxiliaries is related to the intended mode of application of the compound of the invention and/or on the physical properties. Furthermore, the auxiliaries may be chosen to impart particular properties (technical, physical and/or biological properties) to the compositions or use forms prepared therefrom. The choice of auxiliaries may allow customizing the compositions to specific needs.

The composition of the invention may be in any customary form, such as solutions (e.g. aqueous solutions), emulsions, wettable powders, water- and oil-based suspensions, powders, dusts, pastes, soluble powders, soluble granules, granules for broadcasting, suspoemulsion concentrates, natural or synthetic products impregnated with the compound(s) of the invention, fertilizers and also microencapsulations in polymeric substances. The compound(s) of the invention may be present in a suspended, emulsified or dissolved form.

The composition of the invention may be provided to the end user as ready-for-use formulation, i.e. the compositions may be directly applied to the plants or seeds by a suitable device, such as a spraying or dusting device. Alternatively, the compositions may be provided to the end user in the form of concentrates which have to be diluted, preferably with water, prior to use.

The composition of the invention can be prepared in conventional manners, for example by mixing the compound(s) of the invention with one or more suitable auxiliaries, such as disclosed herein above.

The composition according to the invention contains generally from 0.01 to 99% by weight, from 0.05 to 98% by weight, preferably from 0.1 to 95% by weight, more preferably from 0.5 to 90% by weight, most preferably from 1 to 80% by weight of the compound(s) of the invention. It is possible that a composition comprises two or more compounds of the invention. In such case the outlined ranges refer to the total amount of compounds of the present invention.

Mixtures/Combinations

The compound(s) and the composition of the invention can be mixed with other active ingredients like fungicides, bactericides, acaricides, nematicides, insecticides, herbicides, fertilizers, growth regulators, safeners and/or semiochemicals. This may allow to broaden the activity spectrum or to prevent development of resistance. Examples of known fungicides, insecticides, acaricides, nematicides and bactericides are disclosed in the Pesticide Manual, 17$^{th}$ Edition.

Examples of especially preferred fungicides which could be mixed with the compound(s) and the composition of the invention are:

1) Inhibitors of the ergosterol biosynthesis, for example (1.001) cyproconazole, (1.002) difenoconazole, (1.003) epoxiconazole, (1.004) fenhexamid, (1.005) fenpropidin, (1.006) fenpropimorph, (1.007) fenpyrazamine, (1.008) fluquinconazole, (1.009) flutriafol, (1.010) imazalil, (1.011) imazalil sulfate, (1.012) ipconazole, (1.013) metconazole, (1.014) myclobutanil, (1.015) paclobutrazol, (1.016) prochloraz, (1.017) propiconazole, (1.018) prothioconazole, (1.019) pyrisoxazole, (1.020) spiroxamine, (1.021) tebuconazole, (1.022) tetraconazole, (1.023) triadimenol, (1.024) tridemorph, (1.025) triticonazole, (1.026) (1R,2S,5S)-5-(4-chlorobenzyl)-2-(chloromethyl)-2-methyl-1-(1H-1,2,4-triazol-1-ylmethyl)cyclopentanol, (1.027) (1S,2R,5R)-5-(4-chlorobenzyl)-2-(chloromethyl)-2-methyl-1-(1H-1,2,4-triazol-1-ylmethyl)cyclopentanol, (1.028) (2R)-2-(1-chlorocyclopropyl)-4-[(1R)-2,2-dichlorocyclopropyl]-1-(1H-1,2,4-triazol-1-yl)butan-2-ol, (1.029) (2R)-2-(1-chlorocyclopropyl)-4-[(1 S)-2,2-dichlorocyclopropyl]-1-(1H-1,2,4-triazol-1-yl)butan-2-ol, (1.030) (2R)-2-[4-(4-chlorophenoxy)-2-(trifluoromethyl)phenyl]-1-(1H-1,2,4-triazol-1-yl)propan-2-ol, (1.031) (2S)-2-(1-chlorocyclopropyl)-4-[(1R)-2,2-dichlorocyclopropyl]-1-(1H-1,2,4-triazol-1-yl)butan-2-ol, (1.032) (2S)-2-(1-chlorocyclopropyl)-4-[(1 S)-2,2-dichlorocyclopropyl]-1-(1H-1,2,4-triazol-1-yl)butan-2-ol, (1.033) (2S)-2-[4-(4-chlorophenoxy)-2-(trifluoromethyl)phenyl]-1-(1H-1,2,4-triazol-1-yl)propan-2-ol, (1.034) (R)-[3-(4-chloro-2-fluorophenyl)-5-(2,4-difluorophenyl)-1,2-oxazol-4-yl](pyridin-3-yl)methanol, (1.035) (S)-[3-(4-chloro-2-fluorophenyl)-5-(2,4-difluorophenyl)-1,2-oxazol-4-yl](pyridin-3-yl)methanol, (1.036) [3-(4-chloro-2-fluorophenyl)-5-(2,4-difluorophenyl)-1,2-oxazol-4-yl](pyridin-3-yl)methanol, (1.037) 1-({(2R,4S)-2-[2-chloro-4-(4-chlorophenoxy)phenyl]-4-methyl-1,3-dioxolan-2-yl}methyl)-1H-1,2,4-triazole, (1.038) 1-({(2S,4S)-2-[2-chloro-4-(4-chlorophenoxy)phenyl]-4-methyl-1,3-dioxolan-2-yl}methyl)-1H-1,2,4-triazole, (1.039) 1-{[3-(2-chlorophenyl)-2-(2,4-difluorophenyl)oxiran-2-yl]methyl}-1H-1,2,4-triazol-5-yl thiocyanate, (1.040) 1-{[rel(2R,3R)-3-(2-chlorophenyl)-2-(2,4-difluorophenyl)oxiran-2-yl]methyl}-1H-1,2,4-triazol-5-yl thiocyanate, (1.041) 1-{[rel(2R,3S)-3-(2-chlorophenyl)-2-(2,4-difluorophenyl)oxiran-2-yl]methyl}-1H-1,2,4-triazol-5-yl thiocyanate, (1.042) 2-[(2R,4R,5R)-1-(2,4-dichlorophenyl)-5-hydroxy-2,6,6-trimethylheptan-4-yl]-2,4-dihydro-3H-1,2,4-triazole-3-thione, (1.043) 2-[(2R,4R,5S)-1-(2,4-dichlorophenyl)-5-hydroxy-2,6,6-trimethylheptan-4-yl]-2,4-dihydro-3H-1,2,4-triazole-3-thione, (1.044) 2-[(2R,4S,5R)-1-(2,4-dichlorophenyl)-5-hydroxy-2,6,6-trimethylheptan-4-yl]-2,4-dihydro-3H-1,2,4-triazole-3-thione, (1.045) 2-[(2R,4S,5S)-1-(2,4-dichlorophenyl)-5-hydroxy-2,6,6-trimethylheptan-4-yl]-2,4-dihydro-3H-1,2,4-triazole-3-thione, (1.046) 2-[(2S,4R,5R)-1-(2,4-dichlorophenyl)-5-hydroxy-2,6,6-trimethylheptan-4-yl]-2,4-dihydro-3H-1,2,4-triazole-3-thione, (1.047) 2-[(2S,4R,5S)-1-(2,4-dichlorophenyl)-5-hydroxy-2,6,6-trimethylheptan-4-yl]-2,4-dihydro-3H-1,2,4-triazole-3-thione, (1.048) 2-[(2S,4S,5R)-1-(2,4-dichlorophenyl)-5-hydroxy-2,6,6-trimethylheptan-4-yl]-2,4-dihydro-3H-1,2,4-triazole-3-thione, (1.049) 2-[(2S,4S,5S)-1-(2,4-dichlorophenyl)-5-hydroxy-2,6,6-trimethylheptan-4-yl]-2,4-dihydro-3H-1,2,4-triazole-3-thione, (1.050) 2-[1-(2,4-dichlorophenyl)-5-hydroxy-2,6,6-trimethylheptan-4-yl]-2,4-dihydro-3H-1,2,4-triazole-3-thione, (1.051) 2-[2-chloro-4-(2,4-dichlorophenoxy)phenyl]-1-(1H-1,2,4-triazol-1-yl)propan-2-ol, (1.052) 2-[2-chloro-4-(4-chlorophenoxy)phenyl]-1-(1H-1,2,4-triazol-1-yl)butan-2-ol, (1.053) 2-[4-(4-chlorophenoxy)-2-(trifluoromethyl)phenyl]-1-(1H-1,2,4-triazol-1-yl)butan-2-ol, (1.054) 2-[4-(4-chlorophenoxy)-2-(trifluoromethyl)phenyl]-1-(1H-1,2,4-triazol-1-yl)pentan-2-ol, (1.055) Mefentrifluconazole, (1.056) 2-{[3-(2-chlorophenyl)-2-(2,4-difluorophenyl)oxiran-2-yl]methyl}-2,4-dihydro-3H-1,2,4-triazole-3-thione, (1.057) 2-{[rel(2R,3R)-3-(2-chlorophenyl)-2-(2,4-difluorophenyl)oxiran-2-yl]methyl}-2,4-dihydro-3H-1,2,4-triazole-3-thione, (1.058) 2-{[rel(2R,3S)-3-(2-chlorophenyl)-2-(2,4-difluorophenyl)oxiran-2-yl]methyl}-2,4-dihydro-3H-1,2,4-triazole-3-thione, (1.059) 5-(4-chlorobenzyl)-2-(chloromethyl)-2-methyl-1-(1H-1,2,4-triazol-1-ylmethyl)cyclopentanol, (1.060) 5-(allylsulfanyl)-1-{[3-(2-chlorophenyl)-2-(2,4-difluorophenyl)oxiran-2-yl]methyl}-1H-1,2,4-triazole, (1.061) 5-(allylsulfanyl)-1-{[rel(2R,3R)-3-(2-chlorophenyl)-2-(2,4-difluorophenyl)oxiran-2-yl]methyl}-1H-1,2,4-triazole, (1.062) 5-(allylsulfanyl)-1-{[rel(2R,3S)-3-(2-chlorophenyl)-2-(2,4-difluorophenyl)oxiran-2-yl]methyl}-1H-1,2,4-triazole, (1.063) N'-(2,5-dimethyl-4-{[3-(1,1,2,2-tetrafluoroethoxy)phenyl]sulfanyl}phenyl)-N-ethyl-N-methylimidoformamide, (1.064) N'-(2,5-dimethyl-4-{[3-(2,2,2-trifluoroethoxy)phenyl]sulfanyl}phenyl)-N-ethyl-N-methylimidoformamide, (1.065) N'-(2,5-dimethyl-4-{[3-(2,2,3,3-tetrafluoropropoxy)phenyl]sulfanyl}phenyl)-N-ethyl-N-methylimidoformamide, (1.066) N'-(2,5-dimethyl-4-{[3-

(pentafluoroethoxy)phenyl]sulfanyl}phenyl)-N-ethyl-N-methylimidoformamide, (1.067) N'-(2,5-dimethyl-4-{3-[(1,1,2,2-tetrafluoroethyl)sulfanyl]phenoxy}phenyl)-N-ethyl-N-methylimidoformamide, (1.068) N'-(2,5-dimethyl-4-{3-[(2,2,2-trifluoroethyl)sulfanyl]phenoxy}phenyl)-N-ethyl-N-methylimido-formamide, (1.069) N'-(2,5-dimethyl-4-{3-[(2,2,3,3-tetrafluoropropyl)sulfanyl]phenoxy}phenyl)-N-ethyl-N-methylimidoformamide, (1.070) N'-(2,5-dimethyl-4-{3-[(pentafluoroethyl)sulfanyl]phenoxy}phenyl)-N-ethyl-N-methylimidoformamide, (1.071) N'-(2,5-dimethyl-4-phenoxyphenyl)-N-ethyl-N-methylimidoformamide, (1.072) N'-(4-{[3-(difluoromethoxy)phenyl]sulfanyl}-2,5-dimethylphenyl)-N-ethyl-N-methylimidoformamide, (1.073) N'-(4-{3-[(difluoromethyl)sulfanyl]phenoxy}-2,5-dimethylphenyl)-N-ethyl-N-methylimidoformamide, (1.074) N'-[5-bromo-6-(2,3-dihydro-1H-inden-2-yloxy)-2-methylpyridin-3-yl]-N-ethyl-N-methylimidoformamide, (1.075) N'-{4-[(4,5-dichloro-1,3-thiazol-2-yl)oxy]-2,5-dimethylphenyl}-N-ethyl-N-methylimidoformamide, (1.076) N'-{5-bromo-6-[(1R)-1-(3,5-difluorophenyl)ethoxy]-2-methylpyridin-3-yl}-N-ethyl-N-methylimidoformamide, (1.077) N'-{5-bromo-6-[(1 S)-1-(3,5-difluorophenyl)ethoxy]-2-methylpyridin-3-yl}-N-ethyl-N-methylimidoformamide, (1.078) N'-{5-bromo-6-[(cis-4-isopropylcyclohexyl)oxy]-2-methylpyridin-3-yl}-N-ethyl-N-methylimidoformamide, (1.079) N'-{5-bromo-6-[(trans-4-isopropylcyclohexyl)oxy]-2-methylpyridin-3-yl}-N-ethyl-N-methylimidoformamide, (1.080) N'-{5-bromo-6-[1-(3,5-difluorophenyl)ethoxy]-2-methylpyridin-3-yl}-N-ethyl-N-methylimidoformamide, (1.081) Ipfentrifluconazole.

2) Inhibitors of the respiratory chain at complex I or II, for example (2.001) benzovindiflupyr, (2.002) bixafen, (2.003) boscalid, (2.004) carboxin, (2.005) fluopyram, (2.006) flutolanil, (2.007) fluxapyroxad, (2.008) furametpyr, (2.009) Isofetamid, (2.010) isopyrazam (anti-epimeric enantiomer 1R,4S,9S), (2.011) isopyrazam (anti-epimeric enantiomer 1S,4R,9R), (2.012) isopyrazam (anti-epimeric racemate 1RS,4SR,9SR), (2.013) isopyrazam (mixture of syn-epimeric racemate 1RS,4SR,9RS and anti-epimeric racemate 1RS,4SR,9SR), (2.014) isopyrazam (syn-epimeric enantiomer 1R,4S,9R), (2.015) isopyrazam (syn-epimeric enantiomer 1S,4R,9S), (2.016) isopyrazam (syn-epimeric racemate 1RS,4SR,9RS), (2.017) penflufen, (2.018) penthiopyrad, (2.019) pydiflumetofen, (2.020) pyraziflumid, (2.021) sedaxane, (2.022) 1,3-dimethyl-N-(1,1,3-trimethyl-2,3-dihydro-1H-inden-4-yl)-1H-pyrazole-4-carboxamide, (2.023) 1,3-dimethyl-N-[(3R)-1,1,3-trimethyl-2,3-dihydro-1H-inden-4-yl]-1H-pyrazole-4-carboxamide, (2.024) 1,3-dimethyl-N-[(3S)-1,1,3-trimethyl-2,3-dihydro-1H-inden-4-yl]-1H-pyrazole-4-carboxamide, (2.025) 1-methyl-3-(trifluoromethyl)-N-[2'-(trifluoromethyl)biphenyl-2-yl]-1H-pyrazole-4-carboxamide, (2.026) 2-fluoro-6-(trifluoromethyl)-N-(1,1,3-trimethyl-2,3-dihydro-1H-inden-4-yl)benzamide, (2.027) 3-(difluoromethyl)-1-methyl-N-(1,1,3-trimethyl-2,3-dihydro-1H-inden-4-yl)-1H-pyrazole-4-carboxamide, (2.028) 3-(difluoromethyl)-1-methyl-N-[(3R)-1,1,3-trimethyl-2,3-dihydro-1H-inden-4-yl]-1H-pyrazole-4-carboxamide, (2.029) 3-(difluoromethyl)-1-methyl-N-[(3S)-1,1,3-trimethyl-2,3-dihydro-1H-inden-4-yl]-1H-pyrazole-4-carboxamide, (2.030) fluindapyr, (2.031) 3-(difluoromethyl)-N-[(3R)-7-fluoro-1,1,3-trimethyl-2,3-dihydro-1H-inden-4-yl]-1-methyl-1H-pyrazole-4-carboxamide, (2.032) 3-(difluoromethyl)-N-[(3S)-7-fluoro-1,1,3-trimethyl-2,3-dihydro-1H-inden-4-yl]-1-methyl-1H-pyrazole-4-carboxamide, (2.033) 5,8-difluoro-N-[2-(2-fluoro-4-{[4-(trifluoromethyl)pyridin-2-yl]oxy}-phenyl)ethyl]quinazolin-4-amine, (2.034) N-(2-cyclopentyl-5-fluorobenzyl)-N-cyclopropyl-3-(difluoromethyl)-5-fluoro-1-methyl-1H-pyrazole-4-carboxamide, (2.035) N-(2-tert-butyl-5-methylbenzyl)-N-cyclopropyl-3-(difluoromethyl)-5-fluoro-1-methyl-1H-pyrazole-4-carboxamide, (2.036) N-(2-tert-butylbenzyl)-N-cyclopropyl-3-(difluoromethyl)-5-fluoro-1-methyl-1H-pyrazole-4-carboxamide, (2.037) N-(5-chloro-2-ethylbenzyl)-N-cyclopropyl-3-(difluoromethyl)-5-fluoro-1-methyl-1H-pyrazole-4-carboxamide, (2.038) isoflucypram, (2.039) N-[(1R,4S)-9-(dichloromethylene)-1,2,3,4-tetrahydro-1,4-methanonaphthalen-5-yl]-3-(difluoromethyl)-1-methyl-1H-pyrazole-4-carboxamide, (2.040) N-[(1S,4R)-9-(dichloromethylene)-1,2,3,4-tetrahydro-1,4-methanonaphthalen-5-yl]-3-(difluoromethyl)-1-methyl-1H-pyrazole-4-carboxamide, (2.041) N-[1-(2,4-dichlorophenyl)-1-methoxypropan-2-yl]-3-(difluoromethyl)-1-methyl-1H-pyrazole-4-carboxamide, (2.042) N-[2-chloro-6-(trifluoromethyl)benzyl]-N-cyclopropyl-3-(difluoromethyl)-5-fluoro-1-methyl-1H-pyrazole-4-carboxamide, (2.043) N-[3-chloro-2-fluoro-6-(trifluoromethyl)benzyl]-N-cyclopropyl-3-(difluoromethyl)-5-fluoro-1-methyl-1H-pyrazole-4-carboxamide, (2.044) N-[5-chloro-2-(trifluoromethyl)benzyl]-N-cyclopropyl-3-(difluoromethyl)-5-fluoro-1-methyl-1H-pyrazole-4-carboxamide, (2.045) N-cyclopropyl-3-(difluoromethyl)-5-fluoro-1-methyl-N-[5-methyl-2-(trifluoromethyl)benzyl]-1H-pyrazole-4-carboxamide, (2.046) N-cyclopropyl-3-(difluoromethyl)-5-fluoro-N-(2-fluoro-6-isopropylbenzyl)-1-methyl-1H-pyrazole-4-carboxamide, (2.047) N-cyclopropyl-3-(difluoromethyl)-5-fluoro-N-(2-isopropyl-5-methylbenzyl)-1-methyl-1H-pyrazole-4-carboxamide, (2.048) N-cyclopropyl-3-(difluoromethyl)-5-fluoro-N-(2-isopropylbenzyl)-1-methyl-1H-pyrazole-4-carbothioamide, (2.049) N-cyclopropyl-3-(difluoromethyl)-5-fluoro-N-(2-isopropylbenzyl)-1-methyl-1H-pyrazole-4-carboxamide, (2.050) N-cyclopropyl-3-(difluoromethyl)-5-fluoro-N-(5-fluoro-2-isopropylbenzyl)-1-methyl-1H-pyrazole-4-carboxamide, (2.051) N-cyclopropyl-3-(difluoromethyl)-N-(2-ethyl-4,5-dimethylbenzyl)-5-fluoro-1-methyl-1H-pyrazole-4-carboxamide, (2.052) N-cyclopropyl-3-(difluoromethyl)-N-(2-ethyl-5-fluorobenzyl)-5-fluoro-1-methyl-1H-pyrazole-4-carboxamide, (2.053) N-cyclopropyl-3-(difluoromethyl)-N-(2-ethyl-5-methylbenzyl)-5-fluoro-1-methyl-1H-pyrazole-4-carboxamide, (2.054) N-cyclopropyl-N-(2-cyclopropyl-5-fluorobenzyl)-3-(difluoromethyl)-5-fluoro-1-methyl-1H-pyrazole-4-carboxamide, (2.055) N-cyclopropyl-N-(2-cyclopropyl-5-methylbenzyl)-3-(difluoromethyl)-5-fluoro-1-methyl-1H-pyrazole-4-carboxamide, (2.056) N-cyclopropyl-N-(2-cyclopropylbenzyl)-3-(difluoromethyl)-5-fluoro-1-methyl-1H-pyrazole-4-carboxamide, (2.057) pyrapropoyne.

3) Inhibitors of the respiratory chain at complex III, for example (3.001) ametoctradin, (3.002) amisulbrom, (3.003) azoxystrobin, (3.004) coumethoxystrobin, (3.005) coumoxystrobin, (3.006) cyazofamid, (3.007) dimoxystrobin, (3.008) enoxastrobin, (3.009) famoxadone, (3.010) fenamidone, (3.011) flufenoxystrobin, (3.012) fluoxastrobin, (3.013) kresoxim-methyl, (3.014) metominostrobin, (3.015) orysastrobin, (3.016) picoxystrobin, (3.017) pyraclostrobin, (3.018) pyrametostrobin, (3.019) pyraoxystrobin, (3.020) trifloxystrobin, (3.021) (2E)-2-{2-[({[(1E)-1-(3-{[(E)-1-fluoro-2-phenylvinyl]oxy}phenyl)ethylidene]amino}oxy)methyl]phenyl}-2-(methoxyimino)-N-methylacetamide, (3.022) (2E,3Z)-5-{[1-(4-chlorophenyl)-1H-pyrazol-3-yl]oxy}-2-(methoxyimino)-N,3-dimethylpent-3-enamide, (3.023) (2R)-2-{2-[(2,5-dimethylphenoxy)methyl]phenyl}-2-methoxy-N-methylacetamide, (3.024) (2S)-2-{2-[(2,5-dimethylphenoxy)methyl]phenyl}-2-methoxy-N-methylacetamide, (3.025) (3S,6S,7R,8R)-8-benzyl-3-[({3-[(isobutyryloxy)methoxy]-4-methoxypyridin-2-yl}carbonyl)amino]-6-methyl-4,9-dioxo-1,5-dioxonan-7-yl 2-methylpropanoate, (3.026) mandestrobin, (3.027) N-(3-ethyl-3,5,5-trimethylcyclohexyl)-3-formamido-2-hydroxybenzamide, (3.028) (2E,3Z)-5-{[1-(4-chloro-2-fluorophenyl)-1H-pyrazol-3-yl]oxy}-2-(methoxyimino)-N,3-dimethylpent-3-enamide, (3.029) methyl {5-[3-(2,4-dimethylphenyl)-1H-pyrazol-1-yl]-2-methylbenzyl}carbamate, (3.030) metyltetraprole, (3.031) florylpicoxamid.

4) Inhibitors of the mitosis and cell division, for example (4.001) carbendazim, (4.002) diethofencarb, (4.003) ethaboxam, (4.004) fluopicolide, (4.005) pencycuron, (4.006) thiabendazole, (4.007) thiophanate-methyl, (4.008) zoxamide, (4.009) 3-chloro-4-(2,6-difluorophenyl)-6-methyl-5-phenylpyridazine, (4.010) 3-chloro-5-(4-chlorophenyl)-4-(2,6-difluorophenyl)-6-methylpyridazine, (4.011) 3-chloro-5-(6-chloropyridin-3-yl)-6-methyl-4-(2,4,6-trifluorophenyl)pyridazine, (4.012) 4-(2-bromo-4-fluorophenyl)-N-(2,6-difluorophenyl)-1,3-dimethyl-1H-pyrazol-5-amine, (4.013) 4-(2-bromo-4-fluorophenyl)-N-(2-bromo-6-fluorophenyl)-1,3-dimethyl-1H-pyrazol-5-amine, (4.014) 4-(2-bromo-4-fluorophenyl)-N-(2-bromophenyl)-1,3-dimethyl-1H-pyrazol-5-amine, (4.015) 4-(2-bromo-4-fluorophenyl)-N-(2-chloro-6-fluorophenyl)-1,3-dimethyl-1H-pyrazol-5-amine, (4.016) 4-(2-bromo-4-fluorophenyl)-N-(2-chlorophenyl)-1,3-dimethyl-1H-pyrazol-5-amine, (4.017) 4-(2-bromo-4-fluorophenyl)-N-(2-fluorophenyl)-1,3-dimethyl-1H-pyrazol-5-amine, (4.018) 4-(2-chloro-4-fluorophenyl)-N-(2,6-difluorophenyl)-1,3-dimethyl-1H-pyrazol-5-amine, (4.019) 4-(2-chloro-4-fluorophenyl)-N-(2-chloro-6-fluorophenyl)-1,3-dimethyl-1H-pyrazol-5-amine, (4.020) 4-(2-chloro-4-fluorophenyl)-N-(2-chlorophenyl)-1,3-dimethyl-1H-pyrazol-5-amine, (4.021) 4-(2-chloro-4-fluorophenyl)-N-(2-fluorophenyl)-1,3-dimethyl-1H-pyrazol-5-amine, (4.022) 4-(4-chlorophenyl)-5-(2,6-difluorophenyl)-3,6-dimethylpyridazine, (4.023) N-(2-bromo-6-fluorophenyl)-4-(2-chloro-4-fluorophenyl)-1,3-dimethyl-1H-pyrazol-5-amine, (4.024) N-(2-bromophenyl)-4-(2-chloro-4-fluorophenyl)-1,3-dimethyl-1H-pyrazol-5-amine, (4.025) N-(4-chloro-2,6-difluorophenyl)-4-(2-chloro-4-fluorophenyl)-1,3-dimethyl-1H-pyrazol-5-amine.

5) Compounds having a multisite action, for example (5.001) bordeaux mixture, (5.002) captafol, (5.003) captan, (5.004) chlorothalonil, (5.005) copper hydroxide, (5.006) copper naphthenate, (5.007) copper oxide, (5.008) copper oxychloride, (5.009) copper(2+) sulfate, (5.010) dithianon, (5.011) dodine, (5.012) folpet, (5.013) mancozeb, (5.014) maneb, (5.015) metiram, (5.016) metiram zinc, (5.017) oxine-copper, (5.018) propineb, (5.019) sulfur and sulfur preparations including calcium polysulfide, (5.020) thiram, (5.021) zineb, (5.022) ziram, (5.023) 6-ethyl-5,7-dioxo-6,7-dihydro-5H-pyrrolo[3',4':5,6][1,4]dithiino[2,3-c][1,2]thiazole-3-carbonitrile.

6) Compounds inducing a host defense, for example (6.001) acibenzolar-S-methyl, (6.002) isotianil, (6.003) probenazole, (6.004) tiadinil.

7) Inhibitors of the amino acid and/or protein biosynthesis, for example (7.001) cyprodinil, (7.002) kasugamycin, (7.003) kasugamycin hydrochloride hydrate, (7.004) oxytetracycline, (7.005) pyrimethanil, (7.006) 3-(5-fluoro-3,3,4,4-tetramethyl-3,4-dihydroisoquinolin-1-yl)quinoline.

8) Inhibitors of the ATP production, for example (8.001) silthiofam.

9) Inhibitors of the cell wall synthesis, for example (9.001) benthiavalicarb, (9.002) dimethomorph, (9.003) flumorph, (9.004) iprovalicarb, (9.005) mandipropamid, (9.006) pyrimorph, (9.007) valifenalate, (9.008) (2E)-3-(4-tert-butylphenyl)-3-(2-chloropyridin-4-yl)-1-(morpholin-4-yl)prop-2-en-1-one, (9.009) (2Z)-3-(4-tert-butylphenyl)-3-(2-chloropyridin-4-yl)-1-(morpholin-4-yl)prop-2-en-1-one.

10) Inhibitors of the lipid and membrane synthesis, for example (10.001) propamocarb, (10.002) propamocarb hydrochloride, (10.003) tolclofos-methyl.

11) Inhibitors of the melanin biosynthesis, for example (11.001) tricyclazole, (11.002) 2,2,2-trifluoroethyl {3-methyl-1-[(4-methylbenzoyl)amino]butan-2-yl}carbamate.

12) Inhibitors of the nucleic acid synthesis, for example (12.001) benalaxyl, (12.002) benalaxyl-M (kiralaxyl), (12.003) metalaxyl, (12.004) metalaxyl-M (mefenoxam).

13) Inhibitors of the signal transduction, for example (13.001) fludioxonil, (13.002) iprodione, (13.003) procymidone, (13.004) proquinazid, (13.005) quinoxyfen, (13.006) vinclozolin.

14) Compounds acting as an uncoupler, for example (14.001) fluazinam, (14.002) meptyldinocap.

15) Further compounds, for example (15.001) abscisic acid, (15.002) benthiazole, (15.003) bethoxazin, (15.004) capsimycin, (15.005) carvone, (15.006) chinomethionat, (15.007) cufraneb, (15.008) cyflufenamid, (15.009) cymoxanil, (15.010) cyprosulfamide, (15.011) flutianil, (15.012) fosetyl-aluminium, (15.013) fosetyl-calcium, (15.014) fosetyl-sodium, (15.015) methyl isothiocyanate, (15.016) metrafenone, (15.017) mildiomycin, (15.018) natamycin, (15.019) nickel dimethyldithiocarbamate, (15.020) nitrothal-isopropyl, (15.021) oxamocarb, (15.022) oxathiapiprolin, (15.023) oxyfenthiin, (15.024) pentachlorophenol and salts, (15.025) phosphorous acid and its salts, (15.026) propamocarb-fosetylate, (15.027) pyriofenone (chlazafenone), (15.028) tebufloquin, (15.029) tecloftalam, (15.030) tolnifanide, (15.031) 1-(4-{4-[(5R)-5-(2,6-difluorophenyl)-4,5-dihydro-1,2-oxazol-3-yl]-1,3-thiazol-2-yl}piperidin-1-yl)-2-[5-methyl-3-(trifluoromethyl)-1H-pyrazol-1-yl]ethanone, (15.032) 1-(4-{4-[(5S)-5-(2,6-difluorophenyl)-4,5-dihydro-1,2-oxazol-3-yl]-1,3-thiazol-2-yl}piperidin-1-yl)-2-[5-methyl-3-(trifluoromethyl)-1H-pyrazol-1-yl]ethanone, (15.033) 2-(6-benzylpyridin-2-yl)quinazoline, (15.034) dipymetitrone, (15.035) 2-[3,5-bis(difluoromethyl)-1H-pyrazol-1-yl]-1-[4-(4-{5-[2-(prop-2-yn-1-yloxy)phenyl]-4,5-dihydro-1,2-oxazol-3-yl}-1,3-thiazol-2-yl)piperidin-1-yl]ethanone, (15.036) 2-[3,5-bis(difluoromethyl)-1H-pyrazol-1-yl]-1-[4-(4-{5-[2-chloro-6-(prop-2-yn-1-yloxy)phenyl]-4,5-dihydro-1,2-oxazol-3-yl}-1,3-thiazol-2-yl)piperidin-1-yl]ethanone, (15.037) 2-[3,5-bis(difluoromethyl)-1H-pyrazol-1-yl]-1-[4-(4-{5-[2-fluoro-6-(prop-2-yn-1-yloxy)phenyl]-4,5-dihydro-1,2-oxazol-3-yl}-1,3-thiazol-2-yl)piperidin-1-yl]ethanone, (15.038) 2-[6-(3-fluoro-4-methoxyphenyl)-5-methylpyridin-2-yl]quinazoline, (15.039) 2-{(5R)-3-[2-(1-{[3,5-bis(difluoromethyl)-1H-pyrazol-1-yl]acetyl}piperidin-4-yl)-1,3-thiazol-4-yl]-4,5-dihydro-1,2-oxazol-5-yl}-3-chlorophenyl methanesulfonate, (15.040) 2-{(5S)-3-[2-(1-{[3,5-bis(difluoromethyl)-1H-pyrazol-1-yl]acetyl}piperidin-4-yl)-1,3-thiazol-4-yl]-4,5-dihydro-1,2-oxazol-5-yl}-3-chlorophenyl methanesulfonate, (15.041) Ipflufenoquin, (15.042) 2-{2-fluoro-6-[(8-fluoro-2-methylquinolin-3-yl)oxy]phenyl}propan-2-ol, (15.043) 2-{3-[2-(1-{[3,5-bis(difluoromethyl)-1H-pyrazol-1-yl]acetyl}piperidin-4-yl)-1,3-thiazol-4-yl]-4,5-dihydro-1,2-oxazol-5-yl}-3-chlorophenyl methanesulfonate, (15.044) 2-{3-[2-(1-{[3,5-bis(difluoromethyl)-1H-pyrazol-1-yl]acetyl}piperidin-4-yl)-1,3-thiazol- 4-yl]-4,5-dihydro-1,2-oxazol-5-yl}phenyl methanesulfonate, (15.045) 2-phenylphenol and salts, (15.046) 3-(4,4,5-trifluoro-3,3-dimethyl-3,4-dihydroisoquinolin-1-yl)quinoline, (15.047) quinofumelin, (15.048) 4-amino-5-fluoropyrimidin-2-ol (tautomeric form: 4-amino-5-fluoropyrimidin-2(1H)-one), (15.049) 4-oxo-4-[(2-phenylethyl)amino]butanoic acid, (15.050) 5-amino-1,3,4-thiadiazole-2-thiol, (15.051) 5-chloro-N'-phenyl-N'-(prop-2-yn-1-yl)thiophene-2-sulfonohydrazide, (15.052) 5-fluoro-2-[(4-fluorobenzyl)oxy]pyrimidin-4-amine, (15.053) 5-fluoro-2-[(4-methylbenzyl)oxy]pyrimidin-4-amine, (15.054) 9-fluoro-2,2-dimethyl-5-(quinolin-3-yl)-2,3-dihydro-1,4-benzoxazepine, (15.055) but-3-yn-1-yl {6-[({[(Z)-(1-methyl-1H-tetrazol-5-yl)(phenyl)methylene]amino}oxy)methyl]pyridin-2-yl}carbamate, (15.056) ethyl (2Z)-3-amino-2-cyano-3-phenylacrylate, (15.057) phenazine-1-carboxylic acid, (15.058) propyl 3,4,5-trihydroxybenzoate, (15.059) quinolin-8-ol, (15.060) quinolin-8-ol sulfate (2:1), (15.061) tert-butyl {6-[({[(1-methyl-1H-tetrazol-5-yl)(phenyl)methylene]amino}oxy)methyl]pyridin-2-yl}carbamate, (15.062) 5-fluoro-4-imino-3-methyl-1-[(4-methylphenyl)sulfonyl]-3,4-dihydropyrimidin-2(1H)-one, (15.063) aminopyrifen.

All named mixing partners of the classes (1) to (15) as described here above can be present in the form of the free compound and/or, if their functional groups enable this, an agriculturally acceptable salt thereof.

In some embodiments, the compound combinations comprise the following components:
(I.01)+(I.001), (I.01)+(I.002), (I.01)+(I.003), (I.01)+(I.004), (I.01)+(I.005), (I.01)+(I.006), (I.01)+(I.007), (I.01)+(I.008), (I.01)+(I.009), (I.01)+(I.010), (I.01)+(I.011), (I.01)+(I.012), (I.01)+(I.013), (I.01)+(I.014), (I.01)+(I.015), (I.01)+(I.016), (I.01)+(I.017), (I.01)+(I.018), (I.01)+(I.019), (I.01)+(I.020), (I.01)+(I.021), (I.01)+(I.022), (I.01)+(I.023), (I.01)+(I.024), (I.01)+(I.025), (I.01)+(I.026), (I.01)+(I.027), (I.01)+(I.028), (I.01)+(I.029), (I.01)+(I.030), (I.01)+(I.031), (I.01)+(I.032), (I.01)+(I.033), (I.01)+(I.034), (I.01)+(I.035), (I.01)+(I.036), (I.01)+(I.037), (I.01)+(I.038), (I.01)+(I.039), (I.01)+(I.040), (I.01)+(I.041), (I.01)+(I.042), (I.01)+(I.043), (I.01)+(I.044), (I.01)+(I.045), (I.01)+(I.046), (I.01)+(I.047), (I.01)+(I.048), (I.01)+(I.049), (I.01)+(I.050), (I.01)+(I.051), (I.01)+(I.052), (I.01)+(I.053), (I.01)+(I.054), (I.01)+(I.055), (I.01)+(I.056), (I.01)+(I.057), (I.01)+(I.058), (I.01)+(I.059), (I.01)+(I.060), (I.01)+(I.061), (I.01)+(I.062), (I.01)+(I.063), (I.01)+(I.064), (I.01)+(I.065), (I.01)+(I.066), (I.01)+(I.067), (I.01)+(I.068), (I.01)+(I.069), (I.01)+(I.070), (I.01)+(I.071), (I.01)+(I.072), (I.01)+(I.073), (I.01)+(I.074), (I.01)+(I.075), (I.01)+(I.076), (I.01)+(I.077), (I.01)+(I.078), (I.01)+(I.079), (I.01)+(I.080), (I.01)+(I.081), (I.01)+(I.082), (I.01)+(I.083), (I.01)+(I.084), (I.01)+(I.085), (I.01)+(I.086), (I.01)+(2.001), (I.01)+(2.002), (I.01)+(2.003), (I.01)+(2.004), (I.01)+(2.005), (I.01)+(2.006), (I.01)+(2.007), (I.01)+(2.008), (I.01)+(2.009), (I.01)+(2.010), (I.01)+(2.011), (I.01)+(2.012), (I.01)+(2.013), (I.01)+(2.014), (I.01)+(2.015), (I.01)+(2.016), (I.01)+(2.017), (I.01)+(2.018), (I.01)+(2.019), (I.01)+(2.020), (I.01)+(2.021), (I.01)+(2.022), (I.01)+(2.023), (I.01)+(2.024), (I.01)+(2.025), (I.01)+(2.026), (I.01)+(2.027), (I.01)+(2.028), (I.01)+(2.029), (I.01)+(2.030), (I.01)+(2.031), (I.01)+(2.032), (I.01)+(2.033), (I.01)+(2.034), (I.01)+(2.035), (I.01)+(2.036), (I.01)+(2.037), (I.01)+(2.038), (I.01)+(2.039), (I.01)+(2.040), (I.01)+(2.041), (I.01)+(2.042), (I.01)+(2.043), (I.01)+(2.044), (I.01)+(2.045), (I.01)+(2.046), (I.01)+(2.047), (I.01)+(2.048), (I.01)+(2.049), (I.01)+(2.050), (I.01)+(2.051), (I.01)+(2.052), (I.01)+(2.053), (I.01)+(2.054), (I.01)+(2.055), (I.01)+(2.056), (I.01)+(3.001), (I.01)+(3.002), (I.01)+(3.003), (I.01)+(3.004), (I.01)+(3.005), (I.01)+(3.006), (I.01)+(3.007), (I.01)+(3.008), (I.01)+(3.009), (I.01)+(3.010), (I.01)+(3.011), (I.01)+(3.012), (I.01)+(3.013), (I.01)+(3.014), (I.01)+(3.015), (I.01)+(3.016), (I.01)+(3.017), (I.01)+(3.018), (I.01)+(3.019), (I.01)+(3.020), (I.01)+(3.021), (I.01)+(3.022), (I.01)+(3.023), (I.01)+(3.024), (I.01)+(3.025), (I.01)+(3.026), (I.01)+(3.027), (I.01)+(3.028), (I.01)+(3.029), (I.01)+(3.030), (I.01)+(4.001), (I.01)+(4.002), (I.01)+(4.003), (I.01)+(4.004), (I.01)+(4.005), (I.01)+(4.006), (I.01)+(4.007), (I.01)+(4.008), (I.01)+(4.009), (I.01)+(4.010), (I.01)+(4.011), (I.01)+(4.012), (I.01)+(4.013), (I.01)+(4.014), (I.01)+(4.015), (I.01)+(4.016), (I.01)+(4.017), (I.01)+(4.018), (I.01)+(4.019), (I.01)+(4.020), (I.01)+(4.021), (I.01)+(4.022), (I.01)+(4.023), (I.01)+(4.024), (I.01)+(4.025), (I.01)+(5.001), (I.01)+(5.002), (I.01)+(5.003), (I.01)+(5.004), (I.01)+(5.005), (I.01)+(5.006), (I.01)+(5.007), (I.01)+(5.008), (I.01)+(5.009), (I.01)+(5.010), (I.01)+(5.011), (I.01)+(5.012), (I.01)+(5.013), (I.01)+(5.014), (I.01)+(5.015), (I.01)+(5.016), (I.01)+(5.017), (I.01)+(5.018), (I.01)+(5.019), (I.01)+(5.020), (I.01)+(5.021), (I.01)+(5.022), (I.01)+(5.023), (I.01)+(6.001), (I.01)+(6.002), (I.01)+(6.003), (I.01)+(6.004), (I.01)+(7.001), (I.01)+(7.002), (I.01)+(7.003), (I.01)+(7.004), (I.01)+(7.005), (I.01)+(7.006), (I.01)+(8.001), (I.01)+(9.001), (I.01)+(9.002), (I.01)+(9.003), (I.01)+(9.004), (I.01)+(9.005), (I.01)+(9.006), (I.01)+(9.007), (I.01)+(9.008), (I.01)+(9.009), (I.01)+(10.001), (I.01)+(10.002), (I.01)+(10.003), (I.01)+(11.001), (I.01)+(11.002), (I.01)+(12.001), (I.01)+(12.002), (I.01)+(12.003), (I.01)+(12.004), (I.01)+(13.001), (I.01)+(13.002), (I.01)+(13.003), (I.01)+(13.004), (I.01)+(13.005), (I.01)+(13.006), (I.01)+(14.001), (I.01)+(14.002), (I.01)+(15.001), (I.01)+(15.002), (I.01)+(15.003), (I.01)+(15.004), (I.01)+(15.005), (I.01)+(15.006), (I.01)+(15.007), (I.01)+(15.008), (I.01)+(15.009), (I.01)+(15.010), (I.01)+(15.011), (I.01)+(15.012), (I.01)+(15.013), (I.01)+(15.014), (I.01)+(15.015), (I.01)+(15.016), (I.01)+(15.017), (I.01)+(15.018), (I.01)+(15.019), (I.01)+(15.020), (I.01)+(15.021), (I.01)+(15.022), (I.01)+(15.023), (I.01)+(15.024), (I.01)+(15.025), (I.01)+(15.026), (I.01)+(15.027), (I.01)+(15.028), (I.01)+(15.029), (I.01)+(15.030), (I.01)+(15.031), (I.01)+(15.032), (I.01)+(15.033), (I.01)+(15.034), (I.01)+(15.035), (I.01)+(15.036), (I.01)+(15.037), (I.01)+(15.038), (I.01)+(15.039), (I.01)+(15.040), (I.01)+(15.041), (I.01)+(15.042), (I.01)+(15.043), (I.01)+(15.044), (I.01)+(15.045), (I.01)+(15.046), (I.01)+(15.047), (I.01)+(15.048), (I.01)+(15.049), (I.01)+(15.050), (I.01)+(15.051), (I.01)+(15.052), (I.01)+(15.053), (I.01)+(15.054), (I.01)+(15.055), (I.01)+(15.056), (I.01)+(15.057), (I.01)+(15.058), (I.01)+(15.059), (I.01)+(15.060), (I.01)+(15.061), (I.01)+(15.062). (I.01)+(15.063). (I.01)+(15.064). (I.01)+(15.065), (I.01)+15.066), (I.01)+(15.067), (I.01)+(15.068), (I.01)+(15.069), (I.01)+(15.070), (I.01)+(15.071), (I.01)+(15.072), (I.01)+(15.073), (I.01)+(15.074), (I.01)+(15.075), (I.01)+(15.076), (I.01), (I.01)+(15.077), (I.01)+(15.078), (I.01)+(15.079), (I.01)+(15.080), (I.01)+(15.081), (I.01)+(15.082), (I.01)+(15.083), (I.01)+(15.084), (I.01)+(15.085), (I.01)+(15.086), (I.01)+(15.087), (I.01)+(15.088), (I.01)+(15.089), (I.01)+(15.090), (I.01)+(15.091), (I.01)+(15.092), (I.01)+(15.093), (I.01)+(15.094), (I.01)+(15.095), (I.01)+(15.096), (I.01)+(15.097), (I.01)+(15.098), (I.01)+(15.099), (I.01)+(15.100), (I.01)+(15.101), (I.01)+(15.102), (I.01)+(15.103), (I.01)+15.104), (I.01)+(15.105), (I.01)+(15.106), (I.01)+(15.107), (I.01)+(15.108), (I.01)+(15.109), (I.01)+(15.110), (I.01)+(15.111), (I.01)+(15.112).

In these combinations, the first component is a compound of formula (I) as defined in table I.1 (e.g. I.01) and the second component is a fungicide chosen in groups 1 to 15 as defined herein. For instance, the combination (I.01)+(I.001) corresponds to a combination comprising compound I.01 in Table I.1 and cyproconazole (I.001).

In some other embodiments, the compound combinations correspond to the above described combinations wherein compound (I.01) is replaced with any one of the compounds recited in Table I.1.

The compounds of formula (I), and the fungicide selected from groups (1) to (15), can be present in a weight ratio ranging from 100:1 to 1:100 (compound of formula (I): fungicide selected from the groups (1) to (15)), or ranging from 50:1 to 1:50, or ranging from 20:1 to 1:20. Further examples of weight ratio ranges include 95:1 to 1:95, 90:1 to 1:90, 85:1 to 1:85, 80:1 to 1:80, 75:1 to 1:75, 70:1 to 1:70, 65:1 to 1:65, 60:1 to 1:60, 55:1 to 1:55, 45:1 to 1:45, 40:1 to 1:40, 35:1 to 1:35, 30:1 to 1:30, 25:1 to 1:25, 15:1 to 1:15, 10:1 to 1:10, 5:1 to 1:5, 4:1 to 1:4, 3:1 to 1:3, 2:1 to 1:2.

A further fungicide chosen in groups 1 to 15 as defined herein may be added to the compound combinations.

The compound(s) and the composition of the invention may also be combined with one or more biological control agents.

Examples of biological control agents which may be combined with the compound(s) and the composition of the invention are:
(A) Antibacterial agents selected from the group of:
(A1) bacteria, such as (A1.1) *Bacillus subtilis*, in particular strain QST713/AQ713 (available as SERENADE OPTI or SERENADE ASO from Bayer CropScience LP, US, having NRRL Accession No. B21661 and described in U.S. Pat. No. 6,060,051); (A1.2) *Bacillus amyloliquefaciens*, in particular strain D747 (available as Double Nickel™ from Certis, US, having accession number FERM BP-8234 and disclosed in U.S. Pat. No. 7,094,592); (A1.3) *Bacillus pumilus*, in particular strain BU F-33 (having NRRL Accession No. 50185); (A1.4) *Bacillus subtilis* var. *amyloliquefaciens* strain FZB24 (available as Taegro® from Novozymes, US); (A1.5) a *Paenibacillus* sp. strain having Accession No. NRRL B-50972 or Accession No. NRRL B-67129 and described in International Patent Publication No. WO 2016/154297; and
(A2) fungi, such as (A2.1) *Aureobasidium pullulans*, in particular blastospores of strain DSM14940;
(A2.2) *Aureobasidium pullulans* blastospores of strain DSM 14941; (A2.3) *Aureobasidium pullulans*, in particular mixtures of blastospores of strains DSM14940 and DSM14941;
(B) Fungicides selected from the group of:
(B1) bacteria, for example (B1.1) *Bacillus subtilis*, in particular strain QST713/AQ713 (available as SERENADE OPTI or SERENADE ASO from Bayer CropScience LP, US, having NRRL Accession No. B21661 and described in U.S. Pat. No. 6,060,051); (B1.2) *Bacillus pumilus*, in particular strain QST2808 (available as SONATA® from Bayer CropScience LP, US, having Accession No. NRRL B-30087 and described in U.S. Pat. No. 6,245,551); (B1.3) *Bacillus pumilus*, in particular strain GB34 (available as Yield Shield® from Bayer AG, DE); (B1.4) *Bacillus pumilus*, in particular strain BU F-33 (having NRRL Accession No. 50185); (B1.5) *Bacillus amyloliquefaciens*, in particular strain D747 (available as Double Nickel™ from Certis, US, having accession number FERM BP-8234 and disclosed in U.S. Pat. No. 7,094,592); (B1.6) *Bacillus subtilis* Y1336 (available as BIOBAC® WP from Bion-Tech, Taiwan, registered as a biological fungicide in Taiwan under Registration Nos. 4764, 5454, 5096 and 5277); (B1.7) *Bacillus amyloliquefaciens* strain MBI 600 (available as SUBTILEX from BASF SE); (B1.8) *Bacillus subtilis* strain GB03 (available as Kodiak® from Bayer AG, DE); (B1.9) *Bacillus subtilis* var. *amyloliquefaciens* strain FZB24 (available from Novozymes Biologicals Inc., Salem, Va. or Syngenta Crop Protection, LLC, Greensboro, N.C. as the fungicide TAEGRO® or TAEGRO® ECO (EPA Registration No. 70127-5); (B1.10) *Bacillus mycoides*, isolate J (available as BmJ TGAI or WG from Certis USA); (B1.11) *Bacillus licheniformis*, in particular strain SB3086 (available as EcoGuard™ Biofungicide and Green Releaf from Novozymes); (B1.12) a *Paenibacillus* sp. strain having Accession No. NRRL B-50972 or Accession No. NRRL B-67129 and described in International Patent Publication No. WO 2016/154297.

In some embodiments, the biological control agent is a *Bacillus subtilis* or *Bacillus amyloliquefaciens* strain that produces a fengycin or plipastatin-type compound, an iturin-type compound, and/or a surfactin-type compound. For background, see the following review article: Ongena, M., et al., "*Bacillus* Lipopeptides: Versatile Weapons for Plant Disease Biocontrol," Trends in Microbiology, Vol 16, No. 3, March 2008, pp. 115-125. *Bacillus* strains capable of producing lipopeptides include *Bacillus subtilis* QST713 (available as SERENADE OPTI or SERENADE ASO from Bayer CropScience LP, US, having NRRL Accession No. B21661 and described in U.S. Pat. No. 6,060,051), *Bacillus amyloliquefaciens* strain D747 (available as Double Nickel™ from Certis, US, having accession number FERM BP-8234 and disclosed in U.S. Pat. No. 7,094,592); *Bacillus subtilis* MBI600 (available as SUBTILEX® from Becker Underwood, US EPA Reg. No. 71840-8); *Bacillus subtilis* Y1336 (available as BIOBAC® WP from Bion-Tech, Taiwan, registered as a biological fungicide in Taiwan under Registration Nos. 4764, 5454, 5096 and 5277); *Bacillus amyloliquefaciens*, in particular strain FZB42 (available as RFIIZOVITAL® from ABiTEP, DE); and *Bacillus subtilis* var. *amyloliquefaciens* FZB24 (available from Novozymes Biologicals Inc., Salem, Va. or Syngenta Crop Protection, LLC, Greensboro, N.C. as the fungicide TAEGRO® or TAEGRO® ECO (EPA Registration No. 70127-5); and
(B2) fungi, for example: (B2.1) *Coniothyrium minitans*, in particular strain CON/M/91-8 (Accession No. DSM-9660; e.g. Contans® from Bayer); (B2.2) *Metschnikowia fructicola*, in particular strain NRRL Y-30752 (e.g. Shemer®); (B2.3) *Microsphaeropsis ochracea* (e.g. Microx® from Prophyta); (B2.5) *Trichoderma* spp., including *Trichoderma atroviride*, strain SC1 described in International Application No. PCT/IT2008/000196); (B2.6) *Trichoderma harzianum* rifaistrain KRL-AG2 (also known as strain T-22, /ATCC 208479, e.g. PLANTSHIELD T-22G, Rootshield®, and TurfShield from BioWorks, US); (B2.14) *Gliocladium roseum*, strain 321U from W. F. Stoneman Company LLC; (B2.35) *Talaromyces flavus*, strain V117b; (B2.36) *Trichoderma asperellum*, strain ICC 012 from Isagro; (B2.37) *Trichoderma asperellum*, strain SKT-1 (e.g. ECO-HOPE® from Kumiai Chemical Industry); (B2.38) *Trichoderma atroviride*, strain CNCM 1-1237 (e.g. Esquive® WP from Agrauxine, FR); (B2.39) *Trichoderma atroviride*, strain no. V08/002387; (B2.40) *Trichoderma atroviride*, strain NMI no. V08/002388; (B2.41) *Trichoderma atroviride*, strain NMI no. V08/002389; (B2.42) *Trichoderma atroviride*, strain NMI no. V08/002390; (B2.43) *Trichoderma atroviride*, strain LC52 (e.g. Tenet by Agrimm Technologies Limited); (B2.44) *Trichoderma atroviride*, strain ATCC 20476 (IMI 206040); (B2.45) *Trichoderma atroviride*, strain T11 (IMI352941/CECT20498); (B2.46) *Trichoderma harmatum*, (B2.47) *Trichoderma harzianum*, (B2.48) *Trichoderma harzianum* rifai T39 (e.g. Trichodex® from Makhteshim, US); (B2.49) *Trichoderma harzianum*, in particular, strain KD (e.g. Trichoplus from Biological Control Products, SA (acquired by Becker Underwood)); (B2.50) *Trichoderma harzianum*, strain ITEM 908 (e.g. Trianum-P from Koppert); (B2.51) *Trichoderma harzianum*, strain TH35 (e.g. Root-Pro by Mycontrol); (B2.52) *Trichoderma virens* (also known as *Gliocladium virens*), in particular strain GL-21 (e.g. SoilGard 12G by Certis, US); (B2.53) *Trichoderma viride*, strain TV1 (e.g. Trianum-P by Koppert); (B2.54) *Ampelomyces quisqualis*, in particular strain AQ 10 (e.g. AQ 10® by IntrachemBio Italia); (B2.56) *Aureobasidium pullulans*, in particular blastospores of strain DSM14940; (B2.57) *Aureobasidium pullulans*, in particular blastospores of strain DSM 14941; (B2.58) *Aureobasidium pullulans*, in particular mixtures of blastospores of strains DSM14940 and DSM 14941 (e.g. Botector® by bio-ferm, CH); (B2.64) *Cladosporium cladosporioides*, strain H39 (by Stichting Dienst Landbouwkundig Onderzoek); (B2.69) *Gliocladium catenulatum* (Synonym: *Clonostachys rosea* f. *catenulate*) strain J1446 (e.g. Prestop® by AgBio Inc. and also e.g. Primastop® by Kemira Agro Oy); (B2.70) *Lecanicillium lecanii* (formerly known as *Verticillium lecanii*) conidia of strain KV01 (e.g. Vertalec® by Koppert/Arysta); (B2.71) *Penicillium vermiculatum*; (B2.72) *Pichia anomala*, strain WRL-076 (NRRL Y-30842); (B2.75) *Trichoderma atroviride*, strain SKT-1 (FERM P-16510); (B2.76) *Trichoderma atroviride*, strain SKT-2 (FERM P-16511); (B2.77) *Trichoderma atroviride*, strain SKT-3 (FERM P-17021); (B2.78) *Trichoderma gamsii* (formerly *T. viride*), strain ICC080 (IMI CC 392151 CABI, e.g. BioDerma by AGROBIOSOL DE MEXICO, S.A. DE C.V.); (B2.79) *Trichoderma harzianum*, strain DB 103 (e.g., T-Gro 7456 by Dagutat Biolab); (B2.80) *Trichoderma polysporum*, strain IMI 206039 (e.g. Binab TF WP by BINAB Bio-Innovation AB, Sweden); (B2.81) *Trichoderma stromaticum* (e.g. Tricovab by Ceplac, Brazil); (B2.83) *Ulocladium oudemansii*, in particular strain HRU3 (e.g. Botry-Zen® by Botry-Zen Ltd, NZ); (B2.84) *Verticillium albo-atrum* (formerly *V. dahliae*), strain WCS850 (CBS 276.92; e.g. Dutch Trig by Tree Care Innovations); (B2.86) *Verticillium chlamydosporium*, (B2.87) mixtures of *Trichoderma asperellum* strain ICC 012 and *Trichoderma gamsii* strain ICC 080 (product known as e.g. BIO-TAM™ from Bayer CropScience LP, US).

Further examples of biological control agents which may be combined with the compound(s) and the composition of the invention are:
bacteria selected from the group consisting of *Bacillus cereus*, in particular *B. cereus* strain CNCM I-1562 and *Bacillus firmus*, strain 1-1582 (Accession number CNCM 1-1582), *Bacillus subtilis* strain OST 30002 (Accession No. NRRL B-50421), *Bacillus thuringiensis*, in particular *B. thuringiensis* subspecies *israelensis* (serotype H-14), strain AM65-52 (Accession No. ATCC 1276), *B. thuringiensis* subsp. *aizawai*, in particular strain ABTS-1857 (SD-1372), *B. thuringiensis* subsp. *kurstaki* strain HD-1, *B. thuringiensis* subsp. *tenebrionis* strain NB 176 (SD-5428), *Pasteuria penetrans, Pasteuria* spp. (*Rotylenchulus reniformis* nematode)-PR3 (Accession Number ATCC SD-5834), *Streptomyces microflavus* strain AQ6121 (=QRD 31.013, NRRL B-50550), and *Streptomyces galbus* strain AQ 6047 (Accession Number NRRL 30232);

fungi and yeasts selected from the group consisting of *Beauveria bassiana*, in particular strain ATCC 74040, *Lecanicillium* spp., in particular strain HRO LEC 12, *Metarhizium anisopliae*, in particular strain F52 (DSM3884 or ATCC 90448), *Paecilomyces fumosoroseus* (now: *Isaria fumosorosea*), in particular strain IFPC 200613, or strain Apopka 97 (Accession No. ATCC 20874), and *Paecilomyces lilacinus*, in particular *P. lilacinus* strain 251 (AGAL 89/030550);

viruses selected from the group consisting of *Adoxophyes orana* (summer fruit *tortrix*) granulosis virus (GV), *Cydia pomonella* (codling moth) granulosis virus (GV), *Helicoverpa armigera* (cotton bollworm) nuclear polyhedrosis virus (NPV), *Spodoptera exigua* (beet armyworm) mNPV, *Spodoptera frugiperda* (fall armyworm) mNPV, and *Spodoptera littoralis* (African cotton leafworm) NPV.

bacteria and fungi which can be added as 'inoculant' to plants or plant parts or plant organs and which, by virtue of their particular properties, promote plant growth and plant health. Examples are: *Agrobacterium* spp., *Azorhizobium caulinodans. Azospirillum* spp., *Azotobacter* spp., *Bradyrhizobium* spp., *Burkholderia* spp., in particular *Burkholderia cepacia* (formerly known as *Pseudomonas cepacia*), *Gigaspora* spp., or *Gigaspora monosporum. Glomus* spp., *Laccaria* spp., *Lactobacillus buchneri, Paraglomus* spp., *Pisolithus tinctorus, Pseudomonas* spp., *Rhizobium* spp., in particular *Rhizobium trifolii, Rhizopogon* spp., *Scleroderma* spp., *Suillus* spp., and *Streptomyces* spp.

plant extracts and products formed by microorganisms including proteins and secondary metabolites which can be used as biological control agents, such as *Allium sativum, Artemisia absinthium,* azadirachtin, Biokeeper WP, *Cassia nigricans, Celastrus angulatus, Chenopodium anthelminticum,* chitin, Armour-Zen, Dryopteris filix-mas, *Equisetum arvense*, Fortune Aza, Fungastop, Pleads Up (*Chenopodium quinoa* saponin extract), *Pyrethrum/Pyrethrins, Quassia amara, Quercus, Quillaja*, Regalia, "Requiem™ Insecticide", rotenone, *ryania*/ryanoide, *Symphytum officinale, Tanacetum vulgare*, thymol, Triad 70, TriCon, *Tropaeulum majus, Urtica dioica*, Veratrin, *Viscum album, Brassicaceae* extract, in particular oilseed rape powder or mustard powder.

Examples of insecticides, acaricides and nematicides, respectively, which could be mixed with the compound(s) and the composition of the invention are:

(1) Acetylcholinesterase (AChE) inhibitors, such as, for example, carbamates, for example alanycarb, aldicarb, bendiocarb, benfuracarb, butocarboxim, butoxycarboxim, carbaryl, carbofuran, carbosulfan, ethiofencarb, fenobucarb, formetanate, furathiocarb, isoprocarb, methiocarb, methomyl, metolcarb, oxamyl, pirimicarb, propoxur, thiodicarb, thiofanox, triazamate, trimethacarb, XMC and xylylcarb; or organophosphates, for example acephate, azamethiphos, azinphos-ethyl, azinphos-methyl, cadusafos, chlorethoxyfos, chlorfenvinphos, chlormephos, chlorpyrifos-methyl, coumaphos, cyanophos, demeton-S-methyl, diazinon, dichlorvos/DDVP, dicrotophos, dimethoate, dimethylvinphos, disulfoton, EPN, ethion, ethoprophos, famphur, fenamiphos, fenitrothion, fenthion, fosthiazate, heptenophos, imicyafos, isofenphos, isopropyl O-(methoxyaminothiophosphoryl) salicylate, isoxathion, malathion, mecarbam, methamidophos, methidathion, mevinphos, monocrotophos, naled, omethoate, oxydemeton-methyl, parathion-methyl, phenthoate, phorate, phosalone, phosmet, phosphamidon, phoxim, pirimiphos-methyl, profenofos, propetamphos, prothiofos, pyraclofos, pyridaphenthion, quinalphos, sulfotep, tebupirimfos, temephos, terbufos, tetrachlorvinphos, thiometon, triazophos, triclorfon and vamidothion.

(2) GABA-gated chloride channel blockers, such as, for example, cyclodiene-organochlorines, for example chlordane and endosulfan or phenylpyrazoles (fiproles), for example ethiprole and fipronil.

(3) Sodium channel modulators, such as, for example, pyrethroids, e.g. acrinathrin, allethrin, d-cis-trans allethrin, d-trans allethrin, bifenthrin, bioresmethrin, bioallethrin, bioallethrin s-cyclopentenyl isomer, bioresmethrin, cycloprothrin, cyfluthrin, beta-cyfluthrin, cyhalothrin, lambda-cyhalothrin, gamma-cyhalothrin, cypermethrin, alpha-cypermethrin, beta-cypermethrin, theta-cypermethrin, zeta-cypermethrin, cyphenothrin [(1R)-trans-isomer], deltamethrin, empenthrin [(EZ)-(1R)-isomer], esfenvalerate, etofenprox, fenpropathrin, fenvalerate, flucythrinate, flumethrin, tau-fluvalinate, halfenprox, imiprothrin, kadethrin, momfluorothrin, permethrin, phenothrin [(1R)-trans-isomer], prallethrin, pyrethrins (pyrethrum), resmethrin, silafluofen, tefluthrin, tetramethrin, tetramethrin [(1R)-isomer)], tralomethrin and transfluthrin or DDT or methoxychlor.

(4) Nicotinic acetylcholine receptor (nAChR) competitive modulators, such as, for example, neonicotinoids, e.g. acetamiprid, clothianidin, dinotefuran, imidacloprid, nitenpyram, thiacloprid and thiamethoxam or nicotine or sulfoxaflor or flupyradifurone.

(5) Nicotinic acetylcholine receptor (nAChR) allosteric modulators, such as, for example, spinosyns, e.g. spinetoram and spinosad.

(6) Glutamate-gated chloride channel (GluCl) allosteric modulators, such as, for example, avermectins/milbemycins, for example abamectin, emamectin benzoate, lepimectin and milbemectin.

(7) Juvenile hormone mimics, such as, for example, juvenile hormone analogues, e.g. hydroprene, kinoprene and methoprene or fenoxycarb or pyriproxyfen.

(8) Miscellaneous non-specific (multi-site) inhibitors, such as, for example, alkyl halides, e.g. methyl bromide and other alkyl halides; or chloropicrine or sulphuryl fluoride or borax or tartar emetic or methyl isocyanate generators, e.g. diazomet and metam.

(9) Modulators of Chordotonal Organs, such as, for example pymetrozine or flonicamid.

(10) Mite growth inhibitors, such as, for example clofentezine, hexythiazox and diflovidazin or etoxazole.

(11) Microbial disruptors of the insect gut membrane, such as, for example *Bacillus thuringiensis* subspecies *israelensis, Bacillus sphaericus, Bacillus thuringiensis* subspecies *aizawai, Bacillus thuringiensis* subspecies *kurstaki, Bacillus thuringiensis* subspecies *tenebrionis*, and B.t. plant proteins: Cry1Ab, Cry1Ac, Cry1 Fa, Cry1A.105, Cry2Ab, Vip3A, mCry3A, Cry3Ab, Cry3Bb, Cry34Ab1/35Ab1.

(12) Inhibitors of mitochondrial ATP synthase, such as, ATP disruptors such as, for example, diafenthiuron or organotin compounds, for example azocyclotin, cyhexatin and fenbutatin oxide or propargite or tetradifon.

(13) Uncouplers of oxidative phosphorylation via disruption of the proton gradient, such as, for example, chlorfenapyr, DNOC and sulfluramid.

(14) Nicotinic acetylcholine receptor channel blockers, such as, for example, bensultap, cartap hydrochloride, thiocylam, and thiosultap-sodium.

(15) Inhibitors of chitin biosynthesis, type 0, such as, for example, bistrifluron, chlorfluazuron, diflubenzuron, flucycloxuron, flufenoxuron, hexaflumuron, lufenuron, novaluron, noviflumuron, teflubenzuron and triflumuron.

(16) Inhibitors of chitin biosynthesis, type 1, for example buprofezin.

(17) Moulting disruptor (in particular for Diptera, i.e. dipterans), such as, for example, cyromazine.

(18) Ecdysone receptor agonists, such as, for example, chromafenozide, halofenozide, methoxyfenozide and tebufenozide.

(19) Octopamine receptor agonists, such as, for example, amitraz.

(20) Mitochondrial complex III electron transport inhibitors, such as, for example, hydramethylnone or acequinocyl or fluacrypyrim.

(21) Mitochondrial complex I electron transport inhibitors, such as, for example from the group of the METI acaricides, e.g. fenazaquin, fenpyroximate, pyrimidifen, pyridaben, tebufenpyrad and tolfenpyrad or rotenone (Derris).

(22) Voltage-dependent sodium channel blockers, such as, for example indoxacarb or metaflumizone.

(23) Inhibitors of acetyl CoA carboxylase, such as, for example, tetronic and tetramic acid derivatives, e.g. spirodiclofen, spiromesifen and spirotetramat.

(24) Mitochondrial complex IV electron transport inhibitors, such as, for example, phosphines, e.g. aluminium phosphide, calcium phosphide, phosphine and zinc phosphide or cyanides, e.g. calcium cyanide, potassium cyanide and sodium cyanide.

(25) Mitochondrial complex II electron transport inhibitors, such as, for example, befa-ketonitrile derivatives, e.g. cyenopyrafen and cyflumetofen and carboxanilides, such as, for example, pyflubumide.

(28) Ryanodine receptor modulators, such as, for example, diamides, e.g. chlorantraniliprole, cyantraniliprole and flubendiamide, further active compounds such as, for example, Afidopyropen, Afoxolaner, Azadirachtin, Benclothiaz, Benzoximate, Bifenazate, Broflanilide, Bromopropylate, Chinomethionat, Chloroprallethrin, Cryolite, Cyclaniliprole, Cycloxaprid, Cyhalodiamide, Dicloromezotiaz, Dicofol, epsilon-Metofluthrin, epsilon-Momfluthrin, Flometoquin, Fluazaindolizine, Fluensulfone, Flufenerim, Flufenoxystrobin, Flufiprole, Fluhexafon, Fluopyram, Fluralaner, Fluxametamide, Fufenozide, Guadipyr, Heptafluthrin, Imidaclothiz, Iprodione, kappa-Bifenthrin, kappa-Tefluthrin, Lotilaner, Meperfluthrin, Paichongding, Pyridalyl, Pyrifluquinazon, Pyriminostrobin, Spirobudiclofen, Tetramethylfluthrin, Tetraniliprole, Tetrachlorantraniliprole, Tigolaner, Tioxazafen, Thiofluoximate, Triflumezopyrim and iodomethane; furthermore preparations based on *Bacillus firmus* (1-1582, BioNeem, Votivo), and also the following compounds: 1-{2-fluoro-4-methyl-5-[(2,2,2-trifluoroethyl)sulphinyl]phenyl}-3-(trifluoromethyl)-1H-1,2,4-triazole-5-amine (known from WO2006/043635) (CAS 885026-50-6), {1'-[(2E)-3-(4-chlorophenyl)prop-2-en-1-yl]-5-fluorospiro[indol-3,4'-piperidin]-1 (2H)-yl}(2-chloropyridin-4-yl)methanone (known from WO2003/106457) (CAS 637360-23-7), 2-chloro-N-[2-{1-[(2E)-3-(4-chlorophenyl)prop-2-en-1-yl]piperidin-4-yl}-4-(trifluoromethyl)phenyl]isonicotinamide (known from WO2006/003494) (CAS 872999-66-1), 3-(4-chloro-2,6-dimethylphenyl)-4-hydroxy-8-methoxy-1,8-diazaspiro[4.5]dec-3-en-2-one (known from WO 2010052161) (CAS 1225292-17-0), 3-(4-chloro-2,6-dimethylphenyl)-8-methoxy-2-oxo-1,8-diazaspiro[4.5]dec-3-en-4-yl ethyl carbonate (known from EP2647626) (CAS 1440516-42-6), 4-(but-2-yn-1-yloxy)-6-(3,5-dimethylpiperidin-1-yl)-5-fluoropyrimidine (known from WO2004/099160) (CAS 792914-58-0), PF1364 (known from JP2010/018586) (CAS 1204776-60-2), N-[(2E)-1-[(6-chloropyridin-3-yl)methyl]pyridin-2(1H)-ylidene]-2,2,2-trifluoroacetamide (known from WO2012/029672) (CAS 1363400-41-2), (3E)-3-[1-[(6-chloro-3-pyridyl)methyl]-2-pyridylidene]-1,1,1-trifluoro-propan-2-one (known from WO2013/144213) (CAS 1461743-15-6), N-[3-(benzylcarbamoyl)-4-chlorophenyl]-1-methyl-3-(pentafluoroethyl)-4-(trifluoromethyl)-1H-pyrazole-5-carboxamide (known from WO2010/051926) (CAS 1226889-14-0), 5-bromo-4-chloro-N-[4-chloro-2-methyl-6-(methylcarbamoyl)phenyl]-2-(3-chloro-2-pyridyl)pyrazole-3-carboxamide (known from CN103232431) (CAS 1449220-44-3), 4-[5-(3,5-dichlorophenyl)-4,5-dihydro-5-(trifluoromethyl)-3-isoxazolyl]-2-methyl-N-(cis-1-oxido-3-thietanyl)-benzamide, 4-[5-(3,5-dichlorophenyl)-4,5-dihydro-5-(trifluoromethyl)-3-isoxazolyl]-2-methyl-N-(trans-1-oxido-3-thietanyl)-benzamide and 4-[(5S)-5-(3,5-dichlorophenyl)-4,5-dihydro-5-(trifluoromethyl)-3-isoxazolyl]-2-methyl-N-(cis-1-oxido-3-thietanyl)benzamide (known from WO 2013/050317 A1) (CAS 1332628-83-7), N-[3-chloro-1-(3-pyridinyl)-1H-pyrazol-4-yl]-N-ethyl-3-[(3, 3,3-trifluoropropyl)sulfinyl]-propanamide, (+)-N-[3-chloro-1-(3-pyridinyl)-1H-pyrazol-4-yl]-N-ethyl-3-[(3, 3,3-trifluoropropyl)sulfinyl]-propanamide and (−)-N-[3-chloro-1-(3-pyridinyl)-1H-pyrazol-4-yl]-N-ethyl-3-[(3,3,3-trifluoropropyl)sulfinyl]-propanamide (known from WO 2013/162715 A2, WO 2013/162716 A2, US 2014/0213448 A1) (CAS 1477923-37-7), 5-[[(2E)-3-chloro-2-propen-1-yl]amino]-1-[2,6-dichloro-4-(trifluoromethyl)phenyl]-4-[(trifluoromethyl)sulfinyl]-1H-pyrazole-3-carbonitrile (known from CN 101337937 A) (CAS 1105672-77-2), 3-bromo-N-[4-chloro-2-methyl-6-[(methylamino)thioxomethyl]phenyl]-1-(3-chloro-2-pyridinyl)-1H-pyrazole-5-carboxamide, (Liudaibenjiaxuanan, known from CN 103109816 A) (CAS 1232543-85-9); N-[4-chloro-2-[[(1,1-dimethylethyl)amino]carbonyl]-6-methylphenyl]-1-(3-chloro-2-pyridinyl)-3-(fluoromethoxy)-1H-Pyrazole-5-carboxamide (known from WO 2012/034403 A1) (CAS 1268277-22-0), N-[2-(5-amino-1,3,4-thiadiazol-2-yl)-4-chloro-6-methylphenyl]-3-bromo-1-(3-chloro-2-pyridinyl)-1H-pyrazole-5-carboxamide (known from WO 2011/085575 A1) (CAS 1233882-22-8), 4-[3-[2,6-dichloro-4-[(3,3-dichloro-2-propen-1-yl)oxy]phenoxy]propoxy]-2-methoxy-6-(trifluoromethyl)-pyrimidine (known from CN 101337940 A) (CAS 1108184-52-6); (2E)- and 2(Z)-2-[2-(4-cyanophenyl)-1-[3-(trifluoromethyl)phenyl]ethylidene]-N-[4-(difluoromethoxy)phenyl]-hydrazinecarboxamide (known from CN 101715774 A) (CAS 1232543-85-9); 3-(2,2-dichloroethenyl)-2,2-dimethyl-4-(1H-benzimidazol-2-yl)phenyl-cyclopropanecarboxylic acid ester (known from CN 103524422 A) (CAS 1542271-46-4); (4aS)-7-chloro-2,5-dihydro-2-[[(methoxycarbonyl)[4-[(trifluoromethyl)thio]phenyl]amino]carbonyl]-indeno[1,2-e][1,3,4]oxadiazine-4a (3AV)-carboxylic acid methyl ester (known from CN 102391261 A) (CAS 1370358-69-2); 6-deoxy-3-O-ethyl-2, 4-di-O-methyl-, 1-[N-[4-[1-[4-(1,1,2,2,2-pentafluoroethoxy)phenyl]-1H-1,2,4-triazol-3-yl]phenyl]carbamate]-α-L-mannopyranose (known from US 2014/0275503 A1) (CAS 1181213-14-8); 8-(2-cyclopropylmethoxy-4-trifluoromethyl-phenoxy)-3-(6-trifluoromethyl-pyridazin-3-yl)-3-azabicyclo[3.2.1]octane (CAS 1253850-56-4), (8-anti)-8-(2-cyclopropylmethoxy-4-trifluoromethyl-phenoxy)-3-(6-trifluoromethyl-pyridazin-3-yl)-3-aza-bicyclo[3.2.1]octane (CAS 933798-27-7), (8-syn)-8-(2-cyclopropylmethoxy-4-trifluoromethyl-phenoxy)-3-(6-trifluoromethyl-pyridazin-3-yl)-3-aza-bicyclo[3.2.1]octane (known from WO 2007040280 A1, WO 2007040282 A1) (CAS 934001-66-8), N-[3-chloro-1-(3-pyridinyl)-1H-pyrazol-4-yl]-N-ethyl-3-[(3,3,3-trifluoropropyl)thio]-propanamide (known from WO 2015/058021 A1, WO 2015/058028 A1) (CAS 1477919-27-9) and N-[4-(aminothioxomethyl)-2-methyl-6-[(methylamino)carbonyl]phenyl]-3-bromo-1-(3-chloro-2-pyridinyl)-1H-pyrazole-5-carboxamide (known from CN 103265527 A) (CAS 1452877-50-7), 5-(1,3-dioxan-2-yl)-4-[[4-(trifluoromethyl)phenyl]methoxy]-pyrimidine (known from WO 2013/115391 A1) (CAS 1449021-97-9), 3-(4-chloro-2,6-dimethylphenyl)-4-hydroxy-8-methoxy-1-methyl-1,8-diazaspiro[4.5]dec-3-en-2-one (known from WO 2010/066780 A1, WO 2011/151146 A1) (CAS 1229023-34-0), 3-(4-chloro-2,6-dimethylphenyl)-8-methoxy-1-methyl-1,8-diazaspiro[4.5]decane-2,4-dione (known from WO 2014/187846 A1) (CAS 1638765-58-8), 3-(4-chloro-2,6-dimethylphenyl)-8-methoxy-1-methyl-2-oxo-1, 8-diazaspiro[4.5]dec-3-en-4-yl-carbonic acid ethyl ester (known from WO 2010/066780 A1, WO 2011151146 A1) (CAS 1229023-00-0), N-[1-[(6-chloro-3-pyridinyl)methyl]-2(1H)-pyridinylidene]-2,2,2-trifluoro-acetamide (known from DE 3639877 A1, WO 2012029672 A1) (CAS 1363400-41-2), [N(E)]-N-[1-[(6-chloro-3-pyridinyl)methyl]-2(1H)-pyridinylidene]-2,2,2-trifluoro-acetamide, (known from WO 2016005276 A1) (CAS 1689566-03-7), [N(Z)]—N-[1-[(6-chloro-3-pyridinyl)methyl]-2(1H)-pyridinylidene]-2,2,2-trifluoro-acetamide, (CAS 1702305-40-5), 3-endo-3-[2-propoxy-4-(trifluoromethyl)phenoxy]-9-[[5-(trifluoromethyl)-2-pyridinyl]oxy]-9-azabicyclo[3.3.1]nonane (known from WO 2011/105506 A1, WO 2016/133011 A1) (CAS 1332838-17-1).

Examples of safeners which could be mixed with the compound(s) and the composition of the invention are, for example, benoxacor, cloquintocet (-mexyl), cyometrinil, cyprosulfamide, dichlormid, fenchlorazole (-ethyl), fenclorim, flurazole, fluxofenim, furilazole, isoxadifen (-ethyl), mefenpyr (-diethyl), naphthalic anhydride, oxabetrinil, 2-methoxy-N-({4-[(methylcarbamoyl)amino]phenyl}-sulphonyl)benzamide (CAS 129531-12-0), 4-(dichloroacetyl)-1-oxa-4-azaspiro[4.5]decane (CAS 71526-07-3), 2,2,5-trimethyl-3-(dichloroacetyl)-1,3-oxazolidine (CAS 52836-31-4).

Examples of herbicides which could be mixed with the compound(s) and the composition of the invention are:
Acetochlor, acifluorfen, acifluorfen-sodium, aclonifen, alachlor, allidochlor, alloxydim, alloxydim-sodium, ametryn, amicarbazone, amidochlor, amidosulfuron, 4-amino-3-chloro-6-(4-chloro-2-fluoro-3-methylphenyl)-5-fluoropyridine-2-carboxylic acid, aminocyclopyrachlor, aminocyclopyrachlor-potassium, aminocyclopyrachlor-methyl, aminopyralid, amitrole, ammoniumsulfamate, anilofos, asulam, atrazine, azafenidin, azimsulfuron, beflubutamid, benazolin, benazolin-ethyl, benfluralin, benfuresate, bensulfuron, bensulfuron-methyl, bensulide, bentazone, benzobicyclon, benzofenap, bicyclopyron, bifenox, bilanafos, bilanafos-sodium, bispyribac, bispyribac-sodium, bromacil, bromobutide, bromofenoxim, bromoxynil, bromoxynil-butyrate, -potassium, -heptanoate, and -octanoate, busoxinone, butachlor, butafenacil, butamifos, butenachlor, butralin, butroxydim, butylate, cafenstrole, carbetamide, carfentrazone, carfentrazone-ethyl, chloramben, chlorbromuron, chlorfenac, chlorfenac-sodium, chlorfenprop, chlorflurenol, chlorflurenol-methyl, chloridazon, chlorimuron, chlorimuron-ethyl, chlorophthalim, chlorotoluron, chlorthal-dimethyl, chlorsulfuron, cinidon, cinidon-ethyl, cinmethylin, cinosulfuron, clacyfos, clethodim, clodinafop, clodinafop-propargyl, clomazone, clomeprop, clopyralid, cloransulam, cloransulam-methyl, cumyluron, cyanamide, cyanazine, cycloate, cyclopyrimorate, cyclosulfamuron, cycloxydim, cyhalofop, cyhalofop-butyl, cyprazine, 2,4-D, 2,4-D-butotyl, -butyl, -dimethylammonium, -diolamin, -ethyl, -2-ethylhexyl, -isobutyl, -isooctyl, -isopropyl-ammonium, -potassium, -triisopropanolammonium, and -trolamine, 2,4-DB, 2,4-DB-butyl, -dimethyl-ammonium, -isooctyl, -potassium, and -sodium, daimuron (dymron), dalapon, dazomet, n-decanol, desmedipham, detosyl-pyrazolate (DTP), dicamba, dichlobenil, 2-(2,4-dichlorobenzyl)-4,4-dimethyl-1,2-oxazolidin-3-one, 2-(2,5-dichlorobenzyl)-4,4-dimethyl-1,2-oxazolidin-3-one, dichlorprop, dichlorprop-P, diclofop, diclofop-methyl, diclofop-P-methyl, diclosulam, difenzoquat, diflufenican, diflufenzopyr, diflufenzopyr-sodium, dimefuron, dimepiperate, dimethachlor, dimethametryn, dimethenamid, dimethenamid-P, dimetrasulfuron, dinitramine, dinoterb, diphenamid, diquat, diquat-dibromid, dithiopyr, diuron, DNOC, endothal, EPTC, esprocarb, ethalfluralin, ethametsulfuron, etha-metsulfuron-methyl, ethiozin, ethofumesate, ethoxyfen, ethoxyfen-ethyl, ethoxysulfuron, etobenzanid, F-9600, F-5231, i.e. N-{2-chloro-4-fluoro-5-[4-(3-fluoropropyl)-5-oxo-4,5-dihydro-1H-tetrazol-1-yl]phenyl}ethanesulfonamide, F-7967, i. e. 3-[7-chloro-5-fluoro-2-(trifluoromethyl)-1H-benzimidazol-4-yl]-1-methyl-6-(trifluoromethyl)pyrimidine-2,4(1H,3H)-dione, fenoxaprop, fenoxaprop-P, fenoxaprop-ethyl, fenoxaprop-P-ethyl, fenoxasulfone, fenquinotrione, fentrazamide, flamprop, flamprop-M-isopropyl, flamprop-M-methyl, flazasulfuron, florasulam, fluazifop, fluazifop-P, fluazifop-butyl, fluazifop-P-butyl, flucarbazone, flucarbazone-sodium, flucetosulfuron, fluchloralin, flufenacet, flufenpyr, flufenpyr-ethyl, flumetsulam, flumiclorac, flumiclorac-pentyl, flumioxazin, fluometuron, flurenol, flurenol-butyl, -dimethylammonium and -methyl, fluoroglycofen, fluoroglycofen-ethyl, flupropanate, flupyr-sulfuron, flupyrsulfuron-methyl-sodium, fluridone, flurochloridone, fluroxypyr, fluroxypyr-meptyl, flurtamone, fluthiacet, fluthiacet-methyl, fomesafen, fomesafen-sodium, foramsulfuron, fosamine, glufosinate, glufosinate-ammonium, glufosinate-P-sodium, glufosinate-P-ammonium, glufosinate-P-sodium, glyphosate, glyphosate-ammonium, -isopropylammonium, -diammonium, -dimethylammonium, -potassium, -sodium, and -trimesium, H-9201, i.e. O-(2,4-dimethyl-6-nitrophenyl) O-ethyl isopropylphosphoramidothioate, halauxifen, halauxifen-methyl, halosafen, halosulfuron, halosulfuron-methyl, haloxyfop, haloxyfop-P, haloxyfop-ethoxyethyl, haloxyfop-P-ethoxyethyl, haloxyfop-methyl, haloxyfop-P-methyl, hexazinone, HW-02, i.e. 1-(dimethoxyphosphoryl)ethyl-(2,4-dichlorophenoxy)acetate, imazamethabenz, imazamethabenz-methyl, imazamox, imazamox-ammonium, imazapic, imazapic-ammonium, imazapyr, imazapyr-isopropylammonium, imazaquin, imazaquin-ammonium, imazethapyr, imazethapyr-immonium, imazosulfuron, indanofan, indaziflam, iodosulfuron, iodosulfuron-methyl-sodium, ioxynil, ioxynil-octanoate, -potassium and -sodium, ipfencarbazone, isoproturon, isouron, isoxaben, isoxaflutole, karbutilate, KUH-043, i.e. 3-({[5-(difluoromethyl)-1-methyl-3-(trifluoromethyl)-1H-pyrazol-4-yl]methyl}sulfonyl)-5,5-dimethyl-4,5-dihydro-1,2-oxazole, ketospiradox, lactofen, lenacil, linuron, MCPA, MCPA-butotyl, -dimethylammonium, -2-ethylhexyl, -isopropylammonium, -potassium, and -sodium, MCPB, MCPB-methyl, -ethyl, and -sodium, mecoprop, mecoprop-sodium, and -butotyl, mecoprop-P, mecoprop-P-butotyl, -dimethylammonium, -2-ethylhexyl, and -potassium, mefenacet, mefluidide, mesosulfuron, mesosulfuron-methyl, mesotrione, methabenzthiazuron, metam, metamifop, metamitron, metazachlor, metazosulfuron, methabenz-thiazuron, methiopyrsulfuron, methiozolin, methyl isothiocyanate, metobromuron, metolachlor, S-metolachlor, metosulam, metoxuron, metribuzin, metsulfuron, metsulfuron-methyl, molinat, monolinuron, monosulfuron, monosulfuron-ester, MT-5950, i.e. N-(3-chloro-4-isopropylphenyl)-2-methylpentan amide, NGGC-011, napropamide, NC-310, i.e. [5-(benzyloxy)-1-methyl-1H-pyrazol-4-yl](2,4-dichlorophenyl)methanone, neburon, nicosulfuron, nonanoic acid (pelargonic acid), norflurazon, oleic acid (fatty acids), orbencarb, orthosulfamuron, oryzalin, oxadiargyl, oxadiazon, oxasulfuron, oxaziclomefon, oxyfluorfen, paraquat, paraquat dichloride, pebulate, pendimethalin, penoxsulam, pentachlorophenol, pentoxazone, pethoxamid, petroleum oils, phenmedipham, picloram, picolinafen, pinoxaden, piperophos, pretilachlor, primisulfuron, primisulfuron-methyl, prodiamine, profoxydim, prometon, prometryn, propachlor, propanil, propaquizafop, propazine, propham, propisochlor, propoxycarbazone, propoxycarbazone-sodium, propyrisulfuron, propyzamide, prosulfocarb, pro-sulfuron, pyraclonil, pyraflufen, pyraflufen-ethyl, pyrasulfotole, pyrazolynate (pyrazolate), pyrazo-sulfuron, pyrazosulfuron-ethyl, pyrazoxyfen, pyribambenz, pyribambenz-isopropyl, pyribambenz-propyl, pyribenzoxim, pyributicarb, pyridafol, pyridate, pyriftalid, pyriminobac, pyriminobac-methyl, pyrimisulfan, pyrithiobac, pyrithiobac-sodium, pyroxasulfone, pyroxsulam, quinclorac, quinmerac, quinoclamine, quizalofop, quizalofop-ethyl, quizalofop-P, quizalofop-P-ethyl, quizalofop-P-tefuryl, rimsulfuron, saflufenacil, sethoxydim, siduron, simazine, simetryn, SL-261, sulcotrion, sulfentrazone, sulfometuron, sulfometuron-methyl, sulfosulfuron, SYN-523, SYP-249, i.e. 1-ethoxy-3-methyl-1-oxobut-3-en-2-yl 5-[2-chloro-4-(trifluoromethyl)phenoxy]-2-nitrobenzoate, SYP-300, i.e. 1-[7-fluoro-3-oxo-4-(prop-2-yn-1-yl)-3,4-dihydro-2H-1,4-benzoxazin-6-yl]-3-propyl-2-thioxoimidazolidine-4,5-dione, 2,3,6-TBA, TCA (trichloroacetic acid), TCA-sodium, tebuthiuron, tefuryltrione, tembotrione, tepraloxydim, terbacil, terbucarb, terbumeton, terbuthylazin, terbutryn, thenylchlor, thiazopyr, thien-carbazone, thiencarbazone-methyl, thifensulfuron, thifensulfuron-methyl, thiobencarb, tiafenacil, tolpyralate, topramezone, tralkoxydim, triafamone, tri-allate, triasulfuron, triaziflam, tribenuron, tribenuron-methyl, triclopyr, trietazine, trifloxysulfuron, trifloxysulfuron-sodium, trifludimoxazin, trifluralin, triflusulfuron, triflusulfuron-methyl, tritosulfuron, urea sulfate, vernolate, XDE-848, ZJ-0862, i.e. 3,4-dichloro-N-{2-[(4,6-dimethoxypyrimidin-2-yl)oxy]benzyl}aniline, and the following compounds:

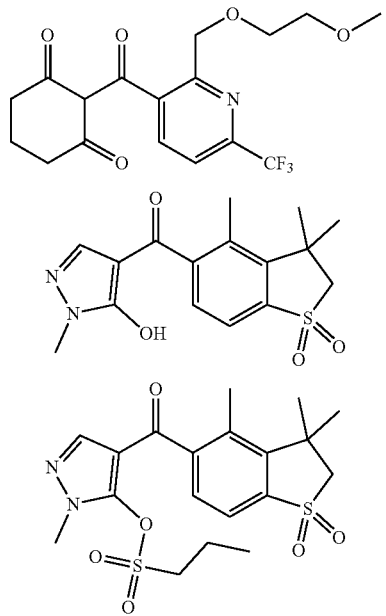

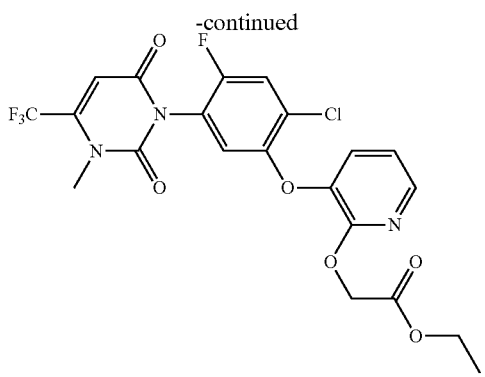

Examples for plant growth regulators are:
Acibenzolar, acibenzolar-S-methyl, 5-aminolevulinic acid, ancymidol, 6-benzylaminopurine, Brassinolid, catechine, chlormequat chloride, cloprop, cyclanilide, 3-(cycloprop-1-enyl) propionic acid, daminozide, dazomet, n-decanol, dikegulac, dikegulac-sodium, endothal, endothal-dipotassium, -disodium, and -mono(N,N-dimethylalkylammonium), ethephon, flumetralin, flurenol, flurenol-butyl, flurprimidol, forchlorfenuron, gibberellic acid, inabenfide, indol-3-acetic acid (IAA), 4-indol-3-ylbutyric acid, isoprothiolane, probenazole, jasmonic acid, maleic hydrazide, mepiquat chloride, 1-methyl-cyclopropene, methyl jasmonate, 2-(1-naphthyl)acetamide, 1-naphthylacetic acid, 2-naphthyloxyacetic acid, nitrophenolate-mixture, paclobutrazol, N-(2-phenylethyl)-beta-alanine, N-phenylphthalamic acid, prohexadione, prohexadione-calcium, prohydrojasmone, salicylic acid, strigolactone, tecnazene, thidiazuron, triacontanol, trinexapac, trinexapac-ethyl, tsitodef, uniconazole, uniconazole-P.

Methods and Uses

The compound(s) and the composition of the invention have potent plant defense modulating potential. They can be used for controlling unwanted bacteria, in particular bacteria of the genus *Xanthomonas*. The compound(s) and the composition of the invention can be used to protect seeds, germinating seeds, emerged seedlings, plants, plant parts, fruits, harvest goods and/or the soil in which the plants grow.

Control or controlling as used herein encompasses preventive, protective, curative and eradicative treatment of unwanted microorganisms.

Thus, the present invention relates to a method for controlling bacterial diseases caused by bacteria of the genus *Xanthomonas* comprising the step of applying at least one compound of the invention or at least one composition of the invention to the plants, plant parts, seeds, fruits or to the soil in which the plants grow.

Typically, when the compound(s) and the composition of the invention are used in curative or protective methods for controlling bacterial diseases, an effective and plant-compatible amount thereof is applied to the plants, plant parts, fruits, seeds or to the soil or substrates in which the plants grow. Suitable substrates that may be used for cultivating plants include inorganic based substrates, such as mineral wool, in particular stone wool, perlite, sand or gravel; organic substrates, such as peat, pine bark or sawdust; and petroleum based substrates such as polymeric foams or plastic beads. Effective and plant-compatible amount means an amount that is sufficient to control the bacteria present or liable to appear on the cropland and that does not entail any appreciable symptom of phytotoxicity for said crops. Such an amount can vary within a wide range depending on the pathogens to be controlled, the type of crop, the crop growth stage, the climatic conditions and the respective compound(s) or composition of the invention used. This amount can be determined by systematic field trials that are within the capabilities of a person skilled in the art. Diseases caused by bacterial pathogens, for example *Xanthomonas* species (e.g. *Xanthomonas campestris* pv. *Oryzae*), *Pseudomonas* species (e.g. *Pseudomonas syringae* pv. *Lachrymans*), *Erwinia* species (e.g. *Erwinia amylovora*) may be controlled by the compounds of the present invention. The compounds of formula (I) may also be efficient for controlling phytopathogenic fungi on plants.

Plants and Plant Parts

The compound(s) and the composition of the invention may be applied to any plants or plant parts.

Plants mean all plants and plant populations, such as desired and undesired wild plants or crop plants (including naturally occurring crop plants). Crop plants may be plants which can be obtained by conventional breeding and optimization methods or by biotechnological and genetic engineering methods or combinations of these methods, including the genetically modified plants (GMO or transgenic plants) and the plant cultivars which are protectable and non-protectable by plant breeders' rights.

Genetically Modified Plants (GMO)

Genetically modified plants (GMO or transgenic plants) are plants in which a heterologous gene has been stably integrated into the genome. The expression "heterologous gene" essentially means a gene which is provided or assembled outside the plant and when introduced in the nuclear, chloroplastic or mitochondrial genome. This gene gives the transformed plant new or improved agronomic or other properties by expressing a protein or polypeptide of interest or by downregulating or silencing other gene(s) which are present in the plant (using for example, antisense technology, cosuppression technology, RNA interference—RNAi—technology or microRNA—miRNA—technology). A heterologous gene that is located in the genome is also called a transgene. A transgene that is defined by its particular location in the plant genome is called a transformation or transgenic event.

Plant cultivars are understood to mean plants which have new properties ("traits") and have been obtained by conventional breeding, by mutagenesis or by recombinant DNA techniques. They can be cultivars, varieties, bio- or genotypes.

Plant parts are understood to mean all parts and organs of plants above and below the ground, such as shoots, leaves, needles, stalks, stems, flowers, fruit bodies, fruits, seeds, roots, tubers and rhizomes. The plant parts also include harvested material and vegetative and generative propagation material, for example cuttings, tubers, rhizomes, slips and seeds.

Plants which may be treated in accordance with the methods of the invention include the following: cotton, flax, grapevine, fruit, vegetables, such as *Rosaceae* sp. (for example pome fruits such as apples and pears, but also stone fruits such as apricots, cherries, almonds and peaches, and soft fruits such as strawberries), *Ribesioidae* sp., *Juglandaceae* sp., *Betulaceae* sp., *Anacardiaceae* sp., *Fagaceae* sp., *Moraceae* sp., *Oleaceae* sp., *Actinidaceae* sp., *Lauraceae* sp., *Musaceae* sp. (for example banana trees and plantations), *Rubiaceae* sp. (for example coffee), *Theaceae* sp., *Sterculiceae* sp., *Rutaceae* sp. (for example lemons, oranges and grapefruit); *Solanaceae* sp. (for example tomatoes), *Liliaceae* sp., *Asteraceae* sp. (for example lettuce), *Umbelliferae* sp., *Cruciferae* sp., *Chenopodiaceae* sp.,

*Cucurbitaceae* sp. (for example cucumber), *Alliaceae* sp. (for example leek, onion), *Papilionaceae* sp. (for example peas); major crop plants, such as *Gramineae* sp. (for example maize, turf, cereals such as wheat, rye, rice, barley, oats, millet and triticale), *Asteraceae* sp. (for example sunflower), *Brassicaceae* sp. (for example white cabbage, red cabbage, broccoli, cauliflower, Brussels sprouts, pak choi, kohlrabi, radishes, and oilseed rape, mustard, horseradish and cress), *Fabacae* sp. (for example bean, peanuts), *Papilionaceae* sp. (for example soya bean), *Solanaceae* sp. (for example potatoes), *Chenopodiaceae* sp. (for example sugar beet, fodder beet, swiss chard, beetroot); useful plants and ornamental plants for gardens and wooded areas; and genetically modified varieties of each of these plants.

Plants and plant cultivars which may be treated by the above disclosed methods include plants and plant cultivars which are resistant against one or more biotic stresses, i.e. said plants show a better defense against animal and microbial pests, such as against nematodes, insects, mites, phytopathogenic fungi, bacteria, viruses and/or viroids.

Plants and plant cultivars which may be treated by the above disclosed methods include those plants which are resistant to one or more abiotic stresses. Abiotic stress conditions may include, for example, drought, cold temperature exposure, heat exposure, osmotic stress, flooding, increased soil salinity, increased mineral exposure, ozone exposure, high light exposure, limited availability of nitrogen nutrients, limited availability of phosphorus nutrients, shade avoidance.

Plants and plant cultivars which may be treated by the above disclosed methods include those plants characterized by enhanced yield characteristics. Increased yield in said plants may be the result of, for example, improved plant physiology, growth and development, such as water use efficiency, water retention efficiency, improved nitrogen use, enhanced carbon assimilation, improved photosynthesis, increased germination efficiency and accelerated maturation. Yield may furthermore be affected by improved plant architecture (under stress and non-stress conditions), including but not limited to, early flowering, flowering control for hybrid seed production, seedling vigor, plant size, internode number and distance, root growth, seed size, fruit size, pod size, pod or ear number, seed number per pod or ear, seed mass, enhanced seed filling, reduced seed dispersal, reduced pod dehiscence and lodging resistance.

Further yield traits include seed composition, such as carbohydrate content and composition for example cotton or starch, protein content, oil content and composition, nutritional value, reduction in anti-nutritional compounds, improved processability and better storage stability.

Plants and plant cultivars which may be treated by the above disclosed methods include plants and plant cultivars which are hybrid plants that already express the characteristic of heterosis or hybrid vigor which results in generally higher yield, vigor, health and resistance towards biotic and abiotic stresses.

Plants and plant cultivars (obtained by plant biotechnology methods such as genetic engineering) which may be treated by the above disclosed methods include plants and plant cultivars which are herbicide-tolerant plants, i.e. plants made tolerant to one or more given herbicides. Such plants can be obtained either by genetic transformation, or by selection of plants containing a mutation imparting such herbicide tolerance.

Plants and plant cultivars (obtained by plant biotechnology methods such as genetic engineering) which may be treated by the above disclosed methods include plants and plant cultivars which are insect-resistant transgenic plants, i.e. plants made resistant to attack by certain target insects. Such plants can be obtained by genetic transformation, or by selection of plants containing a mutation imparting such insect resistance.

Plants and plant cultivars (obtained by plant biotechnology methods such as genetic engineering) which may be treated by the above disclosed methods include plants and plant cultivars which are disease-resistant transgenic plants, i.e. plants made resistant to attack by certain target insects. Such plants can be obtained by genetic transformation, or by selection of plants containing a mutation imparting such insect resistance.

Plants and plant cultivars (obtained by plant biotechnology methods such as genetic engineering) which may be treated by the above disclosed methods include plants and plant cultivars which are tolerant to abiotic stresses. Such plants can be obtained by genetic transformation, or by selection of plants containing a mutation imparting such stress resistance.

Plants and plant cultivars (obtained by plant biotechnology methods such as genetic engineering) which may be treated by the above disclosed methods include plants and plant cultivars which show altered quantity, quality and/or storage-stability of the harvested product and/or altered properties of specific ingredients of the harvested product.

Plants and plant cultivars (obtained by plant biotechnology methods such as genetic engineering) which may be treated by the above disclosed methods include plants and plant cultivars, such as cotton plants, with altered fiber characteristics. Such plants can be obtained by genetic transformation, or by selection of plants contain a mutation imparting such altered fiber characteristics.

Plants and plant cultivars (obtained by plant biotechnology methods such as genetic engineering) which may be treated by the above disclosed methods include plants and plant cultivars, such as oilseed rape or related *Brassica* plants, with altered oil profile characteristics. Such plants can be obtained by genetic transformation, or by selection of plants contain a mutation imparting such altered oil profile characteristics.

Plants and plant cultivars (obtained by plant biotechnology methods such as genetic engineering) which may be treated by the above disclosed methods include plants and plant cultivars, such as oilseed rape or related *Brassica* plants, with altered seed shattering characteristics. Such plants can be obtained by genetic transformation, or by selection of plants contain a mutation imparting such altered seed shattering characteristics and include plants such as oilseed rape plants with delayed or reduced seed shattering.

Plants and plant cultivars (obtained by plant biotechnology methods such as genetic engineering) which may be treated by the above disclosed methods include plants and plant cultivars, such as Tobacco plants, with altered post-translational protein modification patterns.

Aspects of the present teaching may be further understood in light of the following examples, which should not be construed as limiting the scope of the present teaching in any way.

Examples

Synthesis of Compounds of Formula (I)

Preparation Example 1: Preparation of ethyl N-[(4,5-dichloro-3-methyl-2-thienyl)carbonyl]glycinate (Compound 1.03)

Step 1: Preparation of methyl 3-amino-4,5-dichlorothiophene-2-carboxylate 1.35 g (5.04 mmol) of methyl 3-acetamido-4,5-dichlorothiophene-2-carboxylate was dissolved in a mixture of 2.1 mL (25.18 mmol) of a 37% (w/w) aqueous hydrochloric acid solution and 8.2 mL of methanol. The mixture was heated at 75° C. for 3 hours. The cooled reaction mixture was treated with a 30% (w/w) sodium hydroxide solution at 0° C. The resulting solution was extracted with ethyl acetate. Combined organic layers were dried over magnesium sulfate, filtered and concentrated under reduced pressure to yield 812 mg (98% purity, 70% yield) of methyl 3-amino-4,5-dichlorothiophene-2-carboxylate as a brown solid used as such in the next step. Log P=3.11. (M+H)=226.

Step 2: Preparation of methyl 3-bromo-4,5-dichlorothiophene-2-carboxylate

To a solution of 763 mg (3.41 mmol) of copper bromide (II) and 0.53 mL (90% purity, 3.99 mmol) of tert-butyl nitrite in 10.5 mL of anhydrous acetonitrile was added portion wise 600 mg (88% purity, 2.33 mmol) of methyl 3-amino-4,5-dichlorothiophene-2-carboxylate at 0° C. After gas evolved, the solution was stirred at room temperature for 18 hours. The reaction mixture was diluted with ethyl acetate and acidified with a 1 M aqueous hydrochloric acid solution. The aqueous layer was extracted three times with ethyl acetate. Combined organic layers were dried over magnesium sulfate, filtered and concentrated under reduced pressure. The residue was purified by column chromatography on silica gel (gradient n-heptane/ethyl acetate) to yield 563 mg (98% purity, 82% yield) of methyl 3-bromo-4,5-dichlorothiophene-2-carboxylate as a yellow solid. Log P=3.99. (M+H)=288.

Step 3: Preparation of 3-bromo-4,5-dichlorothiophene-2-carboxylic acid (Compound VIIIa.03)

To a solution of 250 mg (0.86 mmol) of methyl 3-bromo-4,5-dichlorothiophene-2-carboxylate in 5 mL of tetrahydrofuran was added dropwise 1 mL of a 1.9 M aqueous potassium hydroxide solution (1.9 mmol). The reaction was stirred at room temperature for 18 hours. The reaction mixture was diluted with ethyl acetate, water and a saturated aqueous sodium bicarbonate solution. The organic layer was washed twice with a saturated aqueous sodium bicarbonate solution. Combined aqueous layers were carefully acidified with a 37% (w/w) aqueous hydrochloric acid solution at 0° C. and extracted with ethyl acetate. Combined organic layers were dried over magnesium sulfate, filtered and concentrated under reduced pressure to yield 219 mg (96% purity, 88% yield) of 3-bromo-4,5-dichlorothiophene-2-carboxylic acid as a white solid. Log P=2.51. (M−H)=273.

Step 4: Preparation of ethyl N-[(3-bromo-4,5-dichloro-2-thienyl)carbonyl]glycinate (Compound VIa.01)

In a 5 mL microwave vial under inert atmosphere, a solution of 157 mg (0.93 mmol) of 2-chloro-1,3-dimethylimidazolidinium chloride dissolved in 3 mL of dichloromethane was added over a solution of 197 mg (0.72 mmol) of 3-bromo-4,5-dichlorothiophene-2-carboxylic acid and 0.54 mL (3.07 mmol) of N,N-diisopropylethylamine dissolved in 7 mL of dichloromethane. After 5 min of stirring, 200 mg (1.43 mmol) of ethyl glycinate hydrochloride (1:1) was added and the reaction mixture was stirred at room temperature for 20 hours. The reaction mixture was quenched with water and extracted with dichloromethane. Combined organic layers were dried over magnesium sulfate, filtered and concentrated under reduced pressure. The residue was purified by column chromatography on silica gel (gradient n-heptane/ethyl acetate) to yield 209 mg (100% purity, 81% yield) of ethyl N-[(3-bromo-4,5-dichloro-2-thienyl)carbonyl]glycinate as a white solid. Log P=3.33. (M+H)=360.

Step 5: Preparation of ethyl N-[(4,5-dichloro-3-methyl-2-thienyl)carbonyl]glycinate (Compound 1.03)

In a 5 mL microwave vial under inert atmosphere, 100 mg (0.27 mmol) of ethyl N-[(3-bromo-4,5-dichloro-2-thienyl)carbonyl]glycinate, 25 mg (0.41 mmol) of methylboronic acid, 3.1 mg (0.01 mmol) of palladium(II) acetate, 7.8 mg (0.02 mmol) of tricyclohexylphosphine and 206 mg (0.96 mmol) of potassium phosphate tribasic were successively added followed by degassed toluene (1.25 mL) and water (0.13 mL). The vial was sealed and the reaction mixture was stirred at 100° C. for 18 hours. The reaction mixture was diluted with water and extracted with dichloromethane. Combined organic layers were filtered through a Chem Elut™ cartridge and concentrated under reduced pressure. The residue was purified by preparative high performance liquid chromatography (gradient acetonitrile/aqueous solution of formic acid (1%)) to yield 38 mg (100% purity, 46% yield) of ethyl N-[(4,5-dichloro-3-methyl-2-thienyl)carbonyl]glycinate as a white solid. Log P=2.95. (M+H)=296.

Preparation Example 2: Preparation of ethyl N-[(4,5-dibromo-3-methyl-2-thienyl)carbonyl]-valinate (Compound 1.04)

To a solution of 154 mg (0.50 mmol) of 4,5-dibromo-3-methylthiophene-2-carboxylic acid and 183 mg (1.00 mmol) of DL-valine ethyl ester hydrochloride dissolved in 3 mL of tetrahydrofuran was added 0.21 mL (1.51 mmol) of triethylamine followed by 0.45 mL (0.75 mmol) of a 50% (w/w) propanephosphonic anhydride solution in ethyl acetate. The reaction mixture was stirred at room temperature for 2 hours. The reaction mixture was quenched with a saturated aqueous solution of sodium bicarbonate and extracted with ethyl acetate. Combined organic layers were dried over magnesium sulfate, filtered and concentrated under reduced pressure. The residue was purified by column chromatography on silica gel (gradient n-heptane/ethyl acetate) to yield 103 mg (95% purity, 45% yield) of ethyl N-[(4,5-dibromo-3-methyl-2-thienyl)carbonyl]-valinate as a white solid. Log P=4.32. (M+H)=426.

Preparation Example 3: Preparation of N-[(4,5-dibromo-3-methyl-2-thienyl)carbonyl]-valine (Compound 1.07)

To a solution of 164 mg (0.38 mmol) of ethyl N-[(4,5-dibromo-3-methyl-2-thienyl)carbonyl]-valinate and in 3 mL of tetrahydrofuran was added dropwise 0.81 mL of a 1 M lithium hydroxide solution (0.81 mmol). The reaction was stirred at room temperature for 18 hours. The reaction mixture was diluted with ethyl acetate and a saturated aqueous sodium bicarbonate solution. The organic layer was washed twice with a saturated aqueous sodium bicarbonate solution. Combined aqueous layers were carefully acidified with a 37% (w/w) aqueous hydrochloric acid solution at 0° C. and extracted with ethyl acetate. Combined organic layers were dried over magnesium sulfate, filtered and concentrated under reduced pressure to yield 151 mg (98% purity, 96% yield) of N-[(4,5-dibromo-3-methyl-2-thienyl)carbonyl]-valine as a white solid. Log P=2.92. (M+H)=398.

Preparation Example 4: Preparation of ethyl 1-{[(4,5-dibromo-3-methyl-2-thienyl)carbonyl]amino}cyclopropanecarboxylate (Compound I.01)

To a solution of 200 mg (0.60 mmol) of ethyl 1-{[(4-bromo-3-methyl-2-thienyl)carbonyl]amino}cyclopropanecarboxylate (compound IXa.01) in 6 mL of anhydrous N,N-dimethylformamide was added 129 mg (0.72 mmol) of N-bromosuccinimide. The reaction was stirred at 50° C. for 18 hours. The reaction mixture was partitioned between ethyl acetate and water and extracted with ethyl acetate. Combined organic layers were filtered through a Chem Elut™ cartridge and concentrated under reduced pressure. The residue was purified by preparative high performance liquid chromatography (gradient acetonitrile/aqueous solution of formic acid (1%)) to yield 148 mg (100% purity, 60% yield) of ethyl 1-{[(4,5-dibromo-3-methyl-2-thienyl)carbonyl]amino}cyclopropanecarboxylate as a white solid. Log P=3.22. (M+H)=410.

Preparation Example 5: Preparation of ethyl 1-{[(4,5-dibromo-3-methyl-2-thienyl)carbonyl]amino}cyclopropanecarboxylate (Compound I.01)

Step 1: Preparation of ethyl 1-[({4-bromo-5-[(tert-butoxycarbonyl)amino]-3-methyl-2-thienyl}carbonyl)amino]cyclopropanecarboxylate (Compound XIa.01)

To a solution of 92 mg (0.27 mmol) of 4-bromo-5-[(tert-butoxycarbonyl)amino]-3-methylthiophene-2-carboxylic acid (compound XIIIa.02) and 67 mg (0.41 mmol) of ethyl 1-aminocyclopropanecarboxylate hydrochloride dissolved in 1.4 mL of dichloromethane was added 0.14 mL (0.82 mmol) of N,N-diisopropylethylamine followed by 135 mg (0.35 mmol) of 1-[bis(dimethylamino)methylene]-1H-1,2,3-triazolo[4,5-b]pyridinium 3-oxid hexafluorophosphate. The reaction mixture was stirred at room temperature for 3.5 hours. The reaction mixture was quenched with water and extracted with dichloromethane. Combined organic layers were filtered through a Chem Elut™ cartridge and concentrated under reduced pressure. The residue was purified by column chromatography on silica gel (gradient n-heptane/ethyl acetate) to yield 95 mg (93% purity, 72% yield) of ethyl 1-[({4-bromo-5-[(tert-butoxycarbonyl)amino]-3-methyl-2-thienyl}carbonyl)amino]cyclopropanecarboxylate as an orange solid. Log P=3.28. (M+H)=447.

Step 2: Preparation of ethyl 1-{[(5-amino-4-bromo-3-methyl-2-thienyl)carbonyl]amino}cyclopropanecarboxylate (Compound Xa.01)

To a solution of 60 mg (0.13 mmol) of 1-[(tert-butoxycarbonyl)amino]-3-methyl-2-thienyl)carbonyl)amino]cyclopropanecarboxylate in 0.60 mL of chloroform was added 0.62 mL of trifluoroacetic acid. The reaction was stirred at room temperature for 18 hours. The reaction mixture was diluted with toluene and concentrated under reduced pressure. The residue was purified by preparative high performance liquid chromatography (gradient acetonitrile/aqueous solution of ammonium acetate (1 mM)) to yield 35 mg (100% purity, 74% yield) of ethyl 1-{[(5-amino-4-bromo-3-methyl-2-thienyl)carbonyl]amino}cyclopropanecarboxylate as a white solid. Log P=1.92. (M+H)=347.

Step 3: Preparation of ethyl 1-{[(4,5-dibromo-3-methyl-2-thienyl)carbonyl]amino}cyclopropanecarboxylate (Compound I.01)

To a solution of copper(II) bromide (28.9 mg, 0.13 mmol) in 0.5 mL of anhydrous acetonitrile was added dropwise tert-butyl nitrite (17 µL, 0.13 mmol) at 0° C. The reaction mixture was allowed to warm to room temperature before dropwise addition of a solution of 30 mg (0.08 mmol) of ethyl 1-{[(5-amino-4-bromo-3-methyl-2-thienyl)carbonyl]amino}cyclopropanecarboxylate in 0.7 mL of anhydrous acetonitrile. The reaction mixture was stirred at room temperature for 2 hours. The reaction mixture was diluted with ethyl acetate and carefully acidified with a 1 M aqueous hydrochloric acid solution. The aqueous layer was extracted three times with ethyl acetate. Combined organic layers were dried over magnesium sulfate, filtered and concentrated under reduced pressure. The residue was purified column chromatography on silica gel (gradient n-heptane/ethyl acetate) to yield 11 mg (100% purity, 31% yield) of ethyl 1-{[(4,5-dibromo-3-methyl-2-thienyl)carbonyl]amino}cyclopropanecarboxylate as a white solid. Log P=3.19. (M+H)=410.

Exemplary Compounds

The exemplary compounds according to the invention as shown in tables I.1, I.2, I.3, I.4, I.5, I.6 and I.7 were prepared in analogy with the examples provided above and/or in accordance with the general description of the processes herein disclosed. The exemplary compounds are racemic unless specified differently.

The following table I.1 illustrates in a non-limiting manner examples of compounds according to formula (I).

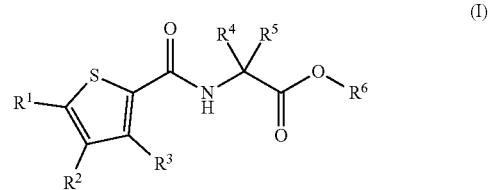

(I)

TABLE I.1

| Ex. No | R¹ | R² | R³ | R⁴ | R⁵ | R⁶ | LogP | Enantiomer | Optical Rotation* |
|---|---|---|---|---|---|---|---|---|---|
| I.01 | Br | Br | Me | —CH$_2$—CH$_2$— | | Et | 3.19[a] | | |
| I.02 | Br | Br | Me | H | H | Et | 3.02[a] | | |
| I.03 | Cl | Cl | Me | H | H | Et | 2.90[a] | | |
| I.04 | Br | Br | Me | isopropyl | H | Et | 4.32[a] | | |
| I.05 | Br | Br | Me | 2-methylpropyl | H | Et | 4.56[a] | | |
| I.06 | Br | Br | Me | —CH$_2$—CH$_2$— | | H | 2.25[a] | | |
| I.07 | Br | Br | Me | isopropyl | H | H | 2.92[a] | | |
| I.08 | Br | Br | Me | propan-2-yl | H | Et | 4.32[a] | (S) | +22.1° (c = 0.99, CH2Cl2, 20° C.) |
| I.09 | Br | Br | Me | H | H | Me | 2.64[a] | | |
| I.10 | Br | Br | Me | H | H | H | 2.05[a] | | |
| I.11 | Br | Br | Me | propan-2-yl | H | Me | 3.87[a] | (S) | +3.6° (c = 1.13, MeOH, 25° C.) |
| I.12 | Br | Br | Me | isopropyl | H | (Z)-hex-3-en-1-yl | 5.75[a] | | |
| I.13 | Br | Br | Me | isopropyl | H | prop-2-yn-1-yl | 4.06[a] | | |
| I.14 | Br | Br | Me | isopropyl | H | 2-methylpropyl | 5.22[a] | | |
| I.15 | Br | Br | Me | isopropyl | H | cyanomethyl | 3.69[a] | | |
| I.16 | Br | Br | Me | isopropyl | H | oxetan-3-yl | 3.58[a] | | |
| I.17 | Br | Br | Me | isopropyl | H | thietan-3-yl | 4.67[a] | | |
| I.18 | Br | Br | Me | isopropyl | H | 1,1-dioxothietan-3-yl | 3.42[a] | | |
| I.19 | Br | Br | Me | isopropyl | H | oxolan-3-yl | 3.78[a] | | |
| I.20 | Br | Br | Me | isopropyl | H | trimethylsilylmethyl | 5.78[a] | | |
| I.21 | Br | Br | Me | Me | H | Et | 3.39[a] | | |
| I.22 | Br | Br | Me | butan-2-yl | H | Me | 4.30[a] | (2S, 3S) | |
| I.23 | Br | Br | Me | (4-hydroxyphenyl)methyl | H | Et | 3.33[a] | | |
| I.24 | Cl | Cl | Me | 2-methylsulfanylethyl | H | Et | 3.94[a] | (S) | +26.4° (c = 1.06, CDCl3, 25° C.) |
| I.25 | Cl | Cl | Me | isopropyl | H | Et | 4.23[a] | (S) | +44.7° (c = 1.08, CDCl3, 25° C.) |
| I.26 | Cl | Cl | Me | benzyl | H | Et | 4.46[a] | (S) | +91° (c = 1.06, CDCl3, 25° C.) |
| I.27 | Cl | Cl | Me | Me | H | Et | 3.31[a] | | |
| I.28 | Cl | Cl | Me | H | H | tert-butyl | 3.77[a] | | |
| I.29 | Cl | Cl | Me | isopropyl | H | Me | 3.79[a] | (S) | +40° (c = 1, CDCl3, 25° C.) |
| I.30 | Cl | Cl | Me | 2-methylsulfanylethyl | H | Me | 3.55[a] | (S) | +30.8° (c = 1.04, CDCl3, 25° C.) |
| I.31 | Cl | Cl | Me | H | H | Me | 2.51[a] | | |
| I.32 | Cl | Cl | Me | butan-2-yl | H | Me | 4.23[a] | (2S, 3S) | +46.9° (c = 1.07, CDCl3, 25° C.) |
| I.33 | Cl | Cl | Me | 2-methylpropyl | H | Et | 4.54[a] | (S) | +29.4° (c = 1.02, CDCl3, 25° C.) |
| I.34 | Cl | Cl | Me | H | H | benzyl | 3.76[a] | | |
| I.35 | Cl | Cl | Me | 2-methylsulfanylethyl | H | Me | 3.55[a] | | |
| I.36 | Cl | Cl | Me | 2-methylsulfanylethyl | H | Me | 3.55[a] | (R) | |
| I.37 | Cl | Cl | Me | 2-methylpropyl | H | Et | 4.51[a] | | |
| I.38 | Cl | Cl | Me | benzyl | H | Et | 4.46[a] | | |
| I.39 | Cl | Cl | Me | (4-hydroxyphenyl)methyl | H | Et | 3.29[a] | | |
| I.40 | Cl | Cl | Me | isopropyl | H | Et | 4.23[a] | | |
| I.41 | Cl | Cl | Me | H | H | isopropyl | 3.29[a] | | |
| I.42 | Cl | Cl | Me | Me | H | Et | 3.31[a] | (R) | |
| I.43 | Cl | Cl | Me | —CH$_2$—CH$_2$— | | Et | 3.08[a] | (R) | |
| I.44 | Cl | Cl | Me | isopropyl | H | Et | 4.23[a] | (R) | −48.4° (c = 1.08, CDCl3, 25° C.) |
| I.45 | Cl | Cl | Me | benzyl | H | Et | 4.46[a] | (R) | −91.2° (c = 1.08, CDCl3, 25° C.) |
| I.46 | Cl | Cl | Me | isopropyl | H | Me | 3.79[a] | (R) | |
| I.47 | Cl | Cl | Me | 2-methylsulfanylethyl | H | Et | 3.94[a] | | |
| I.48 | Cl | Cl | Me | H | H | propyl | 3.35[a] | | |
| I.49 | Br | Br | Me | isopropyl | H | isopropyl | 4.77[a] | | |
| I.50 | Cl | Cl | Me | —CH$_2$—CH$_2$— | | Me | 2.75[a] | | |
| I.51 | Cl | Cl | Me | —CH$_2$—CH$_2$— | | H | 2.26[a] | | |
| I.52 | Br | Br | Me | isopropyl | H | cyclopropylmethyl | 4.80[a] | | |
| I.53 | Br | Br | Me | isopropyl | H | cyclobutyl | 4.98[a] | | |
| I.54 | Br | Br | Me | isopropyl | H | propyl | 4.77[a] | | |
| I.55 | Br | Br | Me | isopropyl | H | butyl | 5.25[a] | | |
| I.56 | Br | Br | Me | isopropyl | H | cyclopropyl | 4.37[a] | | |
| I.57 | Br | Br | Me | isopropyl | H | benzyl | 5.03[a] | | |
| I.58 | Br | Br | Me | isopropyl | H | allyl | 4.46[a] | | |
| I.59 | Br | Br | Me | isopropyl | H | 2,2,2-trifluoroethyl | 4.51[a] | | |
| I.60 | Br | Br | Me | isopropyl | H | phenyl | 4.85[a] | | |
| I.61 | Br | Br | Me | isopropyl | H | tert-butyl | 5.25[a] | | |
| I.62 | Br | Br | Me | propan-2-yl | H | Et | 4.37[a] | (R) | −44.4° (c = 1.04, CDCl3, 25° C.) |
| I.63 | Br | Br | Me | propan-2-yl | H | Me | 3.91[a] | (R) | |
| I.64 | Br | Br | Me | isopropyl | H | Me | 3.91[a] | | |
| I.65 | Br | Br | Me | benzyl | H | Et | 4.59[a] | (R) | −64.1° (c = 1.41, CDCl3, 25° C.) |
| I.66 | Br | Br | Me | benzyl | H | Et | 4.59[a] | (S) | +58° (c = 1, CDCl3, 25° C.) |
| I.67 | Br | Br | Me | benzyl | H | Et | 4.59[a] | | |
| I.68 | Br | Br | Me | 2-methylpropyl | H | Et | 4.66[a] | (R) | −28° (c = 1, CDCl3, 25° C.) |
| I.69 | Br | Br | Me | 2-methylpropyl | H | Et | 4.66[a] | (S) | +26° (c = 1, CDCl3, 25° C.) |
| I.70 | Br | Br | Me | 2-methylsulfanylethyl | H | Me | 3.69[a] | (R) | |
| I.71 | Br | Br | Me | 2-methylsulfanylethyl | H | Me | 3.69[a] | (S) | +26° (c = 1, CDCl3, 25° C.) |
| I.72 | Br | Br | Me | 2-methylsulfanylethyl | H | Me | 3.69[a] | | |
| I.73 | Cl | Cl | Me | benzyl | H | Me | 4.12[a] | (S) | |
| I.74 | Cl | Cl | Me | 2-methylpropyl | H | Et | 4.59[a] | (R) | |
| I.75 | Cl | Cl | Me | phenyl | H | Et | 4.37[a] | | |
| I.76 | Br | Br | Me | phenyl | H | Et | 4.44[a] | | |
| I.77 | Br | Br | Me | H | H | oxan-4-yl | 2.86[a] | | |
| I.78 | Br | Br | Me | H | H | isopropyl | 3.40[a] | | |

TABLE I.1-continued

| Ex. No | R¹ | R² | R³ | R⁴ | R⁵ | R⁶ | LogP | Enantiomer | Optical Rotation* |
|---|---|---|---|---|---|---|---|---|---|
| I.79 | Br | Br | Me | Me | H | H | 2.39[a] | | |
| I.80 | Cl | Cl | Me | H | H | H | 2.05[a] | | |
| I.81 | Cl | Cl | Me | Me | H | H | 2.28[a] | | |
| I.82 | Cl | Cl | Me | isopropyl | H | H | 2.96[a] | | |
| I.83 | Cl | Cl | Me | butan-2-yl | H | H | 3.31[a] | (2S, 3S) | +12.9° C. (c = 1.4, DMSO, 25° C.) |
| I.84 | Cl | Cl | Me | 2-methylpropyl | H | H | 3.31[a] | | |
| I.85 | Cl | Cl | Me | 2-methylsulfanylethyl | H | H | 2.80[a] | | |
| I.86 | Cl | Cl | Me | benzyl | H | H | 3.31[a] | | |
| I.87 | Br | Br | Me | 2-methylsulfanylethyl | H | H | 2.89[a] | | |
| I.88 | Br | Br | Me | benzyl | H | H | 3.30[a] | | |
| I.89 | Br | Br | Me | butan-2-yl | H | H | 3.37[a] | (2S, 3S) | +14.3° (c = 1.40, MeOH, 20° C.) |
| I.90 | Br | Br | Me | 2-methylpropyl | H | H | 3.34[a] | | |
| I.91 | Cl | Cl | Me | isopropyl | H | Me | 4.34[a] | | |
| I.92 | Br | Br | Me | —CH₂—CH₂— | | Me | 2.86[a] | | |

Note:
Me: methyl, Et: ethyl
*Optical rotation: concentration c is expressed in g/100 mL The following table I.2 illustrates in a non-limiting manner examples of intermediates according to formula (IVa).

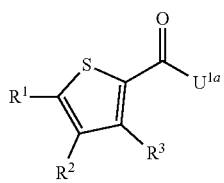

(IVa)

TABLE I.2

| Ex No | R¹ | R² | R³ | U¹ᵃ | LogP |
|---|---|---|---|---|---|
| IVa.01 | Br | Br | Me | 2-methylpropoxy | 6.12[a] |
| IVa.02 | Cl | Cl | Me | OEt | 4.80[a] |
| IVa.03 | Cl | Cl | Me | 2-methylpropoxy | 6.05[a] |

Note:
Me: methyl, Et: ethyl

The following table I.3 illustrates in a non-limiting manner examples of intermediates according to formula (VIa).

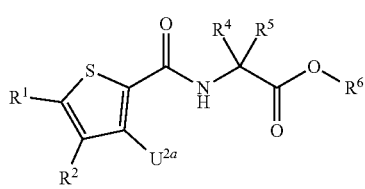

(VIa)

TABLE I.3

| Ex No | R¹ | R² | R⁴ | | R⁵ | R⁶ | U²ᵃ | LogP |
|---|---|---|---|---|---|---|---|---|
| VIa.01 | Cl | Cl | H | | H | Et | Br | 3.33[a] |
| VIa.02 | Cl | Cl | H | | H | Me | I | 2.90[a] |
| VIa.03 | Br | Br | H | | H | Me | I | 2.96[a] |
| VIa.04 | Cl | Cl | —CH₂—CH₂— | | | Et | Br | 3.45[a] |
| VIa.05 | Cl | Cl | —CH₂—CH₂— | | | Et | I | 3.39[a] |
| VIa.06 | Cl | Cl | —CH₂—CH₂— | | | H | I | 2.34[a] |
| VIa.07 | Br | Br | —CH₂—CH₂— | | | Et | I | 3.41[a] |
| VIa.08 | Br | Br | —CH₂—CH₂— | | | Me | I | 3.06[a] |
| VIa.09 | Br | Br | —CH₂—CH₂— | | | H | I | 2.43[a] |
| VIa.10 | Br | Br | H | | H | Et | I | 3.35[a] |
| VIa.11 | Br | Br | isopropyl | | H | Et | I | 4.78[a] |
| VIa.12 | Cl | Cl | H | | H | Et | I | 3.31[a] |
| VIa.13 | Cl | Cl | H | | H | H | I | 2.21[a] |
| VIa.14 | Br | Br | benzyl | | H | Et | I | 4.93[a] |
| VIa.15 | Br | Br | 2-methylpropyl | | H | Et | I | 5.01[a] |
| VIa.16 | Br | Br | 2-methylsulfanylethyl | | H | Et | I | 4.37[a] |
| VIa.17 | Cl | Cl | isopropyl | | H | Et | Br | 4.88[a] |
| VIa.18 | Cl | Cl | 2-methylpropyl | | H | Et | Br | 5.17[a] |
| VIa.19 | Cl | Cl | 2-methylsulfanylethyl | | H | Et | Br | 4.46[a] |
| VIa.20 | Cl | Cl | benzyl | | H | Et | Br | 5.01[a] |
| VIa.21 | Cl | Cl | isopropyl | | H | Et | I | 4.85[a] |
| VIa.22 | Cl | Cl | 2-methylpropyl | | H | Et | I | 5.08[a] |
| VIa.23 | Cl | Cl | 2-methylsulfanylethyl | | H | Et | I | 4.40[a] |
| VIa.24 | Cl | Cl | benzyl | | H | Et | I | 5.00[a] |

Note:
Me: methyl, Et: ethyl

The following table I.4 illustrates in a non-limiting manner examples of intermediates according to formula (VIIIa).

(VIIIa)

TABLE I.4

| Ex No | R¹ | R² | U²ᵃ | U¹ᵃ | LogP |
|---|---|---|---|---|---|
| VIIIa.01 | Cl | Cl | I | OEt | 4.73[b] |
| VIIIa.02 | Cl | Cl | Br | OMe | 4.11[a] |
| VIIIa.03 | Cl | Cl | Br | OH | 2.52[a] |
| VIIIa.04 | Br | Br | I | OMe | 4.20[a] |
| VIIIa.05 | Cl | Cl | I | OMe | 4.15[a] |
| VIIIa.06 | Cl | Cl | I | OH | 2.64[a] |
| VIIIa.07 | Br | Br | I | OEt | 4.78[a] |
| VIIIa.08 | Cl | Cl | Br | OEt | 4.58[a] |

Note:
Me: methyl, Et: ethyl

The following table I.5 illustrates in a non-limiting manner examples of intermediates according to formula (IXa) and (IXb).

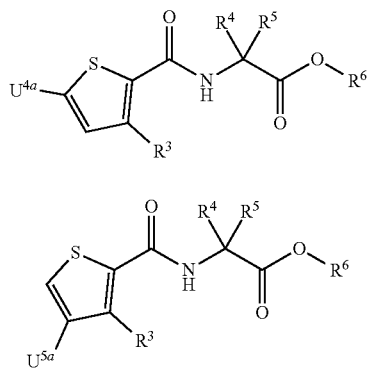

(IXa)

(IXb)

TABLE I.5

| Ex No | R³ | R⁴ | R⁵ | R⁶ | U⁴ᵃ | U⁵ᵃ | LogP |
|---|---|---|---|---|---|---|---|
| IXa.01 | Me | —CH₂—CH₂— | | Et | Br | | 2.57[a] |
| IXa.02 | Me | H | H | Et | Br | | 2.39[a] |
| IXa.03 | Me | isopropyl | H | Et | Br | | 3.65[a] |
| IXa.04 | Me | benzyl | H | Et | Br | | 3.90[a] |
| IXb.01 | Me | —CH₂—CH₂— | | Et | | Br | 2.49[a] |

Note:
Me: methyl, Et: ethyl

The following table I.6 illustrates in a non-limiting manner examples of intermediates according to formula (Xa) and (XIa).

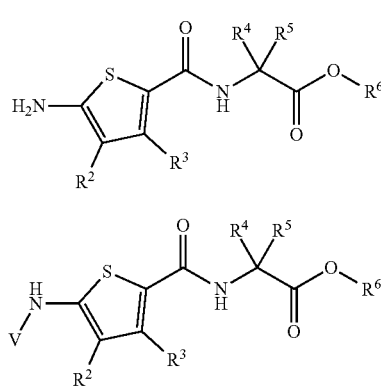

(Xa)

(XIa)

TABLE I.6

| Ex No | R² | R³ | R⁴ | R⁵ | R⁶ | V | LogP |
|---|---|---|---|---|---|---|---|
| Xa.01 | Br | Me | —CH₂—CH₂— | | Et | | 1.97[a] |
| XIa.01 | Br | Me | —CH₂—CH₂— | | Et | tert-butoxycarbonyl | 3.44[b] |

Note:
Me: methyl, Et: ethyl

The following table I.7 illustrates in a non-limiting manner examples of intermediates according to formula (XIIIa).

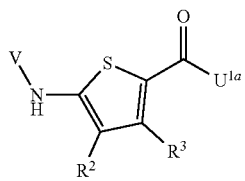

(XIIIa)

TABLE I.7

| Ex No | R² | R³ | U¹ᵃ | V | LogP |
|---|---|---|---|---|---|
| XIIIa.01 | Br | Me | OEt | tert-butoxycarbonyl | 4.62[a] |
| XIIIa.02 | Br | Me | OH | tert-butoxycarbonyl | 2.86[a] |

Note:
Me: methyl, Et: ethyl

In the above tables, measurement of Log P values was performed according to EEC directive 79/831 Annex V.A8 by HPLC (High Performance Liquid Chromatography) on reversed phase columns with the following methods:

[a] Log P value is determined by measurement of LC-UV, in an acidic range, with 0.1% formic acid in water and acetonitrile as eluent (linear gradient from 10% acetonitrile to 95% acetonitrile).

[b] Log P value is determined by measurement of LC-UV, in a neutral range, with 0.001 molar ammonium acetate solution in water and acetonitrile as eluent (linear gradient from 10% acetonitrile to 95% acetonitrile).

[c] Log P value is determined by measurement of LC-UV, in an acidic range, with 0.1% phosphoric acid and acetonitrile as eluent (linear gradient from 10% acetonitrile to 95% acetonitrile).

If more than one Log P value is available within the same method, all the values are given and separated by "+".

Calibration was done with straight-chain alkan2-ones (with 3 to 16 carbon atoms) with known Log P values (measurement of Log P values using retention times with linear interpolation between successive alkanones). Lambda-max-values were determined using UV-spectra from 200 nm to 400 nm and the peak values of the chromatographic signals.

NMR-Peak Lists

Table A provides the NMR data ($^1$H) of some compounds disclosed in the above tables.

1H-NMR data of selected examples are written in form of 1H-NMR-peak lists. To each signal peak are listed the δ-value in ppm and the signal intensity in round brackets. Between the δ-value—signal intensity pairs are semicolons as delimiters.

The peak list of an example has therefore the form:
$\delta_1$ (intensity$_1$); $\delta_2$ (intensity$_2$); . . . ; $\delta_i$ (intensity$_i$); . . . ; $\delta_n$ (intensity$_n$)

Intensity of sharp signals correlates with the height of the signals in a printed example of a NMR spectrum in cm and shows the real relations of signal intensities. From broad signals, several peaks or the middle of the signal and their relative intensity in comparison to the most intensive signal in the spectrum can be shown.

For calibrating chemical shift for 1H spectra, we use tetramethylsilane and/or the chemical shift of the solvent used, especially in the case of spectra measured in DMSO. Therefore, in NMR peak lists, tetramethylsilane peak can occur but not necessarily.

The 1H-NMR peak lists are similar to classical 1H-NMR prints and contains therefore usually all peaks, which are listed at classical NMR-interpretation.

Additionally they can show like classical 1H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-D6 and the peak of water are shown in our 1H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore, their peaks can help to recognize the reproduction of our preparation process via "side-products-fingerprints".

An expert, who calculates the peaks of the target compounds with known methods (MestreC, ACD-simulation, but also with empirically evaluated expectation values) can isolate the peaks of the target compounds as needed optionally using additional intensity filters. This isolation would be similar to relevant peak picking at classical 1H-NMR interpretation.

Further details of NMR-data description with peak lists you find in the publication "Citation of NMR Peaklist Data within Patent Applications" of the Research Disclosure Database Number 564025.

TABLE A

NMR peak lists

I.01: $^1$H-NMR(300.2 MHz, CDCl3):
δ = 7.2983 (5.4); 6.3048 (1.0); 4.2377 (1.2); 4.2139 (3.8); 4.1901 (3.8); 4.1664 (1.2); 2.5728 (16.0); 1.7079 (1.0); 1.6912 (2.9); 1.6804 (3.0); 1.6651 (1.3); 1.6024 (1.2); 1.3339 (1.3); 1.3188 (3.0); 1.3079 (3.1); 1.2970 (4.3); 1.2912 (1.6); 1.2732 (8.2); 1.2495 (3.9); 0.0356 (6.8)

I.02: $^1$H-NMR(300.2 MHz, CDCl3):
δ = 7.2987 (2.8); 6.3702 (0.5); 5.3358 (1.0); 4.3360 (1.1); 4.3122 (3.4); 4.2884 (3.5); 4.2646 (1.2); 4.2258 (4.6); 4.2093 (4.5); 2.5934 (16.0); 1.6227 (3.3); 1.3760 (4.2); 1.3522 (8.4); 1.3284 (4.0); 0.0353 (3.4)

I.03: $^1$H-NMR(400.2 MHz, $d_6$-DMSO):
δ = 8.6720 (0.4); 8.6579 (0.9); 8.6436 (0.4); 4.1518 (1.3); 4.1340 (4.0); 4.1163 (4.0); 4.0985 (1.3); 3.9757 (3.9); 3.9610 (3.9); 3.3498 (56.9); 2.5264 (0.4); 2.5215 (0.6); 2.5129 (6.9); 2.5085 (13.6); 2.5040 (17.5); 2.4994 (12.6); 2.4949 (6.0); 2.4038 (16.0); 1.2386 (0.4); 1.2239 (4.5); 1.2061 (9.2); 1.1883 (4.4)

I.04: $^1$H-NMR(499.9 MHz, $d_6$-DMSO):
δ = 8.5246 (2.1); 8.5091 (2.1); 4.2262 (2.0); 4.2121 (2.9); 4.2044 (0.6); 4.1971 (2.1); 4.1901 (1.4); 4.1827 (0.9); 4.1759 (1.4); 4.1684 (2.7); 4.1617 (0.5); 4.1542 (2.7); 4.1448 (0.9); 4.1400 (0.9); 4.1306 (2.7); 4.1231 (0.5); 4.1164 (2.7); 4.1089 (1.4); 4.1023 (0.9); 4.0947 (1.4); 4.0805 (0.4); 3.3228 (2.7); 2.5144 (1.0); 2.5109 (2.1); 2.5073 (2.8); 2.5037 (2.0); 2.5002 (0.9); 2.4121 (26.4); 2.1959 (0.3); 2.1822 (1.0); 2.1686 (1.8); 2.1550 (1.8); 2.1414 (1.1); 2.1278 (0.4); 1.2263 (7.8); 1.2120 (16.0); 1.1978 (7.7); 0.9722 (10.8); 0.9585 (11.5); 0.9537 (11.5); 0.9401 (10.5)

I.05: $^1$H-NMR(300.2 MHz, CDCl3):
δ = 7.2984 (1.5); 6.3390 (0.7); 6.3132 (0.9); 4.8070 (0.6); 4.7792 (1.2); 4.7623 (0.9); 4.7517 (0.7); 4.7355 (0.5); 4.2892 (1.4); 4.2654 (4.3); 4.2417 (4.4); 4.2179 (1.5); 2.5719 (4.2); 2.5621 (16.0); 1.7908 (0.9); 1.7725 (1.3); 1.7611 (1.3); 1.7538 (1.5); 1.7462 (1.9); 1.7253 (1.4); 1.7062 (0.9); 1.6863 (1.3); 1.6608 (1.0); 1.6564 (1.0); 1.6324 (0.7); 1.4570 (1.0); 1.3543 (5.0); 1.3305 (10.0); 1.3067 (5.1); 1.2917 (1.0); 1.2857 (1.0); 1.0435 (0.3); 1.0202 (6.9); 1.0065 (10.3); 0.9871 (6.6); 0.9283 (0.3); 0.9064 (0.7); 0.8832 (0.4); 0.0297 (0.4); 0.0254 (0.7)

I.06: $^1$H-NMR(499.9 MHz, $d_6$-DMSO):
δ = 12.4961 (2.0); 8.7878 (13.5); 3.3226 (11.2); 2.5437 (0.5); 2.5119 (15.4); 2.5084 (22.0); 2.5049 (17.8); 2.4800 (0.4); 2.4158 (70.6); 2.2841 (0.4); 2.0928 (6.3); 1.4392 (0.4); 1.4307 (0.4); 1.4239 (0.5); 1.4083 (5.6); 1.3989 (14.1); 1.3924 (16.0); 1.3839 (6.4); 1.3521 (0.6); 1.3056 (0.4); 1.2658 (0.7); 1.2420 (3.2); 1.2155 (0.4); 1.2021 (0.4); 1.1883 (0.6); 1.1763 (0.6); 1.1716 (0.8); 1.1622 (0.6); 1.1572 (1.2); 1.1482 (0.7); 1.1433 (0.7); 1.1222 (6.5); 1.1135 (14.8); 1.1070 (15.3); 1.0976 (5.6); 1.0670 (0.4); 0.8609 (0.5)

I.07: $^1$H-NMR(499.9 MHz, $d_6$-DMSO):
δ = 12.7425 (0.4); 8.3639 (2.1); 8.3478 (2.1); 4.2207 (2.0); 4.2080 (2.3); 4.2047 (2.2); 4.1920 (2.0); 3.5752 (2.1); 3.3269 (0.8); 2.5162 (1.6); 2.5125 (2.7); 2.5088 (3.6); 2.5052 (2.5); 2.5016 (1.1); 2.4179 (28.8); 2.2015 (0.3); 2.1880 (1.0); 2.1745 (1.6); 2.1612 (1.6); 2.1477 (1.0); 2.1342 (0.3); 0.9629 (16.0); 0.9494 (15.5)

I.08: $^1$H-NMR(499.9 MHz, $d_6$-DMSO):
δ = 8.5386 (2.0); 8.5233 (2.0); 4.2147 (2.1); 4.2001 (3.4); 4.1854 (3.2); 4.1777 (1.0); 4.1709 (1.5); 4.1635 (2.7); 4.1567 (0.6); 4.1493 (2.7); 4.1398 (1.0); 4.1351 (1.0); 4.1257 (2.7); 4.1182 (0.6); 4.1115 (2.6); 4.1040 (1.4); 4.0973 (0.9); 4.0898 (1.3); 4.0756 (0.4); 3.3185 (58.2); 2.5358 (0.4); 2.5125 (2.9); 2.5090 (5.5); 2.5054 (7.2); 2.5018 (5.0); 2.4983 (2.3); 2.4080 (27.6); 2.1877 (0.4); 2.1741 (1.1); 2.1605 (1.8); 2.1469 (1.8); 2.1333 (1.1); 2.1197 (0.4); 1.2360 (0.5); 1.2208 (8.0); 1.2065 (16.0); 1.1923 (7.5); 0.9677 (11.8); 0.9540 (12.5); 0.9494 (11.9); 0.9357 (10.5)

I.09: $^1$H-NMR(300.2 MHz, CDCl3):
δ = 7.2988 (3.8); 6.3470 (0.4); 4.2461 (4.5); 4.2294 (4.4); 3.8469 (14.9); 2.5954 (16.0); 1.6069 (3.2); 0.0363 (4.7)

I.10: $^1$H-NMR(499.9 MHz, d6-DMSO):
δ = 12.6968 (0.6); 8.5442 (2.2); 8.5326 (4.3); 8.5209 (2.3); 3.8971 (15.9); 3.8854 (16.0); 3.3973 (0.4); 3.3833 (0.6); 3.3296 (14.9); 2.5810 (0.5); 2.5466 (0.4); 2.5207 (9.4); 2.5166 (4.5); 2.5129 (8.3); 2.5093 (11.3); 2.5056 (8.3); 2.5020 (4.1); 2.4530 (64.6); 2.3213 (0.3)

I.11: $^1$H-NMR(400.1 MHz, $d_6$-DMSO):
δ = 8.5820 (1.4); 8.5628 (1.4); 4.2506 (1.2); 4.2323 (2.1); 4.2141 (1.3); 3.6755 (16.0); 3.3300 (2.1); 2.5111 (1.7); 2.5071 (1.4); 2.4136 (15.3); 2.1826 (0.6); 2.1656 (1.1); 2.1486 (1.2); 2.1316 (0.7); 0.9701 (6.7); 0.9531 (7.3); 0.9458 (7.6); 0.9287 (6.8)

I.12: $^1$H-NMR(300.2 MHz, CDCl3):
δ = 7.2989 (1.9); 6.3630 (0.6); 6.3356 (0.6); 5.5734 (0.5); 5.5680 (0.4); 5.5618 (0.4); 5.5427 (0.5); 5.5375 (0.7); 5.5331 (0.4); 5.5134 (0.4); 5.3759 (0.4); 5.3567 (0.4); 5.3518 (0.7); 5.3465 (0.5); 5.3278 (0.4);

TABLE A-continued

NMR peak lists 5.3216 (0.4); 5.3160 (0.5); 4.7510 (1.2); 4.7362 (1.2); 4.7229 (1.2); 4.7082 (1.2); 4.2548 (0.5); 4.2426 (0.9); 4.2197 (2.5); 4.1976 (2.5); 4.1753 (0.9); 4.1626 (0.5); 2.6800 (0.3); 2.5914 (16.0); 2.4882 (0.6); 2.4650 (1.6); 2.4419 (1.6); 2.4304 (0.4); 2.4199 (0.6); 2.3411 (0.4); 2.3347 (0.5); 2.3197 (0.5); 2.3116 (0.6); 2.2967 (0.6); 2.2887 (0.5); 2.2738 (0.5); 2.1186 (1.0); 2.1163 (1.0); 2.0919 (1.6); 2.0674 (1.1); 2.0652 (1.1); 1.0424 (6.3); 1.0322 (4.4); 1.0195 (6.3); 1.0066 (12.2); 0.9822 (9.5); 0.0339 (2.3)

I.13: $^1$H-NMR(499.9 MHz, CDCl3):
δ = 7.2615 (4.4); 6.2659 (0.6); 6.2495 (0.6); 4.8504 (1.1); 4.8456 (1.1); 4.8194 (1.9); 4.8146 (1.8); 4.7644 (1.3); 4.7552 (1.4); 4.7474 (1.4); 4.7382 (1.4); 4.7332 (2.0); 4.7283 (1.9); 4.7022 (1.1); 4.6973 (1.1); 2.5805 (0.5); 2.5592 (16.0); 2.5139 (1.6); 2.5090 (2.9); 2.5042 (1.4); 2.3363 (0.6); 2.3270 (0.6); 2.3225 (0.8); 2.3133 (0.8); 2.3088 (0.6); 2.2995 (0.5); 1.5613 (3.2); 1.0303 (6.9); 1.0166 (6.6); 0.9933 (6.8); 0.9796 (6.5); 0.0061 (0.4); −0.0002 (5.9)

I.14: $^1$H-NMR(300.2 MHz, CDCl3):
δ = 7.2990 (2.7); 6.3761 (0.5); 6.3487 (0.6); 4.7741 (1.2); 4.7593 (1.2); 4.7461 (1.2); 4.7313 (1.2); 4.0464 (0.3); 4.0242 (0.4); 4.0111 (2.2); 3.9996 (2.3); 3.9889 (2.3); 3.9779 (2.3); 3.9644 (0.4); 3.9426 (0.4); 2.5955 (16.0); 2.3537 (0.4); 2.3388 (0.5); 2.3307 (0.6); 2.3158 (0.5); 2.3078 (0.5); 2.2929 (0.5); 2.0557 (0.4); 2.0334 (0.8); 2.0111 (1.1); 1.9888 (0.9); 1.9665 (0.5); 1.6273 (3.6); 1.0542 (6.5); 1.0313 (6.3); 1.0153 (7.2); 1.0063 (13.8); 0.9923 (7.1); 0.9839 (13.1); 0.0350 (3.2)

I.15: $^1$H-NMR(300.2 MHz, CDCl3):
δ = 7.2991 (6.3); 6.1941 (0.5); 6.1676 (0.5); 4.9561 (1.9); 4.9041 (3.7); 4.8023 (1.6); 4.7985 (4.0); 4.7863 (1.3); 4.7747 (1.2); 4.7583 (1.2); 4.7465 (2.0); 2.5955 (16.0); 2.3810 (0.5); 2.3644 (0.5); 2.3581 (0.6); 2.3417 (0.6); 2.3353 (0.5); 2.3187 (0.5); 1.5948 (3.9); 1.1005 (6.3); 1.0776 (6.1); 1.0599 (6.4); 1.0369 (6.2); 0.0370 (8.1)

I.16: $^1$H-NMR(499.9 MHz, CDCl3):
δ = 7.2637 (2.6); 6.2129 (0.6); 6.1966 (0.7); 5.5218 (0.8); 5.5198 (0.8); 5.5092 (1.4); 5.4987 (0.8); 5.4966 (0.8); 5.4860 (0.3); 4.9335 (0.9); 4.9220 (1.8); 4.9203 (1.8); 4.9087 (1.8); 4.9072 (1.9); 4.8955 (0.9); 4.8944 (0.9); 4.7470 (1.3); 4.7378 (1.4); 4.7302 (1.3); 4.7210 (1.2); 4.7023 (1.0); 4.7010 (1.0); 4.6918 (1.0); 4.6904 (1.1); 4.6868 (1.0); 4.6856 (1.0); 4.6763 (0.8); 4.6751 (0.8); 4.6535 (1.0); 4.6525 (0.9); 4.6430 (1.0); 4.6418 (1.0); 4.6381 (1.0); 4.6368 (0.9); 4.6276 (0.8); 4.6264 (0.8); 2.5771 (0.4); 2.5532 (16.0); 2.3467 (0.5); 2.3373 (0.6); 2.3329 (0.7); 2.3236 (0.7); 2.3192 (0.6); 2.3099 (0.5); 1.1183 (0.4); 1.1051 (0.3); 1.0472 (6.5); 1.0335 (6.3); 1.0025 (6.6); 0.9887 (6.4); −0.0002 (2.6)

I.17: $^1$H-NMR(300.2 MHz, CDCl3):
δ = 7.2987 (1.9); 6.2581 (0.6); 6.2303 (0.6); 5.7442 (0.9); 5.7176 (1.5); 5.6914 (1.0); 4.7086 (1.2); 4.6935 (1.3); 4.6806 (1.2); 4.6654 (1.2); 3.6013 (0.9); 3.5733 (1.3); 3.5692 (1.2); 3.5538 (0.8); 3.5412 (1.1); 3.5216 (1.6); 3.4940 (1.2); 3.3963 (0.4); 3.3906 (0.9); 3.3852 (1.1); 3.3760 (0.9); 3.3706 (0.6); 3.3662 (1.3); 3.3591 (1.7); 3.3512 (1.3); 3.3420 (0.8); 3.3329 (0.8); 3.3298 (0.6); 3.3268 (0.6); 3.3213 (0.4); 2.6073 (0.4); 2.5850 (16.0); 2.3404 (0.5); 2.3250 (0.5); 2.3175 (0.7); 2.3022 (0.6); 2.2946 (0.5); 2.2793 (0.5); 1.0560 (6.4); 1.0331 (6.3); 1.0120 (6.6); 0.9890 (6.3); 0.0323 (2.0)

I.18: $^1$H-NMR(300.2 MHz, CDCl3):
δ = 7.2990 (5.6); 6.1603 (0.7); 6.1337 (0.7); 5.3964 (0.6); 5.3828 (0.8); 5.3705 (1.2); 5.3579 (0.8); 5.3445 (0.7); 5.3379 (0.7); 5.3329 (0.4); 4.7278 (1.2); 4.7115 (1.3); 4.7008 (1.2); 4.6845 (1.2); 4.6621 (1.3); 4.6520 (0.5); 4.6363 (1.3); 4.6257 (0.5); 4.6204 (0.7); 4.6100 (1.8); 4.5946 (0.6); 4.5841 (1.7); 4.3368 (0.6); 4.3244 (1.1); 4.3163 (0.6); 4.3125 (0.6); 4.3056 (0.4); 4.2846 (0.4); 4.2782 (0.4); 4.2720 (0.6); 4.2665 (0.4); 4.2594 (0.4); 4.2350 (0.5); 4.2278 (0.5); 4.2223 (0.9); 4.2096 (0.6); 4.1818 (0.5); 4.1771 (0.4); 4.1695 (0.8); 4.1576 (0.4); 2.6387 (0.3); 2.5896 (16.0); 2.3726 (0.5); 2.3563 (0.5); 2.3502 (0.7); 2.3336 (0.7); 2.3275 (0.6); 2.3107 (0.5); 1.6050 (3.6); 1.0994 (6.4); 1.0765 (6.2); 1.0514 (6.6); 1.0284 (6.4); 0.0360 (5.9)

I.19: $^1$H-NMR(300.2 MHz, CDCl3):
δ = 7.2984 (4.7); 6.3045 (0.7); 6.2825 (0.7); 5.4320 (0.8); 5.4246 (0.8); 5.4169 (1.2); 5.4116 (1.2); 5.4052 (0.8); 5.3966 (0.8); 4.7447 (1.2); 4.7298 (1.3); 4.7168 (1.2); 4.7019 (1.2); 3.9980 (1.1); 3.9833 (1.2); 3.9624 (3.6); 3.9472 (2.9); 3.9364 (1.9); 3.9166 (2.2); 3.9020 (1.0); 3.8785 (1.5); 3.8410 (0.6); 2.6112 (1.0); 2.5932 (16.0); 2.3510 (0.4); 2.3283 (0.7); 2.3227 (0.6); 2.3128 (0.6); 2.3070 (0.8); 2.2912 (0.8); 2.2847 (0.6); 2.2738 (0.8); 2.2633 (0.4); 2.2546 (0.6); 2.2457 (0.7); 2.2363 (0.4); 2.2282 (0.8); 2.2176 (0.4); 2.2082 (0.5); 2.2003 (0.4); 2.1286 (0.5); 2.1059 (0.3); 2.0819 (0.6); 2.0660 (0.6); 2.0421 (0.3); 1.1396 (0.5); 1.1356 (0.5); 1.1176 (0.6); 1.0578 (7.3); 1.0349 (7.1); 1.0149 (7.3); 0.9919 (7.0); 0.0343 (5.8)

I.20: $^1$H-NMR(499.9 MHz, CDCl3):
δ = 7.1612 (2.7); 6.2456 (0.7); 6.2292 (0.7); 4.6155 (1.2); 4.6065 (1.3); 4.5987 (1.2); 4.5897 (1.2); 3.8048 (1.3); 3.7765 (3.7); 3.7478 (3.7); 3.7196 (1.3); 2.4560 (16.0); 2.1647 (0.5); 2.1556 (0.6); 2.1510 (0.7); 2.1419 (0.7); 2.1373 (0.6); 2.1281 (0.5); 1.4819 (1.1); 0.8965 (6.7); 0.8828 (6.5); 0.8665 (6.8); 0.8527 (6.5); 0.0062 (3.1); −0.0002 (47.4); −0.0068 (2.2); −0.1019 (3.3)

I.21: $^1$H-NMR(400.2 MHz, d$_6$-DMSO):
δ = 8.6718 (0.9); 8.6545 (0.9); 8.3154 (0.7); 4.4049 (0.9); 4.3869 (1.4); 4.3689 (1.0); 4.1414 (0.6); 4.1346 (0.7); 4.1236 (2.1); 4.1170 (2.1); 4.1058 (2.2); 4.0993 (2.1); 4.0881 (0.8); 4.0816 (0.6); 3.3277 (9.2); 2.5207 (0.5); 2.5121 (5.4); 2.5077 (10.9); 2.5031 (14.3); 2.4985 (10.4); 2.4940 (5.1); 2.4192 (16.0); 1.3773 (6.7); 1.3590 (6.6); 1.2384 (0.6); 1.2116 (4.7); 1.1939 (9.7); 1.1761 (4.5); −0.0002 (2.1)

I.22: $^1$H-NMR(400.2 MHz, d$_6$-DMSO):
δ = 8.5812 (1.1); 8.5623 (1.1); 8.3154 (1.4); 4.2932 (1.0); 4.2750 (1.8); 4.2569 (1.0); 3.6617 (16.0); 3.3265 (9.6); 3.3025 (0.6); 2.5069 (12.7); 2.5026 (16.6); 2.4982 (12.5); 2.3981 (15.4); 1.9313 (0.5); 1.9270 (0.4); 1.9208 (0.5); 1.9152 (0.6); 1.9098 (0.6); 1.8990 (0.5); 1.8927 (0.4); 1.4939 (0.3); 1.4831 (0.4); 1.4756 (0.4); 1.4602 (0.6); 1.4493 (0.5); 1.4415 (0.5); 1.4307 (0.5); 1.2860 (0.5); 1.2674 (0.7); 1.2461 (0.7); 1.2339 (0.7); 1.2119 (0.4); 0.8990 (6.5); 0.8817 (7.1); 0.8596 (6.7); 0.8409 (2.8); −0.0002 (1.9)

I.23: $^1$H-NMR(400.2 MHz, d$_6$-DMSO):
δ = 9.2313 (3.1); 8.6161 (1.3); 8.5969 (1.3); 8.3148 (0.4); 7.0655 (3.6); 7.0444 (4.0); 6.6837 (0.5); 6.6767 (4.5); 6.6556 (4.1); 6.6487 (0.4); 4.4879 (0.4); 4.4746 (0.5); 4.4688 (0.6); 4.4629 (0.7); 4.4555 (0.6); 4.4497 (0.6); 4.4437 (0.6); 4.4304 (0.4); 4.1286 (0.8); 4.1257 (0.9); 4.1109 (2.6); 4.1081 (2.7); 4.0930 (2.8); 4.0905 (2.6); 4.0750 (1.0); 3.3321 (12.1); 3.0456 (0.6); 3.0325 (0.7); 3.0110 (1.1); 2.9980 (1.0); 2.9317 (1.1); 2.9063 (1.1); 2.8972 (0.7); 2.8717 (0.7); 2.5252 (0.4); 2.5203 (0.6); 2.5117 (8.5); 2.5073

TABLE A-continued

NMR peak lists (17.0); 2.5028 (22.1); 2.4982 (16.0); 2.4937 (7.7); 2.2707 (16.0); 1.2386 (0.5); 1.1761 (5.0); 1.1583 (10.4); 1.1406 (4.8); −0.0002 (3.3)
I.24: $^1$H-NMR(400.2 MHz, $d_6$-DMSO):
δ = 8.6736 (0.8); 8.6549 (0.8); 8.3120 (1.2); 4.4937 (0.6); 4.4788 (0.6); 4.1601 (0.4); 4.1506 (0.6); 4.1423 (1.5); 4.1326 (1.6); 4.1245 (1.6); 4.1149 (1.5); 4.1064 (0.7); 4.0972 (0.4); 3.3267 (13.5); 3.3028 (0.4); 2.5808 (0.7); 2.5639 (0.9); 2.5578 (0.7); 2.5463 (0.7); 2.5378 (1.2); 2.5124 (6.7); 2.5079 (13.4); 2.5033 (17.5); 2.4987 (12.5); 2.4942 (6.1); 2.3832 (13.1); 2.0569 (16.0); 2.0468 (1.3); 2.0318 (0.8); 2.0268 (0.9); 2.0218 (0.5); 2.0130 (0.3); 2.0062 (0.4); 1.2188 (3.6); 1.2010 (7.6); 1.1833 (3.4); −0.0002 (1.6)
I.25: $^1$H-NMR(400.2 MHz, $d_6$-DMSO):
δ = 8.5474 (0.8); 8.5281 (0.8); 8.3108 (0.3); 4.2166 (1.2); 4.1979 (1.6); 4.1898 (0.8); 4.1803 (1.6); 4.1721 (0.7); 4.1627 (1.6); 4.1451 (2.0); 4.1277 (2.0); 4.1101 (1.6); 4.1008 (0.7); 4.0924 (0.5); 4.0831 (0.7); 3.3279 (24.7); 2.5256 (0.4); 2.5209 (0.7); 2.5123 (8.8); 2.5079 (17.6); 2.5033 (23.1); 2.4987 (16.8); 2.4942 (8.2); 2.3701 (16.0); 2.1824 (0.6); 2.1653 (1.0); 2.1483 (1.0); 2.1312 (0.6); 1.2397 (0.5); 1.2244 (4.4); 1.2067 (9.0); 1.1889 (4.3); 0.9701 (6.1); 0.9520 (8.5); 0.9337 (5.7); −0.0002 (1.7)
I.26: $^1$H-NMR(400.2 MHz, $d_6$-DMSO):
δ = 8.6908 (0.9); 8.6716 (1.0); 8.3114 (3.3); 7.3143 (0.4); 7.3005 (0.7); 7.2952 (2.7); 7.2865 (3.3); 7.2799 (10.4); 7.2695 (0.6); 7.2654 (0.8); 7.2379 (0.7); 7.2323 (0.8); 7.2226 (0.8); 7.2164 (0.9); 7.2080 (0.4); 7.2015 (0.4); 4.5934 (0.4); 4.5803 (0.5); 4.5741 (0.5); 4.5679 (0.6); 4.5610 (0.5); 4.5549 (0.5); 4.5486 (0.5); 4.5354 (0.4); 4.1404 (1.0); 4.1228 (3.3); 4.1052 (3.5); 4.0875 (1.2); 3.3323 (29.2); 3.3081 (1.3); 3.1845 (0.7); 3.1713 (0.7); 3.1501 (1.2); 3.1369 (1.0); 3.0625 (1.2); 3.0367 (1.2); 3.0282 (0.8); 3.0024 (0.7); 2.5259 (0.5); 2.5212 (0.8); 2.5126 (9.6); 2.5081 (19.2); 2.5035 (25.0); 2.4989 (18.0); 2.4944 (8.7); 2.2049 (16.0); 1.2393 (0.4); 1.1781 (4.6); 1.1604 (9.8); 1.1426 (4.5); −0.0002 (1.9)
I.27: $^1$H-NMR(400.2 MHz, $d_6$-DMSO):
δ = 8.6725 (0.7); 8.6556 (0.7); 8.3103 (3.2); 4.4126 (0.8); 4.3946 (1.2); 4.3766 (0.8); 4.1439 (0.6); 4.1374 (0.7); 4.1261 (2.0); 4.1198 (2.0); 4.1083 (2.0); 4.1021 (2.0); 4.0906 (0.7); 4.0844 (0.6); 3.3335 (26.6); 3.3092 (1.4); 2.5262 (0.4); 2.5213 (0.6); 2.5128 (8.0); 2.5084 (15.6); 2.5038 (20.0); 2.4993 (14.3); 2.4948 (6.9); 2.3830 (16.0); 1.3841 (6.6); 1.3658 (6.6); 1.2396 (0.3); 1.2146 (4.4); 1.1968 (9.0); 1.1791 (4.3); −0.0002 (1.2)
I.28: $^1$H-NMR(400.1 MHz, CDCl3):
δ = 7.2614 (9.2); 6.3149 (1.0); 4.0958 (5.6); 4.0843 (5.5); 2.5044 (16.0); 1.5556 (11.5); 1.5030 (47.7); −0.0002 (4.5)
I.29: $^1$H-NMR(400.2 MHz, $d_6$-DMSO):
δ = 8.5780 (0.8); 8.5588 (0.8); 8.3113 (0.6); 4.2438 (1.1); 4.2254 (1.7); 4.2071 (1.1); 3.6688 (16.0); 3.3268 (16.9); 2.5256 (0.4); 2.5208 (0.6); 2.5121 (8.0); 2.5077 (15.9); 2.5032 (20.6); 2.4986 (14.8); 2.4941 (7.2); 2.3703 (15.7); 2.1803 (0.5); 2.1632 (0.9); 2.1461 (1.0); 2.1291 (0.6); 1.2396 (0.4); 0.9656 (6.1); 0.9487 (6.1); 0.9403 (6.0); 0.9232 (5.6); −0.0002 (1.7)
I.30: $^1$H-NMR(400.2 MHz, $d_6$-DMSO):
δ = 8.6808 (0.6); 8.6624 (0.7); 8.3101 (2.2); 4.5280 (0.5); 4.5140 (0.5); 3.6707 (12.6); 3.3296 (16.6); 3.3054 (0.9); 2.5788 (0.7); 2.5627 (0.8); 2.5605 (0.8); 2.5507 (0.6); 2.5448 (0.7); 2.5311 (1.2); 2.5264 (0.5); 2.5127 (7.3); 2.5083 (13.5); 2.5037 (17.2); 2.4991 (12.5); 2.4947 (6.0); 2.3847 (13.0); 2.0697 (0.6); 2.0662 (0.5); 2.0549 (16.0); 2.0466 (0.9); 2.0367 (0.8); 2.0303 (0.8); 2.0246 (0.5); 2.0178 (0.3); 2.0094 (0.4); −0.0002 (1.3)
I.31: $^1$H-NMR(400.2 MHz, $d_6$-DMSO):
δ = 8.6854 (0.5); 8.6711 (1.0); 8.6571 (0.5); 3.9968 (4.2); 3.9822 (4.2); 3.6650 (15.9); 3.3779 (94.9); 2.5282 (0.4); 2.5234 (0.5); 2.5148 (6.6); 2.5105 (13.2); 2.5060 (17.3); 2.5016 (12.8); 2.4973 (6.5); 2.4053 (16.0); −0.0002 (0.5)
I.32: $^1$H-NMR(400.2 MHz, $d_6$-DMSO):
δ = 8.5931 (0.9); 8.5741 (0.9); 4.2961 (1.1); 4.2779 (1.9); 4.2596 (1.1); 3.6636 (16.0); 3.3571 (87.2); 2.5264 (0.4); 2.5217 (0.8); 2.5130 (9.0); 2.5087 (17.6); 2.5042 (22.6); 2.4996 (16.2); 2.4951 (7.8); 2.3625 (15.7); 1.9388 (0.4); 1.9341 (0.4); 1.9281 (0.4); 1.9226 (0.4); 1.9168 (0.5); 1.9108 (0.4); 1.9062 (0.4); 1.4875 (0.3); 1.4797 (0.4); 1.4689 (0.4); 1.4644 (0.5); 1.4537 (0.5); 1.4457 (0.4); 1.4350 (0.4); 1.2889 (0.5); 1.2704 (0.7); 1.2542 (0.6); 1.2486 (0.8); 1.2367 (1.1); 1.2147 (0.4); 0.9019 (6.1); 0.8847 (6.3); 0.8805 (3.8); 0.8617 (6.3); 0.8431 (2.6)
I.33: $^1$H-NMR(400.2 MHz, $d_6$-DMSO):
δ = 8.6403 (1.0); 8.6209 (1.0); 4.4022 (0.4); 4.3909 (0.6); 4.3830 (0.5); 4.3768 (0.6); 4.3718 (0.7); 4.3647 (0.6); 4.3578 (0.5); 4.3454 (0.5); 4.1580 (0.4); 4.1488 (0.6); 4.1400 (0.5); 4.1370 (0.7); 4.1310 (1.8); 4.1193 (1.9); 4.1132 (1.9); 4.1016 (1.8); 4.0954 (0.7); 4.0927 (0.5); 4.0839 (0.6); 4.0746 (0.4); 3.3276 (22.3); 2.5256 (0.5); 2.5120 (9.8); 2.5079 (18.5); 2.5034 (23.5); 2.4989 (16.9); 2.4945 (8.1); 2.3741 (16.0); 1.7675 (0.3); 1.7556 (0.5); 1.7409 (0.4); 1.7350 (0.5); 1.7289 (0.6); 1.7237 (0.7); 1.6986 (0.8); 1.6871 (0.5); 1.6708 (0.5); 1.6666 (0.5); 1.6540 (0.5); 1.5904 (0.7); 1.5780 (0.5); 1.5687 (0.5); 1.5575 (0.9); 1.5464 (0.5); 1.5365 (0.4); 1.2396 (0.5); 1.2126 (4.5); 1.1949 (9.2); 1.1771 (4.3); 0.9290 (5.8); 0.9130 (5.5); 0.8934 (5.6); 0.8774 (5.5); −0.0002 (1.6)
I.34: $^1$H-NMR(400.2 MHz, $d_6$-DMSO):
δ = 8.6967 (0.7); 8.3111 (5.2); 7.3868 (4.2); 7.3838 (2.7); 7.3755 (11.1); 7.3660 (1.0); 7.3570 (1.2); 7.3488 (1.0); 7.3437 (0.6); 7.3355 (0.8); 5.1644 (8.1); 4.0530 (1.8); 4.0439 (1.9); 3.3322 (22.9); 3.3081 (1.6); 2.5258 (0.4); 2.5210 (0.7); 2.5125 (7.8); 2.5080 (15.4); 2.5034 (19.9); 2.4987 (14.3); 2.4942 (6.8); 2.3883 (16.0); −0.0002 (1.6)
I.35: $^1$H-NMR(400.2 MHz, $d_6$-DMSO):
δ = 8.6811 (0.8); 8.6624 (0.8); 8.3098 (1.3); 4.5482 (0.3); 4.5332 (0.4); 4.5281 (0.6); 4.5136 (0.6); 4.5087 (0.5); 4.4937 (0.3); 3.6706 (12.7); 3.3308 (24.4); 3.3071 (0.6); 2.5787 (0.7); 2.5626 (0.8); 2.5606 (0.8); 2.5507 (0.7); 2.5448 (0.8); 2.5311 (1.3); 2.5266 (0.6); 2.5127 (7.6); 2.5083 (14.0); 2.5038 (18.0); 2.4992 (13.3); 2.4949 (6.5); 2.3847 (13.1); 2.0694 (0.6); 2.0663 (0.6); 2.0549 (16.0); 2.0366 (0.9); 2.0302 (0.9); 2.0245 (0.5); 2.0179 (0.4); 2.0093 (0.4); −0.0002 (1.1)
I.36: $^1$H-NMR(400.2 MHz, $d_6$-DMSO):
δ = 8.6905 (0.7); 8.6725 (0.7); 4.5269 (0.5); 4.5119 (0.5); 3.6693 (12.7); 3.3460 (49.0); 2.5791 (0.7); 2.5629 (0.8); 2.5608 (0.8); 2.5511 (0.6); 2.5448 (0.7); 2.5315 (1.2); 2.5260 (0.5); 2.5124 (7.7); 2.5080

TABLE A-continued

NMR peak lists (14.1); 2.5034 (18.2); 2.4988 (13.4); 2.4944 (6.4); 2.3833 (13.0); 2.0680 (0.6); 2.0646 (0.6); 2.0542 (16.0); 2.0448 (0.9); 2.0351 (0.8); 2.0285 (0.8); 2.0229 (0.5); 2.0163 (0.4); 2.0078 (0.4); 1.2386 (0.4); −0.0002 (0.4)
I.37: $^1$H-NMR(400.2 MHz, d$_6$-DMSO):
δ = 8.6536 (0.9); 8.6345 (1.0); 4.4017 (0.4); 4.3903 (0.5); 4.3824 (0.4); 4.3761 (0.5); 4.3711 (0.6); 4.3639 (0.5); 4.3570 (0.4); 4.3448 (0.5); 4.1578 (0.4); 4.1486 (0.5); 4.1399 (0.5); 4.1369 (0.7); 4.1308 (1.8); 4.1192 (1.9); 4.1130 (1.9); 4.1015 (1.8); 4.0952 (0.7); 4.0924 (0.5); 4.0838 (0.6); 4.0745 (0.4); 3.3596 (80.0); 2.5271 (0.4); 2.5223 (0.6); 2.5137 (8.1); 2.5092 (16.2); 2.5046 (21.0); 2.5000 (15.2); 2.4955 (7.4); 2.3732 (16.0); 1.7672 (0.3); 1.7554 (0.4); 1.7408 (0.4); 1.7349 (0.4); 1.7288 (0.6); 1.7234 (0.7); 1.6978 (0.8); 1.6850 (0.4); 1.6808 (0.4); 1.6686 (0.4); 1.6641 (0.4); 1.6518 (0.4); 1.6480 (0.4); 1.5908 (0.7); 1.5784 (0.5); 1.5689 (0.4); 1.5580 (0.8); 1.5468 (0.5); 1.5389 (0.5); 1.2391 (0.5); 1.2101 (4.5); 1.1923 (9.3); 1.1746 (4.3); 0.9281 (5.5); 0.9121 (5.2); 0.8920 (5.2); 0.8760 (5.2)
I.38: $^1$H-NMR(400.2 MHz, d$_6$-DMSO):
δ = 8.6900 (1.0); 8.6708 (1.0); 8.3115 (1.5); 7.3142 (0.4); 7.2950 (2.7); 7.2864 (3.3); 7.2799 (10.4); 7.2693 (0.6); 7.2654 (0.8); 7.2378 (0.7); 7.2321 (0.8); 7.2226 (0.8); 7.2162 (0.9); 7.2080 (0.4); 7.2014 (0.4); 4.5933 (0.4); 4.5803 (0.5); 4.5740 (0.5); 4.5678 (0.7); 4.5608 (0.6); 4.5547 (0.6); 4.5484 (0.6); 4.5352 (0.4); 4.1405 (1.0); 4.1229 (3.3); 4.1053 (3.5); 4.0875 (1.2); 3.3295 (22.9); 3.3055 (0.6); 3.1844 (0.7); 3.1712 (0.7); 3.1499 (1.2); 3.1369 (1.0); 3.0624 (1.2); 3.0367 (1.2); 3.0281 (0.8); 3.0024 (0.7); 2.5257 (0.5); 2.5209 (0.8); 2.5123 (10.1); 2.5079 (19.9); 2.5034 (25.7); 2.4988 (18.5); 2.4943 (8.9); 2.2050 (16.0); 1.2397 (0.4); 1.1782 (4.6); 1.1605 (9.6); 1.1427 (4.4); −0.0002 (1.9)
I.39: $^1$H-NMR(400.2 MHz, d$_6$-DMSO):
δ = 9.2514 (2.6); 8.6265 (1.2); 8.6072 (1.3); 7.0685 (3.3); 7.0473 (3.6); 6.6844 (0.5); 6.6774 (4.2); 6.6727 (1.3); 6.6610 (1.2); 6.6562 (3.9); 6.6491 (0.4); 4.4934 (0.5); 4.4802 (0.5); 4.4742 (0.5); 4.4684 (0.6); 4.4610 (0.6); 4.4551 (0.5); 4.4491 (0.6); 4.4358 (0.4); 4.1303 (0.7); 4.1273 (0.8); 4.1125 (2.3); 4.1096 (2.4); 4.0947 (2.5); 4.0920 (2.3); 4.0767 (0.9); 3.3686 (95.7); 3.3653 (83.9); 3.3630 (90.8); 3.0518 (0.6); 3.0386 (0.6); 3.0172 (1.0); 3.0041 (0.9); 2.9377 (1.0); 2.9124 (1.0); 2.9032 (0.7); 2.8779 (0.6); 2.5268 (0.7); 2.5219 (1.1); 2.5135 (14.1); 2.5090 (28.2); 2.5044 (36.7); 2.4998 (26.4); 2.4953 (12.7); 2.2313 (16.0); 1.2389 (0.6); 1.1761 (4.7); 1.1584 (10.0); 1.1406 (4.5); −0.0002 (2.0)
I.40: $^1$H-NMR(400.2 MHz, d$_6$-DMSO):
δ = 8.5609 (0.8); 8.5416 (0.8); 4.2142 (1.2); 4.1967 (1.6); 4.1954 (1.6); 4.1894 (0.8); 4.1779 (1.3); 4.1716 (0.7); 4.1623 (1.6); 4.1446 (2.0); 4.1272 (2.1); 4.1095 (1.6); 4.1002 (0.7); 4.0918 (0.5); 4.0824 (0.7); 3.3649 (92.0); 2.5272 (0.4); 2.5222 (0.7); 2.5138 (8.6); 2.5093 (17.2); 2.5047 (22.3); 2.5001 (16.0); 2.4956 (7.6); 2.3690 (16.0); 2.1804 (0.5); 2.1634 (0.9); 2.1463 (0.9); 2.1293 (0.6); 1.2387 (0.6); 1.2217 (4.5); 1.2040 (9.3); 1.1862 (4.4); 0.9695 (5.9); 0.9522 (7.3); 0.9500 (7.0); 0.9326 (5.5)
I.41: $^1$H-NMR(400.2 MHz, d$_6$-DMSO):
δ = 8.6430 (0.4); 8.6288 (0.8); 8.6146 (0.4); 8.3108 (1.2); 4.9724 (0.4); 4.9567 (1.1); 4.9411 (1.5); 4.9255 (1.1); 4.9099 (0.4); 3.9385 (3.3); 3.9240 (3.3); 3.3286 (18.1); 3.3045 (0.5); 2.5261 (0.4); 2.5212 (0.6); 2.5126 (7.2); 2.5082 (14.4); 2.5037 (18.6); 2.4991 (13.4); 2.4947 (6.5); 2.4037 (16.0); 1.2153 (15.9); 1.1996 (15.7); −0.0002 (1.4)
I.42: $^1$H-NMR(400.2 MHz, d$_6$-DMSO):
δ = 8.6724 (0.8); 8.6551 (0.8); 8.3108 (0.7); 4.4126 (1.0); 4.3946 (1.6); 4.3766 (1.0); 4.1439 (0.6); 4.1374 (0.7); 4.1261 (2.0); 4.1198 (2.0); 4.1083 (2.0); 4.1021 (2.0); 4.0905 (0.7); 4.0844 (0.6); 3.3317 (29.5); 3.3081 (0.3); 2.5260 (0.4); 2.5127 (7.7); 2.5083 (15.0); 2.5037 (19.4); 2.4991 (14.0); 2.4947 (6.8); 2.3830 (16.0); 1.3839 (6.5); 1.3657 (6.4); 1.2144 (7.3); 1.1967 (8.9); 1.1789 (4.2); −0.0002 (1.3)
I.43: $^1$H-NMR(400.2 MHz, d$_6$-DMSO):
δ = 8.9195 (2.0); 4.0933 (1.3); 4.0756 (4.2); 4.0579 (4.2); 4.0401 (1.3); 3.3493 (68.1); 2.5263 (0.4); 2.5215 (0.6); 2.5128 (7.5); 2.5084 (15.0); 2.5038 (19.5); 2.4992 (14.1); 2.4947 (6.8); 2.3689 (16.0); 1.4425 (1.1); 1.4304 (2.9); 1.4221 (3.1); 1.4112 (1.3); 1.2388 (0.3); 1.1749 (1.5); 1.1689 (4.9); 1.1641 (3.3); 1.1556 (3.4); 1.1513 (9.6); 1.1436 (1.3); 1.1335 (4.3); −0.0002 (1.1)
I.44: $^1$H-NMR(400.2 MHz, d$_6$-DMSO):
δ = 8.5590 (0.9); 8.5399 (0.9); 4.2145 (1.2); 4.1967 (1.8); 4.1894 (0.8); 4.1783 (1.4); 4.1715 (0.7); 4.1622 (1.6); 4.1446 (2.0); 4.1271 (2.0); 4.1095 (1.6); 4.1002 (0.7); 4.0918 (0.5); 4.0824 (0.7); 3.3452 (65.9); 2.5258 (0.5); 2.5124 (9.5); 2.5080 (18.5); 2.5034 (23.6); 2.4988 (16.9); 2.4944 (8.1); 2.3691 (16.0); 2.1803 (0.6); 2.1633 (1.0); 2.1462 (1.0); 2.1292 (0.6); 1.2390 (0.5); 1.2216 (4.5); 1.2038 (9.1); 1.1861 (4.3); 0.9695 (6.3); 0.9521 (8.1); 0.9326 (5.8); −0.0002 (1.2)
I.45: $^1$H-NMR(400.2 MHz, d$_6$-DMSO):
δ = 8.7008 (1.4); 8.6815 (1.4); 7.3164 (0.6); 7.2970 (3.2); 7.2872 (4.4); 7.2816 (11.0); 7.2667 (1.0); 7.2400 (0.8); 7.2346 (1.0); 7.2253 (1.0); 7.2186 (1.1); 7.2102 (0.6); 7.2034 (0.5); 4.5939 (0.5); 4.5806 (0.7); 4.5746 (0.7); 4.5684 (0.8); 4.5614 (0.7); 4.5551 (0.7); 4.5490 (0.7); 4.5358 (0.5); 4.1390 (1.2); 4.1214 (3.7); 4.1037 (3.8); 4.0860 (1.3); 3.3510 (98.3); 3.1844 (0.8); 3.1713 (0.8); 3.1501 (1.3); 3.1371 (1.2); 3.0614 (1.3); 3.0356 (1.3); 3.0271 (0.9); 3.0013 (0.8); 2.5081 (23.1); 2.5037 (28.5); 2.4993 (20.7); 2.2039 (16.0); 1.2383 (0.7); 1.1746 (4.7); 1.1568 (9.5); 1.1391 (4.5); −0.0002 (0.7)
I.46: $^1$H-NMR(400.2 MHz, d$_6$-DMSO):
δ = 8.5881 (0.8); 8.5689 (0.8); 4.2420 (1.1); 4.2241 (1.6); 4.2053 (1.1); 3.6681 (16.0); 3.3468 (61.3); 2.5260 (0.4); 2.5213 (0.5); 2.5126 (7.2); 2.5081 (14.4); 2.5035 (18.7); 2.4989 (13.4); 2.4944 (6.4); 2.3693 (15.6); 2.1785 (0.5); 2.1613 (0.9); 2.1443 (0.9); 2.1272 (0.6); 1.2390 (0.4); 0.9649 (5.8); 0.9479 (5.8); 0.9390 (5.6); 0.9220 (5.3); −0.0002 (0.9)
I.47: $^1$H-NMR(400.2 MHz, d$_6$-DMSO):
δ = 8.6834 (0.8); 8.6646 (0.8); 4.5130 (0.3); 4.4978 (0.4); 4.4931 (0.6); 4.4781 (0.6); 4.4738 (0.5); 4.4584 (0.3); 4.1593 (0.4); 4.1497 (0.6); 4.1415 (1.5); 4.1317 (1.6); 4.1237 (1.6); 4.1140 (1.5); 4.1056 (0.6); 4.0963 (0.4); 3.3489 (62.0); 2.5813 (0.6); 2.5646 (0.8); 2.5580 (0.6); 2.5468 (0.6); 2.5381 (1.2); 2.5258 (0.5); 2.5128 (7.1); 2.5083 (14.3); 2.5037 (18.8); 2.4990 (13.4); 2.4945 (6.4); 2.3820 (13.0); 2.0563 (16.0); 2.0458 (1.2); 2.0420 (0.8); 2.0308 (0.8); 2.0257 (0.9); 2.0205 (0.5); 2.0118 (0.3); 2.0050 (0.4); 1.2388 (0.4); 1.2161 (3.6); 1.1984 (7.6); 1.1807 (3.4); −0.0002 (0.9)
I.48: $^1$H-NMR(499.9 MHz, d$_6$-DMSO):
δ = 8.6674 (1.4); 8.6559 (2.3); 8.6444 (1.1); 4.0600 (5.2); 4.0468 (10.0); 4.0337 (5.0); 3.9915 (8.4); 3.9798 (8.1); 3.7102 (7.3); 3.3215 (9.0); 3.1463 (13.6); 2.5364 (0.4); 2.5114 (2.7); 2.5079 (3.3); 2.5044 (2.4); 2.4418 (7.3); 2.4083 (30.6); 1.6384 (0.9); 1.6239 (2.7); 1.6103 (5.0); 1.5957 (5.0); 1.5821 (2.5); 1.5677

TABLE A-continued

NMR peak lists (0.6); 0.9091 (8.4); 0.8943 (16.0); 0.8794 (7.2)
I.49: ¹H-NMR(300.2 MHz, CDCl3):
δ = 7.4923 (0.3); 7.2989 (3.9); 6.3916 (0.5); 6.3644 (0.6); 5.1699 (0.4); 5.1490 (1.0); 5.1282 (1.4); 5.1073 (1.0); 5.0864 (0.4); 4.7153 (1.2); 4.7009 (1.3); 4.6875 (1.2); 4.6730 (1.2); 2.6476 (1.2); 2.5976 (16.0); 2.4411 (0.9); 2.3587 (1.0); 2.3402 (0.5); 2.3256 (0.5); 2.3172 (0.7); 2.3026 (0.7); 2.2943 (0.5); 2.2797 (0.5); 1.6249 (0.8); 1.3363 (7.6); 1.3316 (8.1); 1.3153 (7.7); 1.3108 (8.1); 1.0442 (6.6); 1.0213 (6.5); 1.0071 (6.8); 0.9841 (6.5); 0.0359 (4.1)
I.50: ¹H-NMR(300.2 MHz, d₆-DMSO):
δ = 8.9269 (2.0); 3.6346 (16.0); 3.3469 (6.1); 2.5345 (0.6); 2.5286 (1.2); 2.5225 (1.7); 2.5165 (1.2); 2.5106 (0.6); 2.3931 (15.8); 1.4833 (1.0); 1.4668 (2.6); 1.4557 (3.0); 1.4414 (1.3); 1.2147 (1.4); 1.2003 (2.9); 1.1892 (2.7); 1.1726 (1.0); 0.0193 (1.2)
I.51: ¹H-NMR(400.2 MHz, d₆-DMSO):
δ = 8.7996 (2.3); 2.8919 (0.8); 2.7333 (0.7); 2.7322 (0.7); 2.5210 (0.4); 2.5125 (4.1); 2.5081 (8.4); 2.5035 (11.0); 2.4989 (7.9); 2.4944 (3.8); 2.3887 (1.7); 2.3706 (16.0); 1.4114 (1.1); 1.3996 (2.7); 1.3914 (2.9); 1.3807 (1.3); 1.3753 (0.8); 1.3568 (0.6); 1.1254 (1.3); 1.1147 (2.8); 1.1065 (2.8); 1.0946 (1.0); −0.0002 (7.8)
I.52: ¹H-NMR(400.1 MHz, CDCl3):
δ = 7.2604 (9.4); 6.3394 (1.0); 6.3189 (1.0); 4.7313 (1.4); 4.7205 (1.4); 4.7103 (1.4); 4.6995 (1.3); 4.0842 (1.0); 4.0656 (1.2); 4.0560 (1.9); 4.0374 (1.8); 3.9951 (1.8); 3.9769 (1.8); 3.9669 (1.0); 3.9485 (0.9); 2.5620 (16.0); 2.5133 (0.8); 2.3211 (0.6); 2.3042 (0.9); 2.2925 (0.9); 2.2754 (0.7); 1.5420 (6.0); 1.1955 (0.4); 1.1832 (0.7); 1.1754 (0.7); 1.1640 (1.1); 1.1521 (0.8); 1.1448 (1.1); 1.1272 (0.6); 1.0202 (7.9); 1.0029 (8.0); 0.9934 (8.3); 0.9760 (7.7); 0.9527 (0.5); 0.6225 (0.8); 0.6097 (3.0); 0.5900 (2.9); 0.5778 (0.8); 0.3245 (1.1); 0.3128 (3.3); 0.3008 (3.1); 0.2885 (0.8); −0.0002 (9.8)
I.53: ¹H-NMR(400.1 MHz, CDCl3):
δ = 7.2594 (9.0); 6.3038 (0.9); 6.2837 (0.9); 5.0683 (1.1); 5.0498 (1.6); 5.0313 (1.1); 4.6842 (1.3); 4.6733 (1.4); 4.6633 (1.3); 4.6524 (1.3); 2.5560 (16.0); 2.3975 (1.2); 2.3796 (1.4); 2.3660 (1.3); 2.3489 (0.7); 2.3056 (0.7); 2.2938 (0.7); 2.2887 (0.9); 2.2770 (0.9); 2.2718 (0.8); 2.2601 (0.6); 2.1539 (0.7); 2.1338 (0.9); 2.1293 (0.9); 2.1108 (1.0); 2.0925 (0.9); 2.0861 (0.9); 2.0614 (0.6); 1.8789 (0.4); 1.8527 (0.9); 1.8269 (0.9); 1.8018 (0.3); 1.6862 (0.6); 1.6655 (1.0); 1.6396 (0.9); 1.6187 (0.4); 1.5406 (7.5); 1.0083 (7.6); 0.9912 (7.7); 0.9728 (7.8); 0.9555 (7.3); −0.0002 (9.5)
I.54: ¹H-NMR(400.1 MHz, CDCl3):
δ = 7.3486 (0.6); 7.2595 (9.4); 6.3215 (1.0); 6.3020 (1.0); 4.7145 (1.4); 4.7036 (1.4); 4.6942 (1.4); 4.6833 (1.3); 4.2074 (0.3); 4.1913 (0.9); 4.1739 (0.9); 4.1635 (1.2); 4.1475 (3.3); 4.1308 (3.3); 4.1149 (1.2); 4.1047 (0.6); 3.4468 (0.3); 3.4310 (0.4); 2.5587 (16.0); 2.5143 (1.7); 2.3009 (0.7); 2.2843 (1.0); 2.2724 (1.0); 2.2552 (0.7); 1.7407 (0.6); 1.7247 (1.7); 1.7073 (3.2); 1.6898 (3.2); 1.6721 (1.7); 1.6535 (0.4); 1.5408 (6.9); 1.1159 (0.9); 1.0986 (0.9); 1.0107 (8.1); 0.9933 (8.5); 0.9875 (6.5); 0.9749 (9.2); 0.9687 (10.0); 0.9583 (8.6); 0.9492 (5.6); 0.9293 (1.8); 0.9107 (0.5); −0.0002 (9.7); −0.0016 (9.7)
I.55: ¹H-NMR(400.1 MHz, CDCl3):
δ = 7.2596 (8.2); 6.3204 (0.9); 6.3002 (0.9); 4.7089 (1.4); 4.6979 (1.4); 4.6880 (1.3); 4.6769 (1.3); 4.2144 (0.6); 4.2044 (1.2); 4.1879 (3.2); 4.1715 (3.2); 4.1554 (1.1); 4.1449 (0.5); 2.5843 (0.7); 2.5583 (16.0); 2.2961 (0.6); 2.2792 (0.9); 2.2675 (0.9); 2.2504 (0.6); 1.6899 (0.5); 1.6739 (1.6); 1.6532 (2.2); 1.6359 (2.0); 1.6192 (0.8); 1.5483 (2.3); 1.4477 (0.4); 1.4294 (1.4); 1.4108 (2.4); 1.3918 (2.3); 1.3732 (1.3); 1.3551 (0.3); 1.2491 (0.5); 1.2322 (0.5); 1.0085 (7.7); 0.9913 (7.6); 0.9712 (8.4); 0.9662 (6.2); 0.9540 (8.3); 0.9471 (8.9); 0.9285 (3.7); −0.0002 (8.6)
I.56: ¹H-NMR(400.1 MHz, CDCl3):
δ = 7.2595 (8.6); 6.2836 (1.1); 6.2640 (1.1); 4.6642 (1.4); 4.6531 (1.5); 4.6435 (1.4); 4.6322 (1.4); 4.2198 (1.1); 4.2102 (1.4); 4.1985 (1.0); 4.1893 (0.4); 2.5737 (0.6); 2.5578 (16.0); 2.2586 (0.7); 2.2413 (1.0); 2.2270 (1.0); 2.2122 (0.7); 1.5416 (4.5); 1.0866 (0.4); 1.0705 (0.3); 0.9966 (7.9); 0.9795 (7.7); 0.9540 (7.9); 0.9368 (7.6); 0.7910 (0.9); 0.7732 (3.7); 0.7574 (6.2); 0.7336 (1.8); −0.0002 (9.0)
I.57: ¹H-NMR(400.1 MHz, CDCl3):
δ = 7.3962 (0.5); 7.3643 (13.9); 7.3411 (0.8); 7.3280 (0.3); 7.2583 (9.0); 6.2948 (1.0); 6.2743 (1.0); 5.2567 (1.6); 5.2264 (3.5); 5.1808 (3.5); 5.1505 (1.5); 4.7627 (1.3); 4.7516 (1.4); 4.7417 (1.3); 4.7305 (1.3); 2.5374 (16.0); 2.3031 (0.6); 2.2859 (0.9); 2.2743 (0.9); 2.2689 (0.8); 2.2575 (0.6); 1.5387 (6.1); 0.9786 (7.4); 0.9614 (7.2); 0.9198 (7.5); 0.9026 (7.2); −0.0002 (9.5)
I.58: ¹H-NMR(400.1 MHz, CDCl3):
δ = 7.2593 (8.8); 6.2970 (1.0); 6.2770 (1.0); 5.9603 (0.6); 5.9466 (0.6); 5.9330 (0.9); 5.9176 (1.0); 5.9037 (0.6); 5.8914 (0.7); 5.8768 (0.4); 5.3842 (2.0); 5.3414 (1.7); 5.2997 (2.1); 5.2737 (1.9); 4.7448 (1.4); 4.7338 (1.5); 4.7238 (1.8); 4.7126 (1.6); 4.6907 (1.9); 4.6732 (3.1); 4.6573 (1.7); 4.6395 (0.4); 4.6249 (0.4); 2.5760 (0.7); 2.5570 (16.0); 2.3172 (0.7); 2.3005 (1.0); 2.2862 (1.0); 2.2711 (0.7); 1.5410 (5.1); 1.1011 (0.4); 1.0846 (0.5); 1.0155 (7.8); 0.9985 (7.7); 0.9767 (7.9); 0.9594 (7.6); −0.0002 (9.0)
I.59: ¹H-NMR(300.2 MHz, CDCl3):
δ = 7.2986 (11.6); 6.2315 (0.4); 6.2038 (0.5); 4.8488 (1.2); 4.8334 (1.2); 4.8206 (1.2); 4.8053 (1.3); 4.7793 (0.8); 4.7649 (0.4); 4.7516 (0.8); 4.7372 (1.0); 4.7095 (1.0); 4.6818 (0.4); 4.5314 (0.3); 4.5037 (1.0); 4.4760 (1.1); 4.4616 (0.8); 4.4483 (0.4); 4.4339 (0.8); 2.9948 (0.7); 2.9227 (0.6); 2.9210 (0.6); 2.5940 (16.0); 2.3853 (0.4); 2.3698 (0.4); 2.3624 (0.6); 2.3469 (0.6); 2.3396 (0.5); 2.3239 (0.4); 1.5881 (7.6); 1.0855 (6.1); 1.0627 (5.9); 1.0411 (6.2); 1.0181 (6.0); 0.0484 (0.4); 0.0376 (12.4); 0.0284 (0.4); 0.0267 (0.5)
I.60: ¹H-NMR(300.2 MHz, CDCl3):
δ = 7.4710 (1.0); 7.4693 (1.1); 7.4629 (0.5); 7.4448 (2.5); 7.4231 (0.9); 7.4177 (2.0); 7.3292 (1.1); 7.3254 (0.6); 7.3102 (0.6); 7.3046 (1.6); 7.2981 (4.8); 7.2833 (0.4); 7.2798 (0.5); 7.1597 (2.2); 7.1558 (2.9); 7.1487 (0.7); 7.1309 (2.2); 7.1277 (1.8); 6.3872 (0.6); 6.3590 (0.6); 5.0168 (1.2); 5.0017 (1.3); 4.9888 (1.2); 4.9736 (1.2); 2.6094 (16.0); 2.5512 (0.4); 2.5359 (0.5); 2.5282 (0.6); 2.5130 (0.6); 2.5054 (0.5); 2.4901 (0.5); 2.0430 (0.4); 1.5985 (1.6); 1.1772 (6.2); 1.1538 (10.8); 1.1296 (6.0); 0.0381 (5.3)
I.61: ¹H-NMR(300.2 MHz, CDCl3):
δ = 7.2987 (0.6); 4.6463 (0.5); 4.6324 (0.5); 4.6188 (0.5); 4.6049 (0.5); 2.5964 (6.0); 1.5260 (16.0); 1.0332 (2.4); 1.0101 (2.5); 1.0044 (2.7); 0.9813 (2.3); 0.0320 (0.7)
I.62: ¹H-NMR(400.2 MHz, d₆-DMSO):
δ = 8.5464 (1.0); 8.5272 (1.0); 4.2137 (1.1); 4.2053 (0.3); 4.1950 (1.6); 4.1876 (0.8); 4.1777 (1.6); 4.1698

TABLE A-continued

NMR peak lists (0.8); 4.1605 (1.7); 4.1428 (2.2); 4.1253 (2.2); 4.1076 (1.7); 4.0983 (0.8); 4.0899 (0.5); 4.0806 (0.7); 3.3247 (9.9); 2.5119 (4.5); 2.5074 (9.4); 2.5028 (12.4); 2.4982 (8.8); 2.4937 (4.2); 2.4047 (16.0); 2.1760 (0.5); 2.1590 (1.0); 2.1420 (1.0); 2.1250 (0.6); 1.2215 (4.8); 1.2038 (9.9); 1.1860 (4.6); 0.9661 (6.2); 0.9485 (9.7); 0.9305 (5.7); −0.0002 (7.1)

I.63: $^1$H-NMR(400.2 MHz, $d_6$-DMSO):
δ = 8.5741 (0.9); 8.5548 (0.9); 4.2417 (1.0); 4.2235 (1.6); 4.2051 (1.1); 3.6668 (16.0); 3.3250 (9.2); 2.5120 (3.8); 2.5075 (7.9); 2.5030 (10.4); 2.4983 (7.4); 2.4938 (3.5); 2.4052 (15.2); 2.1743 (0.5); 2.1572 (0.9); 2.1401 (0.9); 2.1231 (0.6); 0.9616 (5.9); 0.9446 (6.1); 0.9372 (5.8); 0.9202 (5.4); −0.0002 (6.8)

I.64: $^1$H-NMR(400.2 MHz, $d_6$-DMSO):
δ = 8.5740 (0.9); 8.5547 (0.9); 4.2421 (1.1); 4.2240 (1.6); 4.2055 (1.1); 3.6671 (16.0); 3.3246 (6.8); 2.5121 (3.6); 2.5076 (7.4); 2.5030 (9.7); 2.4984 (6.9); 2.4939 (3.2); 2.4054 (15.3); 2.1745 (0.5); 2.1574 (0.9); 2.1404 (1.0); 2.1233 (0.6); 1.2382 (0.4); 0.9617 (6.1); 0.9448 (6.2); 0.9374 (6.0); 0.9203 (5.5); −0.0002 (7.1)

I.65: $^1$H-NMR(400.2 MHz, $d_6$-DMSO):
δ = 8.6889 (1.4); 8.6696 (1.4); 7.3148 (0.6); 7.2956 (3.1); 7.2857 (4.2); 7.2801 (10.8); 7.2688 (0.9); 7.2650 (1.1); 7.2381 (0.8); 7.2328 (1.0); 7.2236 (1.0); 7.2167 (1.1); 7.2083 (0.6); 7.2016 (0.5); 4.5907 (0.5); 4.5775 (0.6); 4.5713 (0.6); 4.5652 (0.8); 4.5583 (0.7); 4.5520 (0.7); 4.5458 (0.7); 4.5326 (0.5); 4.1380 (1.2); 4.1205 (3.8); 4.1028 (3.9); 4.0850 (1.3); 3.3278 (8.7); 3.1798 (0.7); 3.1668 (0.8); 3.1455 (1.3); 3.1324 (1.2); 3.0573 (1.3); 3.0315 (1.3); 3.0230 (0.9); 2.9972 (0.8); 2.5117 (5.2); 2.5075 (10.1); 2.5030 (12.9); 2.4985 (9.3); 2.4943 (4.5); 2.2451 (16.0); 1.2380 (0.3); 1.1750 (4.9); 1.1573 (10.1); 1.1395 (4.7); −0.0002 (7.1)

I.66: $^1$H-NMR(400.2 MHz, $d_6$-DMSO):
δ = 8.6890 (1.4); 8.6696 (1.4); 7.3172 (0.4); 7.3148 (0.6); 7.3010 (0.9); 7.2959 (3.0); 7.2858 (3.9); 7.2800 (10.6); 7.2688 (0.8); 7.2648 (1.0); 7.2382 (0.8); 7.2329 (0.9); 7.2238 (0.9); 7.2167 (1.0); 7.2083 (0.6); 7.2015 (0.5); 4.5903 (0.5); 4.5771 (0.6); 4.5709 (0.6); 4.5648 (0.7); 4.5579 (0.6); 4.5516 (0.6); 4.5454 (0.6); 4.5322 (0.5); 4.1379 (1.1); 4.1204 (3.7); 4.1027 (3.9); 4.0849 (1.3); 3.3277 (9.7); 3.1797 (0.7); 3.1665 (0.8); 3.1453 (1.2); 3.1322 (1.1); 3.0570 (1.2); 3.0312 (1.2); 3.0227 (0.8); 2.9969 (0.7); 2.5205 (0.4); 2.5120 (5.3); 2.5076 (10.5); 2.5030 (13.7); 2.4984 (9.7); 2.4939 (4.6); 2.2451 (16.0); 1.2379 (0.3); 1.1750 (5.1); 1.1573 (10.6); 1.1395 (4.9); −0.0002 (8.7)

I.67: $^1$H-NMR(400.2 MHz, $d_6$-DMSO):
δ = 8.6895 (1.3); 8.6701 (1.3); 7.3174 (0.4); 7.3148 (0.6); 7.3012 (0.8); 7.2961 (2.8); 7.2945 (2.6); 7.2859 (3.6); 7.2801 (9.9); 7.2689 (0.7); 7.2647 (1.0); 7.2383 (0.8); 7.2331 (0.9); 7.2240 (0.8); 7.2168 (1.0); 7.2083 (0.6); 7.2016 (0.5); 4.5901 (0.4); 4.5769 (0.6); 4.5707 (0.6); 4.5645 (0.7); 4.5576 (0.6); 4.5513 (0.6); 4.5451 (0.6); 4.5319 (0.5); 4.1375 (1.1); 4.1200 (3.5); 4.1025 (3.8); 4.0847 (1.3); 3.3276 (10.1); 3.1794 (0.7); 3.1662 (0.8); 3.1450 (1.2); 3.1319 (1.0); 3.0567 (1.2); 3.0309 (1.2); 3.0224 (0.8); 2.9966 (0.7); 2.5206 (0.4); 2.5120 (5.0); 2.5075 (10.4); 2.5029 (13.8); 2.4983 (9.8); 2.4937 (4.7); 2.2448 (16.0); 1.1746 (5.2); 1.1569 (11.0); 1.1391 (5.0); 0.0080 (0.3); −0.0002 (9.7)

I.68: $^1$H-NMR(400.2 MHz, $d_6$-DMSO):
δ = 8.6356 (1.1); 8.6165 (1.1); 4.3980 (0.3); 4.3867 (0.5); 4.3787 (0.4); 4.3725 (0.5); 4.3675 (0.6); 4.3604 (0.5); 4.3535 (0.4); 4.3412 (0.4); 4.1565 (0.4); 4.1473 (0.5); 4.1387 (0.5); 4.1352 (0.7); 4.1296 (1.9); 4.1175 (2.0); 4.1117 (2.0); 4.0998 (1.9); 4.0939 (0.7); 4.0906 (0.5); 4.0821 (0.6); 4.0728 (0.4); 3.3259 (11.2); 2.5125 (4.5); 2.5080 (9.2); 2.5035 (12.0); 2.4988 (8.5); 2.4943 (4.0); 2.4106 (16.0); 2.2451 (0.4); 1.7486 (0.4); 1.7339 (0.4); 1.7281 (0.4); 1.7220 (0.6); 1.7166 (0.7); 1.6962 (0.6); 1.6911 (0.6); 1.6845 (0.5); 1.6683 (0.5); 1.6641 (0.5); 1.6517 (0.4); 1.6479 (0.5); 1.5861 (0.6); 1.5736 (0.4); 1.5645 (0.5); 1.5534 (0.8); 1.5422 (0.5); 1.5325 (0.3); 1.2381 (0.5); 1.2104 (4.6); 1.1926 (9.7); 1.1749 (4.5); 0.9266 (5.5); 0.9106 (5.3); 0.8916 (5.2); 0.8756 (5.1); −0.0002 (6.0)

I.69: $^1$H-NMR(400.2 MHz, $d_6$-DMSO):
δ = 8.6361 (1.1); 8.6169 (1.1); 4.3976 (0.4); 4.3864 (0.6); 4.3785 (0.5); 4.3723 (0.6); 4.3673 (0.7); 4.3601 (0.6); 4.3533 (0.4); 4.3409 (0.5); 4.1564 (0.4); 4.1472 (0.6); 4.1385 (0.5); 4.1350 (0.8); 4.1294 (1.9); 4.1174 (2.0); 4.1116 (2.0); 4.0997 (1.9); 4.0938 (0.7); 4.0904 (0.5); 4.0820 (0.6); 4.0726 (0.4); 3.3262 (12.2); 2.5124 (5.0); 2.5079 (10.0); 2.5034 (13.0); 2.4988 (9.2); 2.4943 (4.3); 2.4104 (16.0); 1.7603 (0.3); 1.7484 (0.4); 1.7337 (0.4); 1.7279 (0.4); 1.7217 (0.7); 1.7164 (0.5); 1.6910 (0.6); 1.6843 (0.6); 1.6681 (0.5); 1.6638 (0.5); 1.6514 (0.4); 1.6477 (0.4); 1.5860 (0.6); 1.5735 (0.4); 1.5643 (0.5); 1.5533 (0.9); 1.5420 (0.5); 1.5324 (0.4); 1.2384 (0.4); 1.2101 (4.7); 1.1924 (9.7); 1.1746 (4.5); 0.9264 (5.7); 0.9105 (5.4); 0.8915 (5.4); 0.8755 (5.3); −0.0002 (5.1)

I.70: $^1$H-NMR(400.2 MHz, $d_6$-DMSO):
δ = 8.6774 (0.9); 8.6585 (0.9); 4.5419 (0.3); 4.5273 (0.4); 4.5216 (0.6); 4.5075 (0.6); 4.5021 (0.5); 4.4873 (0.3); 3.6684 (12.4); 3.3256 (8.1); 2.5763 (0.7); 2.5602 (0.8); 2.5580 (0.8); 2.5496 (0.6); 2.5421 (0.6); 2.5299 (1.1); 2.5207 (0.4); 2.5120 (4.2); 2.5076 (7.7); 2.5030 (9.9); 2.4984 (7.2); 2.4939 (3.4); 2.4207 (12.4); 2.0538 (16.0); 2.0441 (1.2); 2.0390 (0.8); 2.0297 (0.8); 2.0229 (0.8); 2.0173 (0.5); 2.0109 (0.3); 2.0021 (0.4); −0.0002 (6.5)

I.71: $^1$H-NMR(400.2 MHz, $d_6$-DMSO):
δ = 8.6773 (0.8); 8.6585 (0.8); 4.5421 (0.3); 4.5275 (0.4); 4.5218 (0.6); 4.5073 (0.6); 4.5023 (0.5); 4.4875 (0.3); 3.6686 (12.3); 3.3254 (6.8); 2.5765 (0.7); 2.5604 (0.8); 2.5582 (0.8); 2.5499 (0.6); 2.5423 (0.6); 2.5302 (1.1); 2.5207 (0.4); 2.5121 (3.8); 2.5077 (6.9); 2.5031 (9.0); 2.4985 (6.6); 2.4940 (3.1); 2.4208 (12.4); 2.0540 (16.0); 2.0444 (1.2); 2.0392 (0.8); 2.0299 (0.8); 2.0232 (0.8); 2.0175 (0.5); 2.0111 (0.3); 2.0024 (0.4); −0.0002 (6.4)

I.72: $^1$H-NMR(400.2 MHz, $d_6$-DMSO):
δ = 8.6773 (0.9); 8.6585 (0.9); 4.5422 (0.4); 4.5275 (0.4); 4.5219 (0.6); 4.5075 (0.6); 4.5024 (0.5); 4.4876 (0.4); 3.6687 (12.3); 3.3252 (6.8); 2.5765 (0.7); 2.5603 (0.8); 2.5582 (0.8); 2.5499 (0.6); 2.5423 (0.6); 2.5302 (1.2); 2.5121 (4.0); 2.5077 (7.3); 2.5031 (9.4); 2.4985 (6.9); 2.4940 (3.3); 2.4209 (12.5); 2.0540 (16.0); 2.0445 (1.3); 2.0393 (0.8); 2.0300 (0.8); 2.0233 (0.8); 2.0176 (0.5); 2.0112 (0.4); 2.0025 (0.4); 1.2384 (0.3); −0.0002 (6.7)

I.73: $^1$H-NMR(400.2 MHz, $d_6$-DMSO):
δ = 8.6973 (1.1); 8.6777 (1.1); 7.3172 (0.3); 7.3146 (0.5); 7.3010 (0.6); 7.2958 (2.6); 7.2946 (2.5); 7.2865 (3.3); 7.2802 (9.7); 7.2696 (0.6); 7.2654 (0.9); 7.2365 (0.7); 7.2310 (0.8); 7.2214 (0.7); 7.2149 (0.9); 7.2117 (0.5); 7.2065 (0.5); 7.1999 (0.4); 4.6336 (0.4); 4.6213 (0.5); 4.6140 (0.5); 4.6073 (0.6); 4.6017 (0.6); 4.5950 (0.5); 4.5877 (0.6); 4.5753 (0.4); 3.6676 (16.0); 3.3296 (11.4); 3.2021 (0.7); 3.1898 (0.7);

TABLE A-continued

NMR peak lists 3.1677 (1.1); 3.1554 (1.0); 3.0565 (1.1); 3.0301 (1.1); 3.0221 (0.8); 2.9957 (0.7); 2.5121 (3.9); 2.5076 (8.2); 2.5030 (10.8); 2.4984 (7.7); 2.4939 (3.7); 2.1967 (15.4); −0.0002 (6.7)
I.74: $^1$H-NMR(400.2 MHz, $d_6$-DMSO):
δ = 8.6444 (1.0); 8.6252 (1.0); 4.4023 (0.4); 4.3909 (0.5); 4.3830 (0.4); 4.3769 (0.5); 4.3719 (0.6); 4.3647 (0.5); 4.3577 (0.4); 4.3454 (0.4); 4.1579 (0.4); 4.1487 (0.5); 4.1400 (0.5); 4.1371 (0.7); 4.1309 (1.8); 4.1194 (1.9); 4.1131 (1.9); 4.1017 (1.8); 4.0953 (0.7); 4.0927 (0.4); 4.0840 (0.6); 4.0747 (0.4); 3.3277 (25.7); 2.5204 (0.5); 2.5119 (6.1); 2.5074 (12.8); 2.5029 (17.2); 2.4983 (12.8); 2.4938 (6.4); 2.3735 (16.0); 1.7554 (0.4); 1.7407 (0.4); 1.7350 (0.4); 1.7289 (0.6); 1.7234 (0.7); 1.6980 (0.8); 1.6861 (0.5); 1.6822 (0.4); 1.6696 (0.5); 1.6654 (0.5); 1.6530 (0.4); 1.6490 (0.4); 1.5908 (0.6); 1.5785 (0.5); 1.5691 (0.4); 1.5580 (0.8); 1.5469 (0.5); 1.5370 (0.4); 1.2393 (0.4); 1.2108 (4.4); 1.1930 (9.1); 1.1753 (4.2); 0.9281 (5.5); 0.9121 (5.3); 0.8924 (5.2); 0.8764 (5.2); −0.0002 (7.9)
I.75: $^1$H-NMR(300.2 MHz, CDCl3):
δ = 7.4618 (0.5); 7.4535 (0.9); 7.4487 (0.7); 7.4404 (1.6); 7.4274 (4.3); 7.4159 (1.2); 7.4097 (3.3); 7.4075 (3.3); 7.4003 (1.1); 7.3918 (1.7); 7.3836 (2.3); 7.3776 (1.2); 7.3640 (0.8); 7.2981 (0.5); 6.9778 (0.7); 6.9559 (0.7); 5.7106 (2.2); 5.6880 (2.2); 4.3311 (0.6); 4.3191 (0.5); 4.3073 (0.6); 4.2953 (1.4); 4.2713 (1.8); 4.2469 (1.8); 4.2230 (1.4); 4.2109 (0.6); 4.1993 (0.5); 4.1872 (0.6); 2.5318 (16.0); 1.2899 (4.2); 1.2661 (8.5); 1.2423 (4.1); 0.0395 (0.5)
I.76: $^1$H-NMR(300.2 MHz, CDCl3):
δ = 7.4610 (0.5); 7.4526 (0.8); 7.4484 (0.7); 7.4396 (1.7); 7.4266 (4.5); 7.4191 (1.4); 7.4158 (1.4); 7.4097 (3.4); 7.4075 (3.2); 7.4001 (1.2); 7.3921 (1.8); 7.3838 (2.2); 7.3644 (0.8); 7.2980 (0.6); 6.9659 (0.7); 6.9439 (0.7); 5.7084 (2.2); 5.6858 (2.2); 4.3301 (0.6); 4.3182 (0.5); 4.3063 (0.7); 4.2943 (1.4); 4.2703 (1.8); 4.2460 (1.8); 4.2221 (1.4); 4.2100 (0.6); 4.1984 (0.5); 4.1862 (0.6); 2.5863 (16.0); 1.2899 (4.2); 1.2661 (8.4); 1.2423 (4.0); 0.0392 (0.6)
I.77: $^1$H-NMR(400.1 MHz, CDCl3):
δ = 7.2631 (10.2); 6.2910 (1.2); 5.0930 (0.4); 5.0824 (0.7); 5.0715 (1.0); 5.0609 (1.4); 5.0504 (1.0); 5.0388 (0.7); 5.0302 (0.3); 4.2055 (5.5); 4.1933 (5.4); 3.9529 (1.2); 3.9418 (2.2); 3.9248 (1.7); 3.9121 (2.5); 3.9010 (1.4); 3.5810 (1.5); 3.5745 (1.7); 3.5517 (2.8); 3.5288 (3.4); 3.5229 (1.4); 2.9579 (1.3); 2.8850 (1.2); 2.5625 (16.0); 1.9798 (1.4); 1.9710 (1.5); 1.9590 (1.4); 1.9462 (1.9); 1.9388 (1.9); 1.7726 (0.8); 1.7629 (0.9); 1.7502 (1.6); 1.7401 (2.1); 1.7290 (1.4); 1.7179 (1.9); 1.7077 (1.2); 1.6958 (0.6); 1.6852 (0.6); 1.5625 (7.0); −0.0002 (6.7)
I.78: $^1$H-NMR(400.1 MHz, CDCl3):
δ = 7.2612 (10.3); 6.3202 (1.0); 5.1470 (0.5); 5.1315 (1.2); 5.1155 (1.5); 5.1001 (1.2); 5.0845 (0.5); 4.1574 (5.4); 4.1453 (5.3); 2.5608 (15.4); 1.5538 (12.7); 1.3017 (16.0); 1.2862 (15.8); −0.0002 (5.0)
I.79: $^1$H-NMR(400.2 MHz, $d_6$-DMSO):
δ = 8.5272 (1.0); 8.5092 (1.0); 4.3603 (1.0); 4.3420 (1.6); 4.3238 (1.0); 2.8918 (0.4); 2.7333 (0.3); 2.7321 (0.3); 2.5124 (4.4); 2.5079 (8.9); 2.5033 (11.7); 2.4987 (8.3); 2.4941 (3.9); 2.4250 (16.0); 1.3709 (6.1); 1.3526 (6.0); −0.0002 (8.9)
I.80: $^1$H-NMR(400.2 MHz, $d_6$-DMSO):
δ = 8.5409 (0.5); 8.5268 (1.0); 8.5123 (0.5); 7.9522 (0.5); 3.8951 (4.0); 3.8805 (4.0); 3.7792 (0.5); 3.6363 (1.2); 3.5437 (1.6); 3.3131 (0.5); 2.8944 (3.4); 2.7358 (2.8); 2.7347 (2.8); 2.5181 (3.6); 2.5137 (7.4); 2.5091 (9.8); 2.5045 (7.2); 2.5000 (3.5); 2.4085 (16.0); −0.0002 (4.1)
I.81: $^1$H-NMR(400.2 MHz, $d_6$-DMSO):
δ = 8.5222 (0.9); 8.5043 (0.9); 7.9535 (1.9); 4.3621 (1.0); 4.3439 (1.5); 4.3257 (1.0); 2.8922 (13.5); 2.7335 (11.5); 2.7324 (11.0); 2.5458 (0.5); 2.5211 (0.3); 2.5126 (4.2); 2.5081 (8.4); 2.5035 (11.0); 2.4989 (7.8); 2.4944 (3.6); 2.3890 (16.0); 1.3757 (6.0); 1.3574 (5.9); −0.0002 (7.0)
I.82: $^1$H-NMR(400.2 MHz, $d_6$-DMSO):
δ = 8.3653 (1.0); 8.3452 (1.0); 7.9534 (0.4); 4.2186 (1.1); 4.2028 (1.2); 4.1985 (1.2); 4.1827 (1.1); 2.8922 (2.8); 2.7336 (2.3); 2.7323 (2.3); 2.5477 (0.5); 2.5211 (0.3); 2.5125 (4.3); 2.5080 (9.3); 2.5034 (12.2); 2.4988 (8.8); 2.4943 (4.2); 2.4457 (1.1); 2.3771 (16.0); 2.3708 (1.7); 2.1931 (0.5); 2.1763 (0.8); 2.1597 (0.8); 2.1429 (0.5); 0.9605 (10.5); 0.9434 (10.2); 0.9305 (0.5); 0.9183 (0.4); 0.9143 (0.5); 0.9025 (0.6); 0.8973 (0.4); 0.8862 (0.3); 0.0080 (0.3); −0.0002 (8.8)
I.83: $^1$H-NMR(400.1 MHz, $d_6$-DMSO):
δ = 8.2727 (2.2); 8.2525 (2.1); 7.9603 (1.5); 4.4433 (1.6); 4.4275 (2.1); 4.4112 (1.5); 3.3334 (18.0); 3.0685 (0.3); 2.8999 (6.7); 2.7406 (6.3); 2.5101 (8.9); 2.3781 (16.0); 1.9992 (1.2); 1.9830 (1.6); 1.9674 (1.3); 1.4459 (0.6); 1.4294 (1.0); 1.4122 (1.4); 1.3949 (1.3); 1.3786 (0.9); 1.2528 (0.9); 1.2359 (1.4); 1.2186 (1.4); 1.2015 (1.1); 1.1829 (0.6); 0.9330 (8.6); 0.9156 (12.1); 0.8961 (8.5); 0.8780 (4.0)
I.84: $^1$H-NMR(400.2 MHz, $d_6$-DMSO):
δ = 8.5037 (1.1); 8.4838 (1.1); 7.9536 (0.7); 4.3579 (0.5); 4.3482 (0.4); 4.3427 (0.5); 4.3381 (0.6); 4.3315 (0.5); 4.3232 (0.4); 4.3116 (0.4); 2.8924 (4.8); 2.7338 (3.9); 2.7327 (4.1); 2.5475 (0.5); 2.5127 (4.9); 2.5083 (10.1); 2.5037 (13.4); 2.4991 (9.7); 2.4946 (4.7); 2.4386 (0.8); 2.3790 (16.0); 2.3711 (1.4); 1.7447 (0.4); 1.7289 (0.4); 1.7238 (0.4); 1.7174 (0.7); 1.7137 (0.7); 1.6983 (0.5); 1.6870 (0.8); 1.6709 (0.5); 1.6663 (0.5); 1.6545 (0.4); 1.6502 (0.4); 1.6027 (0.6); 1.5907 (0.4); 1.5809 (0.8); 1.5706 (0.8); 1.5600 (0.4); 0.9239 (5.3); 0.9080 (5.2); 0.8901 (5.0); 0.8743 (4.9); −0.0002 (8.0)
I.85: $^1$H-NMR(400.1 MHz, $d_6$-DMSO):
δ = 8.5180 (1.9); 8.4991 (1.9); 7.9602 (0.8); 4.4520 (1.4); 4.4400 (1.4); 3.3307 (19.0); 2.8989 (3.5); 2.7400 (3.2); 2.5779 (1.5); 2.5580 (2.4); 2.5368 (2.6); 2.5103 (10.0); 2.3957 (13.6); 2.0614 (16.0); 2.0039 (0.8); 1.2642 (0.4); 1.2477 (0.4)
I.86: $^1$H-NMR(400.2 MHz, $d_6$-DMSO):
δ = 8.5160 (1.3); 8.4958 (1.3); 7.9534 (1.4); 7.2874 (7.4); 7.2764 (12.3); 7.2659 (0.7); 7.2241 (0.8); 7.2130 (1.2); 7.2024 (1.3); 7.1948 (0.5); 7.1907 (0.7); 4.5618 (0.4); 4.5507 (0.5); 4.5414 (0.5); 4.5351 (0.7); 4.5310 (0.6); 4.5244 (0.5); 4.5152 (0.5); 4.5041 (0.4); 3.2195 (0.8); 3.2084 (0.9); 3.1850 (1.1); 3.1740 (1.0); 3.0347 (1.1); 3.0080 (1.1); 3.0003 (0.9); 2.9736 (0.8); 2.8909 (10.4); 2.7331 (8.7); 2.7320 (8.6); 2.5451 (0.6); 2.5209 (0.5); 2.5123 (6.5); 2.5078 (13.6); 2.5033 (18.0); 2.4987 (13.0); 2.4941 (6.3); 2.4423 (0.5); 2.1912 (16.0); 0.0080 (0.4); −0.0002 (11.9); −0.0085 (0.4)
I.87: $^1$H-NMR(400.1 MHz, $d_6$-DMSO):
δ = 8.5093 (2.0); 8.4904 (2.0); 7.9600 (1.2); 4.4403 (1.5); 4.4292 (1.4); 3.5729 (0.4); 3.5582 (0.4); 3.3284 (60.1); 3.0720 (0.4); 2.8997 (5.2); 2.7405 (4.9); 2.5733 (1.7); 2.5542 (2.8); 2.5106 (17.5); 2.4335 (13.7); 2.0606 (16.0); 1.9943 (1.0); 1.2598 (0.5); 1.2435 (0.5)

TABLE A-continued

NMR peak lists

I.88: $^1$H-NMR(400.1 MHz, d$_6$-DMSO):
δ = 8.5092 (2.3); 8.4901 (2.3); 7.9603 (2.4); 7.2839 (14.4); 7.2212 (2.1); 4.5415 (1.7); 3.3304 (51.8); 3.2177 (2.5); 3.1836 (2.6); 3.0679 (0.4); 3.0349 (1.8); 3.0061 (2.2); 2.9731 (1.3); 2.8984 (10.5); 2.7397 (10.0); 2.5105 (13.6); 2.2400 (16.0)

I.89: $^1$H-NMR(499.9 MHz, d$_6$-DMSO):
δ = 12.7827 (1.0); 8.2866 (2.9); 8.2699 (2.9); 4.4317 (2.5); 4.4215 (2.7); 4.4150 (2.6); 4.4047 (2.5); 3.3170 (3.0); 2.5116 (5.3); 2.5081 (11.0); 2.5046 (15.1); 2.5010 (11.0); 2.4975 (5.2); 2.4072 (38.2); 1.9991 (0.6); 1.9856 (1.4); 1.9731 (1.7); 1.9605 (1.4); 1.9470 (0.7); 1.4296 (0.9); 1.4162 (1.4); 1.4020 (2.0); 1.3877 (1.7); 1.3743 (1.2); 1.3597 (0.3); 1.2397 (1.2); 1.2249 (2.0); 1.2104 (1.7); 1.1975 (1.6); 1.1827 (1.0); 0.9221 (15.5); 0.9083 (15.9); 0.9035 (9.2); 0.8886 (16.0); 0.8738 (6.7)

I.90: $^1$H-NMR(300.2 MHz, d$_6$-DMSO):
δ = 12.7133 (0.7); 8.5333 (2.7); 8.5069 (2.8); 4.3890 (0.6); 4.3748 (1.2); 4.3624 (0.9); 4.3484 (1.5); 4.3400 (1.2); 4.3284 (0.7); 4.3136 (0.9); 3.3524 (16.0); 2.5339 (5.4); 2.5280 (11.2); 2.5219 (15.3); 2.5159 (11.2); 2.5101 (5.4); 2.4326 (33.0); 2.0956 (0.3); 1.7793 (0.5); 1.7648 (0.9); 1.7283 (2.0); 1.6984 (1.8); 1.6821 (1.5); 1.6639 (1.0); 1.6432 (0.8); 1.6170 (1.5); 1.5912 (0.8); 1.5778 (1.5); 1.5638 (0.6); 1.5513 (0.5); 0.9422 (10.2); 0.9217 (10.2); 0.9083 (10.3); 0.8876 (10.0); 0.0304 (0.4); 0.0194 (9.8); 0.0083 (0.4)

I.91: $^1$H-NMR(300.2 MHz, CDCl3):
δ = 7.2994 (2.8); 6.3458 (0.5); 6.3191 (0.5); 4.7660 (1.2); 4.7507 (1.2); 4.7379 (1.1); 4.7226 (1.1); 3.8211 (16.0); 2.5383 (15.5); 2.3377 (0.5); 2.3220 (0.5); 2.3148 (0.7); 2.2994 (0.7); 2.2919 (0.6); 2.2765 (0.5); 1.0442 (6.6); 1.0213 (6.6); 1.0101 (6.9); 0.9871 (6.5); 0.0350 (0.9)

I.92: $^1$H-NMR(300.2 MHz, CDCl3):
δ = 7.2990 (0.8); 6.4532 (1.3); 3.7374 (16.0); 2.5560 (15.5); 1.7066 (1.0); 1.7009 (1.2); 1.6839 (3.2); 1.6730 (3.4); 1.6578 (1.4); 1.3263 (1.4); 1.3108 (3.4); 1.3001 (3.3); 1.2833 (1.2); 0.0278 (1.0)

IVa.01: 1H-NMR(300.2 MHz, d6-DMSO):
δ = 4.0799 (5.3); 4.0586 (5.4); 3.3415 (4.9); 2.5524 (17.9); 2.5343 (0.7); 2.5282 (1.2); 2.5221 (1.7); 2.5160 (1.2); 2.5100 (0.6); 2.0454 (0.4); 2.0232 (0.8); 2.0010 (1.0); 1.9789 (0.8); 1.9568 (0.4); 1.2627 (0.6); 0.9753 (16.0); 0.9529 (15.3); 0.8761 (0.6); 0.0180 (1.3)

IVa.02: 1H-NMR(499.9 MHz, CDCl3):
δ = 7.2622 (1.9); 4.3528 (1.2); 4.3385 (4.0); 4.3242 (4.3); 4.3100 (1.9); 2.5262 (16.0); 2.4981 (1.1); 1.3792 (4.2); 1.3650 (8.5); 1.3507 (5.1); 1.3366 (1.2); 1.2972 (0.6); 1.2845 (0.7); 1.2536 (5.5); 1.1056 (0.3); 0.8885 (0.6); 0.8799 (0.9); 0.8739 (0.8); 0.8656 (0.9); 0.8558 (1.0); 0.8412 (0.9); −0.0002 (1.7)

IVa.03: 1H-NMR(400.1 MHz, d6-DMSO):
δ = 4.0712 (5.4); 4.0552 (5.4); 3.3163 (4.8); 2.5139 (1.6); 2.5096 (2.2); 2.5053 (1.6); 2.4861 (17.1); 2.0251 (0.5); 2.0085 (0.9); 1.9919 (1.2); 1.9753 (1.0); 1.9587 (0.5); 0.9630 (16.0); 0.9462 (15.5)

VIa.01: 1H-NMR(300.2 MHz, CDCl3):
δ = 7.7266 (0.9); 7.2983 (1.8); 4.3473 (2.2); 4.3235 (6.6); 4.2997 (6.8); 4.2799 (9.4); 4.2639 (8.9); 1.6684 (1.5); 1.3796 (8.0); 1.3558 (16.0); 1.3319 (7.7); 0.0290 (2.0)

VIa.02: 1H-NMR(300.2 MHz, CDCl3):
δ = 7.6832 (0.5); 7.2980 (1.8); 4.3203 (5.0); 4.3043 (4.9); 3.8640 (16.0); 1.6217 (0.6); 0.0330 (2.2)

VIa.03: 1H-NMR(300.2 MHz, CDCl3):
δ = 7.6908 (0.5); 7.2986 (3.4); 4.3181 (4.8); 4.3021 (4.8); 3.8644 (16.0); 2.0812 (0.4); 1.6018 (1.6); 0.0358 (4.1)

VIa.04: 1H-NMR(400.2 MHz, d6-DMSO):
δ = 9.0297 (2.9); 4.1005 (2.1); 4.0828 (6.7); 4.0651 (6.7); 4.0473 (2.1); 3.3285 (11.9); 2.5220 (0.4); 2.5133 (6.0); 2.5088 (12.5); 2.5042 (16.6); 2.4995 (12.0); 2.4950 (5.9); 1.4637 (1.8); 1.4515 (4.4); 1.4431 (4.8); 1.4322 (2.0); 1.1946 (2.2); 1.1820 (10.0); 1.1753 (4.9); 1.1641 (16.0); 1.1463 (7.1); −0.0002 (0.4)

VIa.05: 1H-NMR(499.9 MHz, d6-DMSO):
δ = 9.1058 (3.8); 4.1569 (2.1); 4.1426 (6.5); 4.1284 (6.6); 4.1143 (2.1); 3.3757 (1.0); 2.5650 (0.4); 2.5615 (0.8); 2.5579 (1.0); 2.5543 (0.8); 2.5508 (0.4); 1.5126 (1.8); 1.5030 (4.7); 1.4964 (5.0); 1.4875 (2.0); 1.2481 (7.1); 1.2338 (16.0); 1.2238 (5.6); 1.2196 (9.1); 1.2076 (1.9)

VIa.06: 1H-NMR(300.2 MHz, d6-DMSO):
δ = 12.5912 (0.3); 12.5704 (0.3); 8.9622 (5.6); 3.3582 (16.0); 2.5348 (7.3); 2.5289 (15.6); 2.5228 (21.8); 2.5167 (15.8); 2.5108 (7.3); 1.4582 (2.0); 1.4422 (5.0); 1.4314 (5.7); 1.4172 (2.5); 1.1587 (2.6); 1.1445 (5.5); 1.1336 (5.4); 1.1178 (2.0); 0.0317 (1.0); 0.0207 (30.4); 0.0098 (1.1)

VIa.07: 1H-NMR(400.2 MHz, d6-DMSO):
δ = 9.0605 (4.1); 8.3150 (0.5); 4.1032 (2.2); 4.0855 (7.1); 4.0677 (7.1); 4.0500 (2.3); 3.3287 (15.8); 2.8923 (0.7); 2.7326 (0.6); 2.5263 (0.4); 2.5216 (0.6); 2.5128 (8.7); 2.5084 (18.0); 2.5038 (23.9); 2.4992 (17.7); 2.4948 (8.9); 1.4546 (1.8); 1.4425 (4.6); 1.4343 (5.1); 1.4233 (2.1); 1.1961 (7.7); 1.1783 (16.0); 1.1693 (2.6); 1.1604 (9.6); 1.1499 (5.1); 1.1378 (1.8); −0.0002 (0.5)

VIa.08: 1H-NMR(300.2 MHz, d6-DMSO):
δ = 9.0801 (2.6); 3.6446 (16.0); 3.3477 (11.1); 2.5279 (2.3); 2.5220 (3.1); 2.5161 (2.2); 1.4960 (1.0); 1.4795 (2.8); 1.4685 (3.1); 1.4541 (1.3); 1.2106 (1.4); 1.1961 (3.1); 1.1851 (2.9); 1.1685 (1.1); 0.0189 (2.7)

VIa.09: 1H-NMR(300.2 MHz, d6-DMSO):
δ = 12.6292 (0.5); 12.5891 (0.6); 12.5706 (0.6); 12.5368 (0.5); 8.9512 (15.1); 6.8906 (0.3); 3.3471 (16.0); 2.5343 (14.3); 2.5283 (29.9); 2.5222 (40.7); 2.5161 (28.9); 2.5102 (13.1); 2.2042 (0.5); 2.0093 (1.1); 1.9289 (0.4); 1.4951 (0.3); 1.4457 (5.1); 1.4297 (12.6); 1.4189 (14.1); 1.4050 (6.2); 1.3753 (4.2); 1.3509 (0.6); 1.2561 (0.6); 1.2184 (0.5); 1.2012 (1.5); 1.1949 (1.1); 1.1708 (0.7); 1.1518 (6.7); 1.1379 (14.3); 1.1271 (13.5); 1.1112 (5.0); 0.0308 (1.6); 0.0200 (45.4); 0.0090 (1.5)

VIa.10: 1H-NMR(400.2 MHz, d6-DMSO):
δ = 8.7446 (0.8); 8.7304 (1.7); 8.7161 (0.8); 4.1608 (2.2); 4.1430 (7.0); 4.1252 (7.1); 4.1075 (2.3); 4.0177 (6.3); 4.0032 (6.3); 3.3296 (12.4); 2.8929 (0.6); 2.7342 (0.5); 2.7332 (0.5); 2.5270 (0.4); 2.5223 (0.6); 2.5135 (7.2); 2.5091 (14.7); 2.5045 (19.2); 2.4999 (13.9); 2.4954 (6.7); 1.2357 (8.0); 1.2179 (16.0); 1.2001 (7.6); −0.0002 (0.4)

VIa.11: 1H-NMR(400.2 MHz, d6-DMSO):
δ = 8.5453 (1.5); 8.5258 (1.5); 4.3175 (1.6); 4.3022 (1.8); 4.2980 (1.8); 4.2826 (1.6); 4.2026 (1.0); 4.1934 (0.8); 4.1849 (1.0); 4.1757 (2.7); 4.1664 (1.2); 4.1579 (2.9); 4.1485 (2.9); 4.1399 (1.2); 4.1308 (2.8); 4.1215 (1.1); 4.1131 (0.9); 4.1037 (1.1); 4.0860 (0.3); 3.3279 (12.9); 2.8931 (0.9); 2.7344 (0.7); 2.7330

TABLE A-continued

NMR peak lists (0.7); 2.5268 (0.4); 2.5221 (0.6); 2.5134 (8.1); 2.5089 (16.5); 2.5043 (21.5); 4.2996 (15.3); 2.4951 (7.2);
2.2143 (0.8); 2.1976 (1.2); 2.1813 (1.3); 2.1645 (0.8); 1.2379 (7.9); 1.2201 (16.0); 1.2023 (7.4); 0.9932
(9.5); 0.9770 (14.5); 0.9607 (8.7); −0.0002 (0.5)

VIa.12: 1H-NMR(499.9 MHz, d6-DMSO):
δ = 8.7100 (1.0); 8.6988 (1.8); 8.6874 (0.9); 4.1628 (2.4); 4.1486 (7.0); 4.1343 (7.0); 4.1201 (2.2); 4.0351
(6.9); 4.0236 (6.7); 3.3227 (1.6); 2.5139 (0.4); 2.5104 (0.7); 2.5067 (0.9); 2.5031 (0.6); 1.2367 (8.0);
1.2224 (16.0); 1.2082 (7.6)

VIa.13: 1H-NMR(300.2 MHz, d6-DMSO):
δ = 8.5980 (0.5); 3.9800 (1.7); 3.9611 (1.7); 3.3447 (16.0); 2.5345 (3.3); 2.5285 (7.1); 2.5224 (9.9); 2.5164
(7.2); 2.5104 (3.3); 2.0099 (0.4); 0.0317 (0.4); 0.0208 (14.2); 0.0098 (0.5)

VIa.14: 1H-NMR(400.2 MHz, d6-DMSO):
δ = 8.7570 (1.9); 8.7380 (2.0); 7.3230 (0.9); 7.3202 (1.4); 7.3165 (0.6); 7.3022 (4.0); 7.2996 (3.1); 7.2899
(1.2); 7.2846 (5.3); 7.2719 (4.3); 7.2678 (6.6); 7.2614 (1.1); 7.2511 (2.6); 7.2465 (2.4); 7.2426 (1.6);
7.2375 (0.8); 7.2308 (0.9); 7.2248 (2.4); 7.2178 (0.5); 7.2120 (0.5); 7.2075 (0.8); 7.2034 (0.4); 4.6413
(0.6); 4.6273 (0.8); 4.6188 (1.1); 4.6081 (1.0); 4.6050 (1.3); 4.5998 (0.9); 4.5857 (0.7); 4.1411 (1.5);
4.1235 (4.8); 4.1064 (5.2); 4.0887 (1.8); 3.3294 (20.9); 3.1759 (0.9); 3.1620 (1.0); 3.1414 (1.8); 3.1277
(1.6); 3.0775 (1.7); 3.0546 (1.7); 3.0431 (1.0); 3.0202 (0.9); 2.8913 (1.0); 2.7333 (0.8); 2.7322 (0.8);
2.5258 (0.6); 2.5210 (0.8); 2.5124 (11.3); 2.5080 (22.9); 2.5034 (29.8); 2.4988 (21.4); 2.4942 (10.2);
1.1871 (7.6); 1.1693 (16.0); 1.1515 (7.3); −0.0002 (0.6)

VIa.15: 1H-NMR(400.2 MHz, d6-DMSO):
δ = 8.7592 (1.8); 8.7404 (1.9); 4.4041 (0.7); 4.3918 (0.7); 4.3852 (0.9); 4.3786 (1.1); 4.3731 (0.9); 4.3669
(0.8); 4.3599 (0.9); 4.3479 (0.6); 4.1667 (0.6); 4.1575 (1.0); 4.1488 (0.8); 4.1459 (1.2); 4.1397 (3.2);
4.1282 (3.4); 4.1219 (3.4); 4.1104 (3.3); 4.1041 (1.3); 4.1015 (1.0); 4.0927 (1.0); 4.0835 (0.7); 3.3280
(13.4); 2.8930 (1.0); 2.7334 (0.9); 2.5267 (0.4); 2.5219 (0.6); 2.5132 (9.0); 2.5088 (18.2); 2.5043 (23.9);
2.4997 (17.3); 2.4952 (8.4); 1.7758 (0.5); 1.7706 (0.5); 1.7624 (0.8); 1.7563 (1.1); 1.7469 (1.5); 1.7284
(1.2); 1.7211 (1.6); 1.7085 (0.8); 1.6956 (1.1); 1.6830 (0.8); 1.6100 (0.6); 1.6055 (0.5); 1.5938 (1.0);
1.5838 (0.9); 1.5721 (1.6); 1.5606 (0.8); 1.5480 (0.4); 1.5380 (0.5); 1.2249 (7.8); 1.2072 (16.0); 1.1894
(7.5); 0.9325 (9.4); 0.9165 (9.4); 0.9040 (9.2); 0.8879 (8.8); −0.0002 (0.5)

VIa.16: 1H-NMR(400.2 MHz, d6-DMSO):
δ = 8.8160 (1.0); 8.7974 (1.0); 4.5250 (0.4); 4.5112 (0.5); 4.5045 (0.7); 4.4913 (0.6); 4.4853 (0.5); 4.4715
(0.4); 4.1686 (0.5); 4.1583 (0.7); 4.1508 (1.6); 4.1404 (1.7); 4.1329 (1.7); 4.1227 (1.7); 4.1146 (0.7);
4.1049 (0.5); 3.3280 (6.7); 2.6263 (0.7); 2.6105 (1.3); 2.5910 (1.7); 2.5721 (0.7); 2.5662 (0.4); 2.5566
(0.6); 2.5128 (4.9); 2.5084 (9.7); 2.5039 (12.6); 2.4993 (9.2); 2.4949 (4.5); 2.0655 (16.0); 2.0549 (1.0);
2.0455 (0.9); 2.0413 (0.8); 2.0300 (0.7); 2.0253 (0.6); 2.0095 (0.4); 1.2317 (3.8); 1.2242 (0.6); 1.2139
(7.7); 1.1961 (3.6)

VIa.17: 1H-NMR(400.2 MHz, d6-DMSO):
δ = 8.4679 (1.4); 8.4484 (1.4); 4.3306 (1.8); 4.3155 (2.0); 4.3111 (2.0); 4.2960 (1.8); 4.2263 (0.3); 4.2085
(1.1); 4.1993 (0.9); 4.1908 (1.1); 4.1815 (2.9); 4.1701 (1.1); 4.1637 (3.0); 4.1523 (3.0); 4.1460 (1.1);
4.1346 (3.0); 4.1253 (1.2); 4.1169 (0.9); 4.1076 (1.1); 4.0898 (0.4); 3.3272 (13.7); 2.5269 (0.4); 2.5222
(0.6); 2.5135 (7.8); 2.5091 (15.6); 2.5045 (20.3); 2.4999 (14.6); 2.4954 (7.0); 2.2189 (0.9); 2.2021 (1.4);
2.1861 (1.4); 2.1693 (0.9); 1.2350 (8.1); 1.2172 (16.0); 1.1995 (7.6); 0.9813 (10.9); 0.9679 (12.2); 0.9644
(12.1); 0.9509 (10.0); −0.0002 (0.4)

VIa.18: 1H-NMR(400.2 MHz, d6-DMSO):
δ = 8.7118 (1.5); 8.6928 (1.5); 4.4275 (0.5); 4.4158 (0.9); 4.4087 (0.7); 4.4029 (0.8); 4.3968 (1.0); 4.3907
(0.9); 4.3840 (0.6); 4.3717 (0.7); 4.1696 (0.6); 4.1605 (1.0); 4.1500 (1.2); 4.1427 (3.1); 4.1322 (3.3);
4.1248 (3.3); 4.1144 (3.2); 4.1069 (1.2); 4.0968 (1.0); 4.0874 (0.6); 3.3279 (16.2); 2.8936 (1.4); 2.7345
(1.2); 2.7333 (1.1); 2.5269 (0.4); 2.5221 (0.6); 2.5134 (7.8); 2.5090 (15.8); 2.5044 (20.5); 2.4997 (14.6);
2.4952 (6.9); 1.7756 (0.5); 1.7632 (0.8); 1.7497 (0.5); 1.7377 (1.2); 1.7310 (1.5); 1.7139 (1.9); 1.7012
(1.0); 1.6850 (0.4); 1.6146 (0.7); 1.6003 (0.8); 1.5888 (1.5); 1.5772 (0.8); 1.2332 (0.3); 1.2201 (7.7);
1.2024 (16.0); 1.1846 (7.4); 0.9318 (8.4); 0.9160 (8.0); 0.9001 (8.0); 0.8841 (7.6); −0.0002 (0.4)

VIa.19: 1H-NMR(400.2 MHz, d6-DMSO):
δ = 8.7776 (0.7); 8.7591 (0.8); 4.5404 (0.4); 4.5346 (0.6); 4.5210 (0.5); 4.5154 (0.4); 4.5011 (0.3); 4.1724
(0.4); 4.1634 (0.7); 4.1545 (1.5); 4.1454 (1.7); 4.1367 (1.6); 4.1277 (1.5); 4.1187 (0.8); 4.1100 (0.5);
3.3275 (6.3); 2.8934 (0.8); 2.7345 (0.7); 2.7331 (0.7); 2.6019 (0.6); 2.5865 (1.1); 2.5834 (0.9); 2.5671
(1.6); 2.5518 (0.4); 2.5487 (0.6); 2.5134 (3.5); 2.5088 (7.0); 2.5042 (9.2); 2.4996 (6.6); 2.4950 (3.2);
2.0904 (0.4); 2.0854 (0.4); 2.0764 (0.5); 2.0714 (0.9); 2.0602 (16.0); 2.0491 (0.8); 2.0451 (0.6); 2.0389
(0.4); 2.0286 (0.4); 1.2275 (3.7); 1.2189 (0.3); 1.2098 (7.6); 1.1920 (3.5)

VIa.20: 1H-NMR(400.2 MHz, d6-DMSO):
δ = 8.6332 (1.6); 8.6144 (1.6); 7.3226 (0.8); 7.3198 (1.3); 7.3160 (0.6); 7.3018 (3.7); 7.2993 (3.2); 7.2900
(1.2); 7.2843 (5.4); 7.2746 (4.6); 7.2706 (6.8); 7.2641 (1.0); 7.2541 (2.4); 7.2498 (1.4); 7.2465 (1.6);
7.2428 (1.5); 7.2374 (0.8); 7.2312 (0.9); 7.2251 (2.3); 7.2180 (0.5); 7.2128 (0.5); 7.2080 (0.8); 7.2038
(0.4); 4.6760 (0.7); 4.6622 (0.9); 4.6569 (1.0); 4.6537 (1.2); 4.6432 (1.0); 4.6401 (1.0); 4.6348 (1.0);
4.6209 (0.7); 4.1481 (1.5); 4.1317 (4.6); 4.1304 (4.6); 4.1138 (5.0); 4.0959 (1.7); 3.3305 (17.0); 3.2003
(0.9); 3.1866 (1.0); 3.1658 (1.8); 3.1522 (1.7); 3.1031 (1.8); 3.0805 (1.8); 3.0687 (1.0); 3.0461 (1.0);
2.8916 (1.0); 2.7338 (0.8); 2.7327 (0.9); 2.5264 (0.4); 2.5216 (0.6); 2.5129 (8.5); 2.5085 (17.0); 2.5039
(22.1); 2.4993 (15.9); 2.4947 (7.6); 1.1861 (7.7); 1.1684 (16.0); 1.1506 (7.4); −0.0002 (0.4)

VIa.21: 1H-NMR(400.2 MHz, d6-DMSO):
δ = 8.5103 (1.4); 8.4908 (1.4); 4.3318 (1.4); 4.3166 (1.7); 4.3124 (1.6); 4.2971 (1.4); 4.2063 (0.8); 4.1970
(0.7); 4.1885 (0.8); 4.1793 (2.2); 4.1704 (1.0); 4.1615 (2.3); 4.1526 (2.3); 4.1436 (1.0); 4.1348 (2.3);
4.1256 (0.8); 4.1171 (0.7); 4.1078 (0.8); 3.3229 (19.1); 2.5250 (0.5); 2.5117 (10.5); 2.5073 (21.4); 2.5028
(28.2); 2.4983 (20.2); 2.4938 (9.7); 2.2231 (0.7); 2.2063 (1.2); 2.1900 (1.2); 2.1733 (0.8); 1.2391 (6.6);
1.2214 (13.0); 1.2036 (6.0); 0.9988 (8.7); 0.9816 (16.0); 0.9643 (8.0); −0.0002 (5.3)

VIa.22: 1H-NMR(400.2 MHz, d6-DMSO):
δ = 8.7477 (2.1); 8.7289 (2.1); 4.4118 (0.8); 4.3994 (0.8); 4.3928 (1.0); 4.3867 (1.2); 4.3809 (0.9); 4.3749
(0.8); 4.3680 (1.0); 4.3560 (0.6); 4.1690 (0.6); 4.1597 (1.0); 4.1486 (1.3); 4.1420 (3.2); 4.1308 (3.4);
4.1242 (3.4); 4.1131 (3.2); 4.1062 (1.3); 4.0954 (1.0); 4.0861 (0.6); 3.3229 (26.7); 2.5250 (0.7); 2.5113
(14.8); 2.5070 (30.5); 2.5026 (40.5); 2.4981 (29.6); 2.4937 (14.6); 1.7949 (0.3); 1.7786 (0.6); 1.7621 (1.3);
1.7531 (1.4); 1.7303 (2.0); 1.7178 (0.9); 1.7047 (1.3); 1.6920 (0.8); 1.6176 (0.6); 1.6015 (1.0); 1.5916

TABLE A-continued

NMR peak lists (0.9); 1.5799 (1.7); 1.5684 (0.8); 1.5549 (0.4); 1.5458 (0.5); 1.2389 (0.7); 1.2251 (7.8); 1.2074 (16.0); 1.1896 (7.6); 0.9345 (9.8); 0.9186 (9.9); 0.9051 (9.7); 0.8891 (9.4); −0.0002 (7.2)
VIa.23: 1H-NMR(400.2 MHz, d6-DMSO):
δ = 8.8083 (1.0); 8.7898 (1.0); 4.5337 (0.3); 4.5137 (0.6); 4.4998 (0.6); 4.4947 (0.5); 4.4804 (0.3); 4.1713 (0.5); 4.1613 (0.6); 4.1535 (1.5); 4.1433 (1.6); 4.1356 (1.6); 4.1256 (1.5); 4.1174 (0.7); 4.1079 (0.5); 3.3232 (10.4); 2.6291 (0.7); 2.6137 (1.3); 2.5945 (1.7); 2.5761 (0.7); 2.5613 (0.3); 2.5115 (6.4); 2.5071 (13.2); 2.5026 (17.5); 2.4981 (12.8); 2.4937 (6.3); 2.0813 (0.5); 2.0662 (16.0); 2.0485 (0.8); 2.0389 (0.8); 2.0304 (0.4); 2.0185 (0.4); 1.2323 (3.7); 1.2146 (7.5); 1.1968 (3.5); −0.0002 (3.4)
VIa.24: 1H-NMR(400.2 MHz, d6-DMSO):
δ = 8.7327 (2.0); 8.7139 (2.0); 7.3206 (1.4); 7.3025 (4.2); 7.2902 (1.4); 7.2847 (5.6); 7.2683 (7.1); 7.2515 (2.8); 7.2471 (2.6); 7.2432 (1.8); 7.2312 (1.0); 7.2254 (2.4); 7.2187 (0.5); 7.2126 (0.5); 7.2082 (0.8); 4.6559 (0.7); 4.6418 (1.0); 4.6337 (1.2); 4.6227 (1.1); 4.6199 (1.1); 4.6146 (1.0); 4.6006 (0.7); 4.1446 (1.6); 4.1374 (0.3); 4.1271 (5.3); 4.1096 (5.6); 4.0996 (0.3); 4.0919 (1.9); 3.3249 (32.0); 3.1832 (1.0); 3.1692 (1.1); 3.1487 (2.0); 3.1349 (1.8); 3.0878 (1.9); 3.0651 (1.9); 3.0534 (1.1); 3.0307 (1.0); 2.8912 (0.4); 2.7321 (0.3); 2.5246 (0.8); 2.5113 (17.7); 2.5070 (35.1); 2.5025 (45.5); 2.4979 (32.5); 2.4935 (15.5); 1.2389 (0.6); 1.1887 (7.7); 1.1709 (16.0); 1.1532 (7.4); −0.0002 (7.0)
VIIIa.01: 1H-NMR(499.9 MHz, CDCl3):
δ = 7.2672 (1.2); 4.4055 (2.5); 4.3912 (7.7); 4.3769 (7.8); 4.3627 (2.6); 2.0088 (0.9); 1.4065 (8.0); 1.3922 (16.0); 1.3780 (8.0); 1.2628 (0.4); 1.2538 (1.0); −0.0002 (1.4)
VIIIa.02: 1H-NMR(300.2 MHz, CDCl3):
δ = 7.6041 (0.4); 7.2984 (2.1); 3.9506 (16.0); 3.9244 (1.2); 1.5852 (1.8); 0.0364 (2.4)
VIIIa.03: 1H-NMR(499.9 MHz, d6-DMSO):
δ = 15.1027 (0.3); 14.9975 (0.4); 14.9759 (0.4); 14.9509 (0.4); 14.9312 (0.4); 14.8896 (0.4); 14.8671 (0.5); 14.8450 (0.5); 14.7865 (0.6); 14.7539 (0.7); 14.6142 (1.0); 14.5943 (1.2); 14.5485 (1.4); 14.5271 (1.5); 14.5236 (1.5); 14.2968 (4.7); 14.1541 (7.0); 14.0699 (5.8); 13.9449 (3.2); 13.8394 (2.0); 13.5699 (0.8); 13.5440 (0.8); 13.4921 (0.6); 13.4731 (0.6); 13.4502 (0.6); 13.4216 (0.6); 13.3628 (0.5); 13.3451 (0.5); 13.3306 (0.4); 13.2703 (0.5); 13.2252 (0.4); 13.2010 (0.4); 13.1591 (0.4); 13.1269 (0.3); 13.0464 (0.3); 7.7544 (8.9); 7.4284 (1.4); 4.5359 (0.3); 4.4060 (0.3); 4.3940 (0.3); 4.3632 (0.4); 4.3500 (0.4); 4.3401 (0.4); 4.2742 (0.4); 4.2369 (0.4); 4.2278 (0.5); 4.2094 (0.5); 4.1782 (0.5); 4.1293 (0.5); 4.1189 (0.6); 4.1132 (0.6); 4.1025 (0.6); 4.0515 (0.6); 4.0446 (0.7); 4.0191 (0.7); 3.9836 (0.8); 3.9763 (0.8); 3.9301 (0.9); 3.8612 (1.0); 3.4109 (6.4); 3.3496 (7.0); 3.1621 (3.7); 2.8672 (1.0); 2.8488 (1.0); 2.8394 (0.9); 2.8120 (0.8); 2.8052 (0.8); 2.7588 (0.9); 2.7233 (0.7); 2.7027 (0.7); 2.6458 (1.7); 2.6421 (2.1); 2.6172 (0.7); 2.5952 (0.7); 2.5818 (0.7); 2.5143 (96.0); 2.5108 (196.0); 2.5072 (264.8); 2.5037 (189.8); 2.5002 (88.3); 2.3720 (1.1); 2.3683 (1.6); 2.3644 (1.2); 2.1856 (0.5); 2.0896 (16.0); 2.0780 (0.4); 1.9135 (0.5); 1.3579 (3.0); 1.3421 (1.0); 1.3177 (0.4); 1.3006 (1.0); 1.2736 (0.5); 1.2600 (1.1); 1.2307 (1.5); 1.2053 (0.4); 1.1833 (2.4); 1.1716 (1.1); 1.0969 (0.4); 0.8541 (0.5)
VIIIa.04: 1H-NMR(499.9 MHz, d6-DMSO):
δ = 3.8598 (16.0); 3.3560 (0.5); 2.5322 (0.6); 2.5288 (1.2); 2.5253 (1.7); 2.5217 (1.2); 2.5184 (0.6)
VIIIa.05: 1H-NMR(300.2 MHz, CDCl3):
δ = 7.2983 (1.3); 3.9521 (16.0); 1.5875 (0.4); 0.0350 (1.7)
VIIIa.06: 1H-NMR(300.2 MHz, d6-DMSO):
δ = 19.6514 (1.2); 19.4242 (1.2); 14.4211 (1.5); 14.2144 (4.5); 14.0488 (9.5); 13.9419 (4.6); 13.7837 (1.7); 13.6736 (1.2); 13.6487 (1.2); 13.5662 (1.3); 9.3511 (1.3); 5.7749 (3.0); 4.0838 (1.6); 4.0599 (3.6); 4.0367 (3.6); 4.0129 (1.4); 3.7199 (1.5); 3.6986 (1.4); 3.6881 (1.6); 3.6447 (2.0); 3.5905 (2.2); 3.5604 (2.8); 3.3605 (11.6); 3.1076 (1.9); 3.0934 (1.9); 3.0852 (2.0); 3.0078 (1.6); 2.9717 (1.3); 2.9121 (1.4); 2.8858 (1.6); 2.7479 (1.7); 2.5339 (95.7); 2.5278 (198.8); 2.5217 (271.4); 2.5157 (195.8); 2.5096 (91.8); 2.4429 (1.8); 2.4204 (1.3); 2.2912 (2.1); 2.0080 (16.0); 1.2510 (7.5); 1.2177 (5.6); 1.1940 (10.0); 1.1702 (5.6); 0.8674 (1.7); 0.8481 (1.5); 0.8110 (1.2); 0.0286 (13.0); 0.0178 (337.9); 0.0069 (13.0); −0.0500 (1.4); −0.1807 (1.7)
VIIIa.07: 1H-NMR(499.9 MHz, CDCl3):
δ = 7.2630 (2.8); 4.4029 (2.5); 4.3887 (7.6); 4.3744 (7.7); 4.3601 (2.6); 2.0073 (0.6); 1.5552 (2.0); 1.4026 (8.0); 1.3883 (16.0); 1.3740 (7.8); 1.2543 (0.5); −0.0002 (3.2)
VIIIa.08: 1H-NMR(499.9 MHz, CDCl3):
δ = 7.2606 (15.4); 5.2995 (3.1); 4.3996 (2.5); 4.3853 (7.7); 4.3710 (7.8); 4.3568 (2.6); 1.5458 (28.2); 1.3998 (8.0); 1.3856 (16.0); 1.3713 (7.9); 1.2560 (0.6); −0.0002 (15.9)
IXb.01: 1H-NMR(300.2 MHz, CDCl3):
δ = 7.3562 (4.5); 7.2987 (4.8); 6.3762 (1.1); 4.2401 (1.4); 4.2163 (4.4); 4.1925 (4.5); 4.1688 (1.5); 2.5394 (16.0); 1.7118 (1.3); 1.6952 (3.6); 1.6843 (3.8); 1.6692 (1.7); 1.6163 (0.3); 1.3412 (1.7); 1.3261 (3.7); 1.3153 (3.7); 1.2979 (6.0); 1.2740 (9.6); 1.2502 (4.6); 0.0354 (6.2)
IXa.01: 1H-NMR(600.1 MHz, d6-DMSO):
δ = 8.6444 (2.5); 8.3131 (4.9); 7.1174 (6.0); 4.0758 (1.6); 4.0640 (5.0); 4.0522 (5.0); 4.0404 (1.6); 3.3303 (5.5); 3.3257 (16.0); 3.3238 (13.3); 3.3012 (1.6); 2.5080 (5.1); 2.5052 (10.5); 2.5022 (14.0); 2.4993 (9.8); 2.4967 (4.5); 2.3608 (18.4); 2.1549 (0.4); 1.4162 (1.5); 1.4084 (3.9); 1.4029 (4.2); 1.3955 (1.6); 1.2397 (0.5); 1.1588 (5.3); 1.1469 (11.0); 1.1405 (1.8); 1.1350 (7.0); 1.1276 (3.7); 1.1196 (1.3)
IXa.02: 1H-NMR(600.1 MHz, d6-DMSO):
δ = 8.3748 (0.6); 8.3652 (1.2); 8.3555 (0.6); 7.1387 (5.8); 4.1343 (1.6); 4.1225 (5.0); 4.1106 (5.0); 4.0988 (1.6); 3.9322 (5.2); 3.9224 (5.2); 3.3259 (16.0); 2.8913 (0.4); 2.5081 (4.3); 2.5052 (9.3); 2.5021 (12.9); 2.4991 (9.2); 2.4961 (4.2); 2.3919 (18.2); 2.1680 (0.4); 1.2393 (0.5); 1.2146 (5.6); 1.2100 (0.3); 1.2027 (11.6); 1.1981 (0.6); 1.1909 (5.5)
IXa.03: 1H-NMR(600.1 MHz, d6-DMSO):
δ = 8.2288 (0.6); 8.2159 (0.6); 7.1279 (2.7); 7.1274 (2.6); 4.1797 (0.7); 4.1717 (0.6); 4.1677 (1.1); 4.1599 (0.6); 4.1547 (1.0); 4.1538 (1.1); 4.1418 (0.9); 4.1131 (0.9); 4.1013 (0.9); 4.0951 (0.5); 4.0832 (0.5); 3.3309 (5.8); 3.3227 (16.0); 2.8917 (0.5); 2.7326 (0.4); 2.7318 (0.4); 2.5081 (2.6); 2.5051 (5.9); 2.5020 (8.3); 2.4990 (6.1); 2.4960 (3.0); 2.3704 (8.8); 2.1646 (0.4); 2.1532 (0.6); 2.1418 (0.6); 2.1304 (0.4); 1.2129 (2.9); 1.2010 (6.0); 1.1957 (0.4); 1.1892 (2.8); 0.9602 (3.8); 0.9489 (3.8); 0.9372 (3.7); 0.9259 (3.7)
IXa.04: 1H-NMR(600.1 MHz, d6-DMSO):
δ = 8.3807 (0.4); 8.3678 (0.4); 7.2942 (1.0); 7.2836 (2.3); 7.2809 (1.8); 7.2706 (0.3); 7.2189 (0.4); 7.0902 (1.6); 4.1169 (0.7); 4.1141 (0.7); 4.1050 (0.7); 4.1023 (0.7); 3.3462 (5.2); 3.3412 (15.2); 3.3404 (16.0);

TABLE A-continued

| NMR peak lists |
|---|
| 3.1372 (0.4); 3.1285 (0.3); 3.0677 (0.4); 3.0507 (0.4); 2.5147 (1.5); 2.5118 (3.3); 2.5088 (4.6); 2.5058 (3.4); 2.5029 (1.6); 2.2220 (4.5); 1.1714 (1.4); 1.1596 (3.0); 1.1478 (1.4) |
| Xa.01: 1H-NMR(300.2 MHz, d6-DMSO): |
| δ = 8.1387(1.3); 6.3153(1.9); 4.0968(0.6); 4.0731(2.1); 4.0495(2.1); 4.0259(0.7); 3.3400(16.0); 2.5351(0.6); 2.5291(1.4); 2.5230(1.9); 2.5169(1.4); 2.5108(0.6); 2.3046(7.5); 1.4114(0.5); 1.3953(1.2); 1.3843(1.4); 1.3703(0.6); 1.1820(2.2); 1.1583(4.8); 1.1347(2.2); 1.1258(0.7); 1.1115(1.4); 1.1005(1.3); 1.0842(0.5); 0.0217(1.9) |
| XIa.01: 1H-NMR(300.2 MHz, CDCl3): |
| δ = 7.2987 (3.5); 6.2815 (0.7); 4.2225 (0.6); 4.1988 (2.1); 4.1750 (2.1); 4.1513 (0.7); 3.8296 (0.9); 3.4388 (1.6); 2.8084 (2.5); 2.5446 (1.6); 2.5326 (7.3); 1.6725 (0.7); 1.6561 (1.6); 1.6453 (1.6); 1.6302 (0.8); 1.5840 (16.0); 1.2824 (2.2); 1.2587 (4.7); 1.2501 (1.4); 1.2350 (2.6); 1.2229 (0.5); 0.0341 (3.4) |
| XIIIa.01: 1H-NMR(499.9 MHz, d6-DMSO): |
| δ = 4.2571 (0.5); 4.2430 (1.6); 4.2288 (1.6); 4.2146 (0.5); 3.3173 (2.7); 2.5080 (0.7); 2.5046 (1.0); 2.5012 (0.8); 2.4380 (5.9); 1.4974 (16.0); 1.2924 (1.6); 1.2782 (3.4); 1.2640 (1.7) |
| XIIIa.02: 1H-NMR(499.9 MHz, d6-DMSO): |
| δ = 3.3167 (18.1); 2.5081 (8.0); 2.5046 (11.3); 2.5011 (8.8); 2.4215 (5.9); 1.4920 (16.0); 1.2394 (1.8) |

BIOLOGICAL DATA

Example A: *Xanthomonas Campestris* pv. *Campestris* In Vitro Cell Test

Solvent: DMSO
Culture medium: LB broth medium (Luria Broth Miller) Sigma

Inoculum: bacteria suspension

Compounds to be tested were solubilized in DMSO and the solution used to prepare the required range of concentrations. The final concentration of DMSO used in the assay was ≤1%.

Inoculum was prepared from a pre-culture of bacteria grown in liquid medium and diluted to the desired optical density (OD).

Compounds were evaluated for their ability to inhibit bacteria growth in liquid culture assay. The compounds were added in the desired concentrations to culture medium containing the bacteria suspension. After 24 h of incubation, the efficacy of compounds was determined by spectrometric measurement of bacteria growth. Inhibition was determined by comparing the absorbance values in wells containing the compounds with the absorbance in control wells without compounds.

In this test, the following compounds according to the invention showed no direct activity at a concentration of 20 ppm of tested compound: I.01; I.02; I.03; I.04; I.05; I.06; I.07; I.08; I.09; I.10; I.11; I.12; I.13; I.14; I.15; I.17; I.18; I.19; I.20; I.21; I.22; I.23; I.24; I.25; I.26; I.27; I.28; I.29; I.30; I.31; I.32; I.33; I.34; I.35; I.36; I.37; I.38; I.39; I.40; 1.41; I.42; I.43; I.44; I.45; I.46; I.47; I.48; I.49; I.50; 1.51; I.52; I.53; I.54; I.55; I.56; I.57; I.58; I.59; 1.60; 1.61.

Example B: In Vivo Preventive Test on *Xanthomonas campestris* pv. *Campestris* (Black Rot on Cabbage)

The tested compounds were prepared by homogenization in a mixture of acetone/Dimethyl sulfoxide/Tween®, and then diluted with water to obtain the desired concentration.

The young plants of cabbage were treated by spraying the compound prepared as described above. Control plants were treated only with an aqueous solution of acetone/Dimethyl sulfoxide/Tween®.

After 72 hours, the plants were contaminated by spraying the leaves with an aqueous bacteria suspension of *Xanthomonas campestris* pv. *campestris*. The contaminated cabbage plants were incubated for 8 or 10 days at 27° C. at 95% relative humidity.

The test was evaluated 8 or 10 days after the inoculation. 0% means an efficacy which corresponds to that of the control plants while an efficacy of 100% means that no disease was observed.

In this test, the following compounds according to the invention showed efficacy between 70% and 79% at a concentration of 31 ppm of tested compound: I.08; I.11; I.32; I.34; I.44; I.45; I.50; I.59; I.60; I.68; I.74; I.79; I.80; I.81; I.82; I.90; I.58.

In this test, the following compounds according to the invention showed efficacy between 80% and 89% at a concentration of 31 ppm of tested compound: I.02; I.15; I.16; I.20; I.25; I.33; I.36; I.40; I.42; I.43; I.52; I.53; I.57.

In this test, the following compounds according to the invention showed efficacy between 90% and 100% at a concentration of 31 ppm of tested compound: I.03; I.04; I.21; I.31; I.41; I.55; I.56.

Example C: Comparative Examples

Compounds CMP3, CMP4, CMP5 and CMP6 were tested in an in vivo preventive test on *Xanthomonas campestris* pv. *campestris* (black rot on cabbage) in the same conditions as described in Example B.

Compounds CMP3, CMP4, CMP5 and CMP6 were prepared in accordance with the teaching of U.S. Pat. No. 5,534,541.

The results are as shown in the table below.

| Ex. | $R^1$ | $R^2$ | $R^3$ | $R^4$ | $R^5$ | $R^6$ | Efficacy (%) |
|---|---|---|---|---|---|---|---|
| CMP3* | Br | Br | Br | isopropyl | H | Et | 33 |
| I.04 | Br | Br | Me | isopropyl | H | Et | >90 |
| CMP4 | Br | Br | H | H | H | Et | 0 |
| I.02 | Br | Br | Me | H | H | Et | >80 |
| CMP5* | Br | Br | H | methyl | H | H | 0 |
| I.79 | Br | Br | Me | methyl | H | H | >70 |

-continued

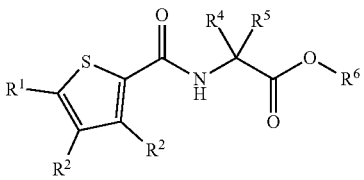

| Ex. | R¹ | R² | R³ | R⁴ | R⁵ | R⁶ | Efficacy (%) |
|---|---|---|---|---|---|---|---|
| CMP6* | Br | Br | H | 2-methylpropyl | H | H | 15 |
| I.90 | Br | Br | Me | 2-methylpropyl | H | H | >70 |

*S enantiomer

Example D: Induction of Defense Gene Expression in *Arabidopsis thaliana*

*Arabidopsis thaliana* reporter plants containing the coding sequence of a green fluorescent protein (GFP) linked to the salicylate responsive promoter sequence of the PR1 (pathogenesis-related protein I) gene (AT2G14610) were grown for five days and then sprayed with compounds. On the 3$^{rd}$ day after spraying, plant fluorescence was assessed with a MacroFluo instrument from Leica Microsystems (Wetzlar, Germany). Fluorescences were quantified with the Meta-Morph Microscopy Automation & Image Analysis Software (Molecular Devices, Sunnyvale, Calif., United States).

Background fluorescence in mock treated leaves was set as 1.00. Salicylic acid treatment (300 ppm) resulted in a relative fluorescence value of 2.70, proving the validity of the test system.

In this test, the following compounds according to the invention showed a relative fluorescence value at least above 2 at a concentration of 300 ppm of compound: I.01; I.03; I.04; I.05; I.06; I.07; I.08; I.09; I.11; I.13; I.16; I.19; I.20; I.21; I.23; I.24; I.26; I.29; I.30; I.32; I.33; I.35; I.36; I.37; I.39; I.43; I.46; I.47; I.48; I.49; I.50; I.51; I.52; I.53; I.54; I.55; I.57; I.58; I.59; I.60; I.61; I.63; I.64; I.65; I.66; I.67; I.68; I.71; I.72; I.73; I.75; I.76; I.77; I.78; I.79; I.80; I.81; I.82; I.83; I.84; I.85; I.86; I.87; I.88; I.89; I.90; I.91.

In this test, the following compounds according to the invention showed a relative fluorescence value at least above 2 at a concentration of 75 ppm of compound: I.02; I.10; I.18; I.25; I.27; I.31; I.34; I.40; I.41; I.56; I.69; I.70; I.15; I.22.

Salicylate is a major defense hormone against plant pathogens. All the compounds described above stimulate the salicylic acid pathway and therefore could protect plants against a wide range of pathogens.

The invention claimed is:
1. A compound of formula (I):

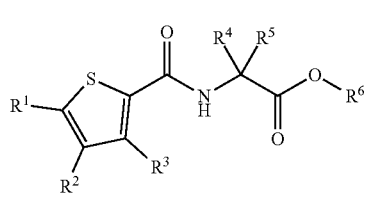

(I)

wherein
R¹ and R² are identical and are a chlorine atom or a bromine atom;

R³ is methyl;

R⁴ is selected from the group consisting of hydrogen atom, $C_1$-$C_6$-alkyl, aralkyl, aralkyl substituted by hydroxyl, $C_1$-$C_6$-alkyl substituted by a $C_1$-$C_6$-alkylsulfanyl and R⁵ is a hydrogen atom; or R⁴ and R⁵ form, together with the carbon atom to which they are linked, a cyclopropyl;

R⁶ is selected from the group consisting of hydrogen atom, $C_1$-$C_6$-alkyl, $C_1$-$C_6$-haloalkyl, $C_1$-$C_6$-cyanoalkyl, $C_2$-$C_6$-alkenyl, $C_2$-$C_6$-alkynyl, $C_3$-$C_8$-cycloalkyl, aryl, aralkyl, 4-, 5- or 6-membered heterocyclyl, —$C_1$-$C_6$-alkyl-Si($C_1$-$C_6$-alkyl)$_3$ and —$C_1$-$C_6$-alkyl-$C_3$-$C_8$-cycloalkyl.

2. The compound of formula (I) according to claim 1 wherein R⁴ is selected from the group consisting of hydrogen atom, $C_1$-$C_6$-alkyl, benzyl, benzyl substituted by hydroxyl, $C_1$-$C_6$-alkyl substituted by a $C_1$-$C_6$-alkylsulfanyl and R⁵ is a hydrogen atom; or R⁴ and R⁵ form, together with the carbon atom to which they are linked, a cyclopropyl.

3. The compound of formula (I) according to claim 1 wherein R⁶ is selected from the group consisting of hydrogen atom, $C_1$-$C_6$-alkyl, $C_1$-$C_6$-haloalkyl, $C_1$-$C_6$-cyanoalkyl, $C_2$-$C_6$-alkenyl, $C_2$-$C_6$-alkynyl, $C_3$-$C_8$-cycloalkyl, phenyl, benzyl, 4-, 5- or 6-membered heterocyclyl, —$C_1$-$C_6$-alkyl-Si($C_1$-$C_6$-alkyl)$_3$ and —$C_1$-$C_6$-alkyl-cyclopropyl.

4. The compound of formula (I) according to claim 1 wherein R⁶ is selected from the group consisting of hydrogen atom, $C_1$-$C_6$-alkyl, $C_1$-$C_6$-haloalkyl, $C_1$-$C_6$-cyanoalkyl, $C_2$-$C_6$-alkenyl, $C_2$-$C_6$-alkynyl, $C_3$-$C_8$-cycloalkyl, phenyl, benzyl, oxetanyl, thietanyl, dioxothietanyl, oxolanyl, oxanyl, —$C_1$-$C_6$-alkyl-Si($C_1$-$C_6$-alkyl)$_3$ and —$C_1$-$C_6$-alkyl-cyclopropyl.

5. A composition comprising at least one compound of formula (I) according to claim 1 and at least one agriculturally suitable auxiliary.

6. A method for controlling bacterial diseases comprising the step of applying (i) at least one compound of formula (I) according to claim 1, or (ii) a composition comprising at least one compound of formula (I) according to claim 1 and at least one agriculturally suitable auxiliary to plants, plant parts, seeds, fruits or to the soil in which the plants grow.

7. A process for preparing a compound of formula (I) according to claim 1 comprising the step of reacting a compound of formula (IV) or a salt thereof with a compound of formula (V) or a salt thereof:

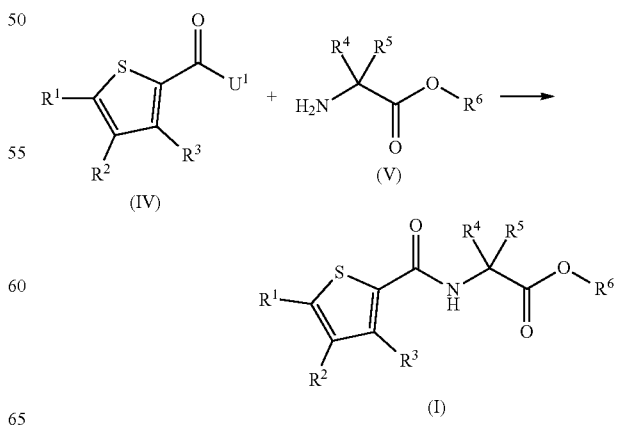

wherein

R$^1$, R$^2$, R$^3$, R$^4$, R$^5$ and R$^6$ are as recited in claim 1;

U$^1$ is a halogen atom, a hydroxy group or a C$_1$-C$_6$-alkoxy group.

8. A process for preparing a compound of formula (I) according to claim 1 comprising the step of reacting a compound of formula (VI) or a salt thereof with a compound of formula (VII) or a salt thereof:

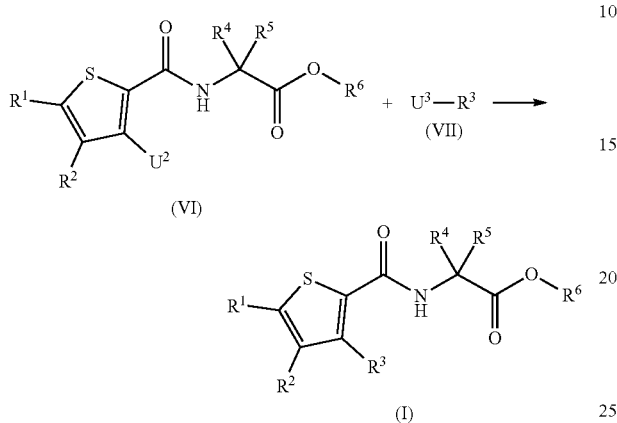

wherein

R$^1$, R$^2$, R$^3$, R$^4$, R$^5$ and R$^6$ are as recited in claim 1;

U$^2$ is a bromine atom, an iodine atom, a mesylate group, a tosylate group or a triflate group; and U$^3$ is a boron derivative or a halogenometal;

provided that when R$^1$ and R$^2$ are bromine atoms, U$^2$ is not a bromine atom.

9. The process according to claim 8 further comprising the step of reacting a compound of formula (VIII):

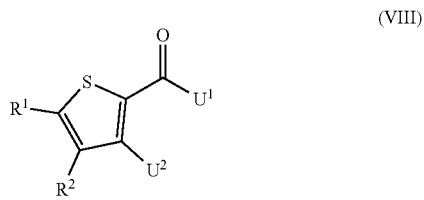

wherein

R$^1$, R$^2$ and U$^2$ are as recited in claim 8; and

U$^1$ is a halogen atom, a hydroxy group or a C$_1$-C$_6$-alkoxy group, with a compound of formula (V):

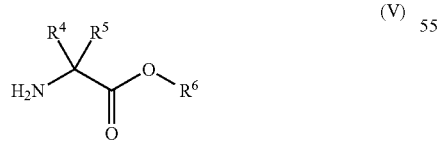

wherein

R$^4$, R$^5$ and R$^6$ are as defined in claim 8, to provide a compound of formula (VI).

10. A process for preparing a compound of formula (I) according to claim 1 comprising the step of performing a bromination or chlorination of a compound of formula (IX) or a salt thereof:

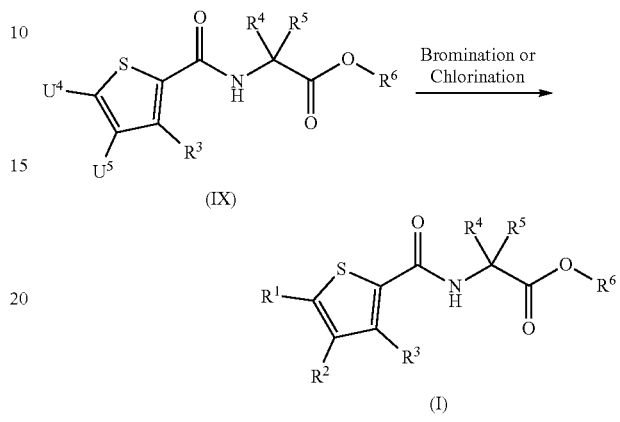

wherein

R$^1$, R$^2$, R$^3$, R$^4$, R$^5$ and R$^6$ are as recited in claim 1;

U$^4$ is a hydrogen atom, a chlorine atom or a bromine atom; and

U$^5$ is a hydrogen atom, a chlorine atom or a bromine atom;

provided that at least one of U$^4$ or U$^5$ is a hydrogen atom.

11. A process for preparing a compound of formula (I) according to claim 1 comprising the step of performing a diazotation of a compound of formula (X) or a salt thereof followed by an aromatic substitution:

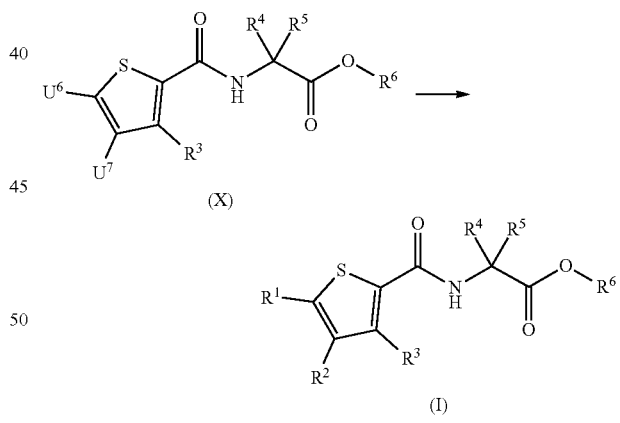

wherein

R$^1$, R$^2$, R$^3$, R$^4$, R$^5$ and R$^6$ are as recited in claim 1;

U$^6$ is an amino group, a chlorine atom or a bromine atom;

U$^7$ is an amino group, a chlorine atom or a bromine atom;

provided that at least one of U$^6$ or U$^7$ is an amino group.

* * * * *